United States Patent [19]
DeWitt et al.

[11] Patent Number: 5,565,173
[45] Date of Patent: *Oct. 15, 1996

[54] APPARATUS AND METHOD FOR MULTIPLE SIMULTANEOUS SYNTHESIS

[75] Inventors: Sheila H. H. DeWitt, Dexter, Mich.; John S. Kiely, San Diego, Calif.; Michael R. Pavia, Newton, Mass.; Mel C. Schroeder, Dexter; Charles J. Stankovic, Saline, both of Mich.

[73] Assignee: Warner-Lambert Company, Morris Plains, N.J.

[ * ] Notice: The term of this patent shall not extend beyond the expiration date of Pat. No. 5,324,483.

[21] Appl. No.: 461,998

[22] Filed: Jun. 5, 1995

Related U.S. Application Data

[63] Continuation of Ser. No. 430,696, Apr. 28, 1995, which is a continuation of Ser. No. 217,347, Mar. 24, 1994, abandoned, which is a division of Ser. No. 12,557, Feb. 2, 1993, Pat. No. 5,324,483, which is a continuation-in-part of Ser. No. 958,383, Oct. 8, 1992, abandoned.

[51] Int. Cl.$^6$ .............................. B01J 19/00; B01J 8/00; C12M 1/00; C07K 17/00
[52] U.S. Cl. ........................ 422/131; 422/130; 422/196; 435/304.1; 435/305.2; 935/88
[58] Field of Search .................................... 422/130, 131, 422/99, 100, 101, 102, 103, 104, 196; 435/305.2, 304.1; 211/71, 74; 935/88

[56] References Cited

U.S. PATENT DOCUMENTS 3,192,184   6/1965   Brill et al. .

(List continued on next page.)

FOREIGN PATENT DOCUMENTS

40130/89   3/1990   Australia .

(List continued on next page.)

OTHER PUBLICATIONS

*Peptides—Chemistry, Structure and Biology*, "Automated Multiple Peptide Synthesis with BOP Activation", by H. Gausepohl et al.; pp. 1003–1004; Jul. 1990.

(List continued on next page.)

*Primary Examiner*—Robert J. Warden
*Assistant Examiner*—Robert Carpenter
*Attorney, Agent, or Firm*—Charles W. Almer, III; Francis J. Tinney

[57] ABSTRACT

An apparatus and method which provides a suitable location for multiple, simultaneous synthesis of compounds. The apparatus consists of: a reservoir block having a plurality of wells; a plurality of reaction cubes, usually gas dispersion tubes, having filters on their lower ends; a holder block, having a plurality of apertures; and a manifold, which may have ports to allow introduction/maintenance of a controlled environment. The manifold top wall has apertures and a detachable place with identical apertures. The apparatus is constructed from materials which will accommodate heating, cooling, agitation, or corrosive reagents. Gaskets are placed between the components. Rods or clamps are provided for fastening the components together. Apparatus operation involves placing the filters on the lower ends of the reaction tubes in the reservoir block wells, and the upper ends passing through the holder block apertures and into the manifold. The apparatus provides in excess of 1 mg of each product with structural knowledge and control over each compound. The apparatus can be adapted to manual, semi-automatic or fully automatic performance. Using the apparatus a series of building blocks are covalently attached to a solid support. These building blocks are then modified by covalently adding additional different building blocks or chemically modifying some existing functionality until the penultimate structure is achieved. This is then cleaved from the solid support by another chemical reaction into the solution within the well yielding an array of newly synthesized individual compounds, which after postreaction modification, if necessary, are suitable for testing for activity.

16 Claims, 9 Drawing Sheets

U.S. PATENT DOCUMENTS

| | | |
|---|---|---|
| 3,379,315 | 4/1968 | Broadwin . |
| 3,518,164 | 6/1970 | Andelin et al. . |
| 3,752,651 | 8/1973 | Bush . |
| 3,905,482 | 9/1975 | Knulst . |
| 3,918,917 | 11/1975 | Ashina et al. .......................... 422/197 |
| 3,918,920 | 11/1975 | Barber . |
| 3,933,435 | 1/1976 | Menashi et al. ....................... 422/199 |
| 4,304,865 | 12/1981 | O'Brien et al. . |
| 4,477,578 | 10/1984 | Miles et al. ............................. 422/100 |
| 4,495,150 | 1/1985 | Cook et al. . |
| 4,511,534 | 4/1985 | Bennett, Jr. et al. . |
| 4,597,946 | 7/1986 | Ward . |
| 4,689,405 | 8/1987 | Frank et al. . |
| 4,787,988 | 11/1988 | Bertoncini et al. ..................... 210/808 |
| 4,929,427 | 5/1990 | Guala . |
| 4,929,798 | 5/1990 | de Lasa . |
| 4,992,544 | 2/1991 | Miller . |
| 5,049,507 | 9/1991 | Hawke et al. . |
| 5,053,454 | 10/1991 | Judd . |
| 5,133,939 | 7/1992 | Mahe . |
| 5,177,060 | 1/1993 | Wei . |
| 5,186,898 | 2/1993 | Bridgham et al. . |
| 5,288,514 | 2/1994 | Ellman . |

FOREIGN PATENT DOCUMENTS

| | | |
|---|---|---|
| 0196174 | 10/1986 | European Pat. Off. . |
| 0355582 | 2/1990 | European Pat. Off. . |
| 2748797 | 5/1978 | Germany . |
| 3723004 | 1/1989 | Germany . |
| 4005518 | 8/1991 | Germany . |
| WO9009395 | 8/1990 | WIPO . |
| WO9015070 | 12/1990 | WIPO . |
| WO9210092 | 6/1992 | WIPO . |

OTHER PUBLICATIONS

*J. Am. Chem. Soc.*, 1992, 114, pp. 10997–10998, "A General and Expedient Method for the Solid–Phase Synthesis of 1,4–Benzodiazepine Derivatives", by B. Bunin et al.

Vol. 45, No. 24, "Fully Automatic Simultaneous Multiple Peptide Synthesis In Micromolar Scale etc." by G. Schnorrenberg et al.; pp. 7759–7764; 1989.

APPARATUS AND METHOD FOR MULTIPLE SIMULTANEOUS SYNTHESIS

This is a continuation of U.S. application Ser. No. 08/430,696, filed on Apr. 28, 1995, now pending, which is a continuation application of U.S. application Ser. No. 08/217,347, filed Mar. 24, 1994, now abandoned, which is a divisional application of U.S. application Ser. No. 08/012,557, filed Feb. 2, 1993, now U.S. Pat. No. 5,324,483, granted Jun. 28, 1994, which is a Continuation-In-Part application of U.S. Ser. No. 07/958,383, filed Oct. 8, 1992, now abandoned.

BACKGROUND OF THE INVENTION

1. Field of the Invention

The invention relates to an apparatus and method which are used for the multiple, simultaneous synthesis of compounds, including but not limited to organic compounds.

2. Description of Related Art

It is well known in the art that peptides or oligonucleotides may be multiply and simultaneously synthesized. In a basic, single synthesis of a peptide, amino acids are simultaneously coupled to a functionalized solid support. Several methods have been developed by which peptides or oligonucleotides may be multiply synthesized. One such methodology for peptide synthesis was disclosed in Geysen, et al, International Publication Number WO 90/09395. Geysen's method involves functionalizing the termini of polymeric rods and sequentially immersing the termini in solutions of individual amino acids. Geysen's approach has proven to be impractical for commercial production of peptides since only very minute quantities of polypeptides may be generated. In addition, this method is extremely labor intensive. A second method of peptide or oligonucleotide synthesis was developed by Affymax Technologies N.V. and disclosed in U.S. Pat. No. 5,143,854. The Affymax method involves sequentially using light for illuminating a plurality of polymer sequences on a substrate and delivering reaction fluids to said substrate. This method of synthesis has numerous drawbacks, including the fact that the products are noncleavable and that the process produces large numbers, but only minute quantities of products. A further method and device for producing peptides or oligonucleotides is disclosed in Houghton, European Patent Number 196174. Houghton's apparatus is a polypropylene mesh container, similar to a tea-bag, which encloses reactive particles. The containers, however, are not amenable to general organic synthesis techniques. Further apparatus are disclosed in German Published Patent Application Number DE 4005518 and European Patent Number 0355582, issued to Boehringer Ingelheim KG. Like the earlier devices, these apparatus are not suitable for the synthesis of general organic compounds and are directed toward peptide or oligonucleotide synthesis.

The synthesis of general organic compounds, poses many difficulties which are absent in the synthesis of peptides or oligonucleotides. An approach describing the synthesis of unnatural, oligomeric peptides is reported by Simon, et al, in *Proceedings of the National Academy of Sciences U.S.A.* 1992;89:9367. Accordingly, none of the disclosed devices or methods for the multiple, simultaneous synthesis of peptides or oligonucleotides are useful for the synthesis of general organic compounds. Among the many special problems found in the synthesis of general organic compounds, as opposed to peptide or oligonucleotide synthesis, is the problem of providing a device which will accommodate the wide range of synthetic manipulations required for organic synthesis. The synthesis of general organic compounds often requires such varied conditions as an inert atmosphere, heating, cooling, agitation, and an environment to facilitate reflux. Additionally, such synthesis requires chemical compatibility between the materials used in the apparatus for multiple synthesis and the reactants and solvents. Consequently, the apparatus must be constructed of materials which are resistant to organic synthesis conditions and techniques. Organic synthesis also often requires agitation. Such agitation may be accomplished by magnetic stirring, sonicating, or rotational shaking. None of the prior art devices are suitable for use under these special conditions required for general organic synthesis.

While undeniably useful, peptides or oligonucleotides have significant limitations in their application to pharmaceutical discovery programs. The chemical leads discovered from these collections of compounds require extensive modification due to the general unsuitability of peptides or nucleotides as stable, orally active drugs. The building blocks utilized are, in general, limited even allowing for the use of unnatural enantiomers or artificial amino acids and modified nucleotides. The peptides or oligonucleotides generated possess a repetitive linkage, amide or phosphate moiety, which limits their structural diversity.

The principal object of the present invention, therefore, is to overcome the limitations of the previous apparatus and methods which are limited to peptide or oligonucleotide synthesis and to provide an apparatus and method which will accommodate multiple, simultaneous synthesis of general organic compounds including, but not limited to, nonpeptide or nonnucleotide compounds.

SUMMARY OF THE INVENTION

The present invention is directed to an apparatus and method which will provide a suitable environment for the synthesis of organic compounds. Additionally, the synthesis of inorganic compounds, organometallic compounds, and the like is entirely within the scope of the invention.

Central to the demonstration of this concept is the need to devise a "general" method for multiple, simultaneous synthesis of organic compounds. The synthesis method developed must satisfy the following criteria. The compounds should be simultaneously synthesized in an array format, which is compatible with the standard techniques of organic synthesis. The final compounds should be produced individually (not as mixtures) in soluble form. The quantity generated should be greater than 1 mg and in sufficiently pure form to allow direct biological testing. Additionally, to the extent possible, sample handling should be carried out using automated systems for speed, accuracy, and precision. A final requirement is that the growing compounds must be readily separable from by-products and reagents. Solid phase synthesis techniques commonly used in peptide or oligonucleotide synthesis enable achievement of this criteria. Typical solid supports (resins) include cross-linked divinylbenzene-styrene (polystyrene), controlled pore glass (CPG), polyacrylamides, poly(ethylene glycol)monomethyl ether and poly(ethylene glycol) (PEG), silica gel, cellulose, acrylic acid grafted polypropylene, and the like. Additionally, the solid support contains a reactive moiety. Thus, a functionalized solid support is an insoluble material containing an accessible reactive moiety such as, for example, a carboxylic acid, alcohol, amine, halomethyl and the like which is used to covalently attach an incoming building block. A further objective of the present invention is to synthesize products with molecular weights of less than, but not limited to, 1500 g/mol.

The approach described herein greatly increases the flexibility and diversity of structures that can be produced by a parallel, solid phase synthesis technology. Since neither the building blocks nor the methods for connecting them are in any way limited, the chemistries compatible with this apparatus and method are very broad, encompassing nearly all organic reactions. The key feature which allows for the success of this method is containment of a solid support within a gas dispersion tube. This feature provides a unique means to segregate and manipulate the growing compounds on a solid support. Equipment designed to simultaneously manipulate the plurality of gas dispersion tubes and provide an environment to perform standard organic synthesis techniques enables the multiple, simultaneous synthesis of, for example, 8, 40, 100, or more reactions at one time.

The steps necessary to perform a synthesis are 1) development of a synthetic route that will be feasible on a solid support, 2) verification of the resin-based synthesis using several representative examples, and 3) execution of multiple, simultaneous synthesis within an array format to generate, for example, 8, 20, 40 unit arrays and the like.

The method involves the sequential coupling of building blocks to form resin-bound intermediates until the final or penultimate compound at each location in the array is constructed, but still resin-bound. In addition to coupling the building blocks directly, one may add, if required, a coupling agent or reagent which is intended to chemically participate in forming the covalent bond between the solid support and the building block or between building blocks. Coupling reagents include catalysts, chemical reagents, and the like. The sequential coupling reactions can be performed as illustrated in the following procedures:

I. a functionalized solid support, a building block, a coupling reagent and solvent are reacted together; or
II. a functionalized solid support, a reactive building block and solvent are reacted together; or
III. a solid support with attached building block, a second building block, a coupling reagent and a solvent are reacted together; or
IV. a solid support with attached building block, a second reactive building block, and a solvent are reacted together.

Preferably, the sequential coupling reactions can be performed as illustrated in the following procedures:

I.
(a) charging the apparatus with a solid support with attached building block wherein the building block has a reactive moiety protected by a proteting group and a solvent;
(b) removing the protecting group from the reactive moiety with a deprotection reagent;
(c) removing the deprotection reagent;
(d) sequentially adding additional reactive building blocks in solvents to synthesize the compounds; and
(e) cleaving the compounds from the solid support within the apparatus to afford the desired compounds; or II.
(a) charging the apparatus with a solid support with attached building block wherein the building block has a reactive moiety protected by a protecting group and a solvent;
(b) removing the protecting group from the reactive moiety with a deprotection reagent;

(c) removing the deprotection reagent;
(d) adding a coupling reagent in a solvent;
(e) sequentially adding additional reactive building blocks and optionally coupling reagents in solvents to synthesize the compounds; and
(f) cleaving the compounds from the solid support within the apparatus to afford the desired compounds; or III.
(a) charging the apparatus with a solid support with attached building block and a solvent;
(b) adding a reagent for changing the oxidation state of the reactive moiety;
(c) sequentially adding additional reactive building blocks in solvents to synthesize the compounds; and
(d) cleaving the compounds from the solid support within the apparatus to afford the desired compounds; or IV.
(a) charging the apparatus with a solid support with attached building block and a solvent;
(b) adding a reagent for changing the oxidation state of the reactive moiety;
(c) adding a coupling reagent in a solvent;
(d) sequentially adding additional reactive building blocks and optionally coupling reagents in solvents to synthesize the compounds; and
(e) cleaving the compounds from the solid support within the apparatus to afford the desired compounds.

Other strategies for constructing the growing compounds on the solid support are possible and are encompassed within the scope of the present invention.

Cleavage of the final compound from the resin yields a product which can be readily separated from the spent resin. Several options are available for achieving this cleavage and these are illustrated in Scheme 1. A single, invariant cleavage reagent can be employed to attack the resin-bound product linkage to yield a final compound containing an invariant functionality. Cleavage can be affected utilizing a variety of incoming building blocks to attack the resin linkage and give a product with variations in structure at the site of detachment. An alternative strategy constructs a precursor compound (resin-bound) possessing a distal functionality which, when activated or unmasked, will attack the resin-linking bond resulting in ejection of the cyclized final compound into solution. Since "unreacted" compounds remain attached to the resin, the latter option provides a means to produce cleaner final products.

The use of a solid support to multiply and simultaneously synthesize a subset of related, individual compounds requires a means of preparing the compounds in an array format. The method for constructing a compound array is illustrated with the following two examples: In one variant, the final compound, prior to detachment from the solid support, can be constructed from two building blocks/portions/halves utilizing a single coupling reaction to join the two smaller parts. One starts by selecting the congeners of building block #1 (for example, 3; A, B, and C) to be directly attached to the solid support and the number of congeners of the second half (building block #2) of the final compound that will be attached to the first building block (for example, 3; X, Y, and Z). The number of congeners of building block #1 multiplied by the number of congeners of building block #2 gives the number of locations contained in the array, in this example 3×3=9. Each of the congeners of #1 is covalently attached to the solid support a number of times equal to the number of congeners of #2, herein each of the first building blocks (A, B, and C) is coupled to the support in three locations each (9 couplings total). The covalent joining of the second building block to the first building block is now carried out with each of the congeners of building block #2 (i.e., A, B, and C are each coupled once with Z giving AZ, BZ, and CZ). Completion of the progression of couplings yields all nine expected permutations. This is illustrated in Scheme A.

| SCHEME A. Construction of an Array Involving One Coupling Reaction | | | |
|---|---|---|---|
| Building | Building Block #1 | | |
| Block #2 | A | B | C |
| X | AX | BX | CX |
| Y | AY | BY | CY |
| Z | AZ | BZ | Cz |

To achieve additional structural variation, one can utilize the addition of a third set of building blocks (for example, 3; 1, 2, and 3) and thus a second coupling reaction to provide 27 elements from an array of 3×3×3=27. To accomplish this in the array synthesis will require that the first array (building block #1 coupled to building block #2 which is nine elements) be replicated three times so that when the third building block is added, the final elements are produced separately. This would be carried out as is illustrated in Scheme B. The expansion of the number of congeners within each building block set and the expansion of the number of discrete building blocks can be carried to whatever level desired to prepare arrays of any desired size or structural variability.

An alternative array construction can be carried out using a large number of congeners of several building blocks but choosing not to prepare every permutation possible (for example, two building blocks each with 30 congeners leads to 900 possible compounds). In this instance quantitative structure activity relationship techniques and statistical methods can be used to select the most desired subsets of congeners to employ in preparing a smaller array.

| SCHEME B. Construction of an Array Involving Two Coupling Reactions | | | | | | | | | |
|---|---|---|---|---|---|---|---|---|---|
| Building Block #2 | Building Block #1 (A, B, C) | | | | | | | | |
| | A | B | C | A | B | C | A | B | C |
| X | AX1 | BX1 | CX1 | AX2 | BX2 | CX2 | AX3 | BX3 | CX3 |
| Y | AY1 | BY1 | CY1 | AY2 | BY2 | CY2 | AY3 | BY3 | CY3 |
| Z | AZ1 | BZ1 | CZ1 | AZ2 | BZ2 | CZ2 | AZ3 | BZ3 | CZ3 |
| | 1 | | | 2 | | | 3 | | |
| | Building Block #3 (1, 2, 3) | | | | | | | | |

To achieve the foregoing objects and in accordance with the purpose of the invention, as embodied and broadly described herein, the invention provides an apparatus for the multiple, simultaneous synthesis of compounds comprising: (a) a plurality of reaction tubes, with each reaction tube having a filter device on its lower end; (b) a reservoir block which has a means for containing a plurality of reaction wells and receiving the filter devices on the lower ends of the plurality of reaction tubes; (c) a holder block with a plurality of apertures which correspond to the location of the plurality of reaction wells in the reservoir block and the plurality of reaction tubes; (d) a manifold located adjacent to the holder block, with the lower end of the manifold open such that the manifold may be placed on the holder block and surround the upper ends of the reaction tubes which are protruding upward through the apertures in the holder block; (e) a means for providing a sealed connection which is impermeable to gases and liquids between the holder block and the manifold and the holder block and the reservoir block; and (f) a means for fastening together the components of the apparatus. FIGS. 1–10 illustrate the components and embodiments of the apparatus.

In a second embodiment, the upper end of the manifold has a plurality of apertures which correspond in location to the apertures in the holder block. In this second embodiment, a plate which has a plurality of apertures which correspond in location to the apertures in the upper end of the manifold, and a means for providing a seal between the plate and the upper end of the manifold is provided. FIGS. 1 and 6 illustrate the components of this particular embodiment.

A further advantage of the present invention is that the apparatus provides the ability to monitor the reaction process by removal of a filtrate aliquot from the reaction well and analyze the solution-by common chromatographic methods, such as Gas Chromatography/Internal Standard (GC/ISTD), High Pressure Liquid Chromatography/Internal Standard (HPLC/ISTD) or Thin Layer Chromatography (TLC), titration, colorimetry, spectroscopic methods, and the like. Additionally, by providing a separate reaction vessel for each reaction, the apparatus allows for the integrity of the filtrates, intermediates, and compounds which are generated.

The apparatus of the present invention has the additional advantages of being constructed of materials which are chemically compatible with organic reagents, such as corrosive acids and organic solvents, required for organic reactions. The present invention has the further advantage of having the ability to provide a suitable means for the manipulations, such as agitation, heating, cooling, refluxing, and an inert atmosphere, common to organic synthesis.

Additional objectives and advantages of the invention will be set forth in part in the description that follows, and in part will be obvious from this description, or may be learned by practice of the invention. The objects and advantages of the invention may be realized and attained by means of the instrumentalities and combinations particularly pointed out in the appended claims.

BRIEF DESCRIPTION OF THE DRAWINGS

While this specification concludes with claims particularly pointing out and distinctly claiming that which is regarded as the present invention, the objects and advantages of this invention may be more readily ascertained from the following description of a preferred embodiment when read in conjunction with the accompanying drawings.

DESCRIPTION OF THE PREFERRED EMBODIMENTS

Figure 1:
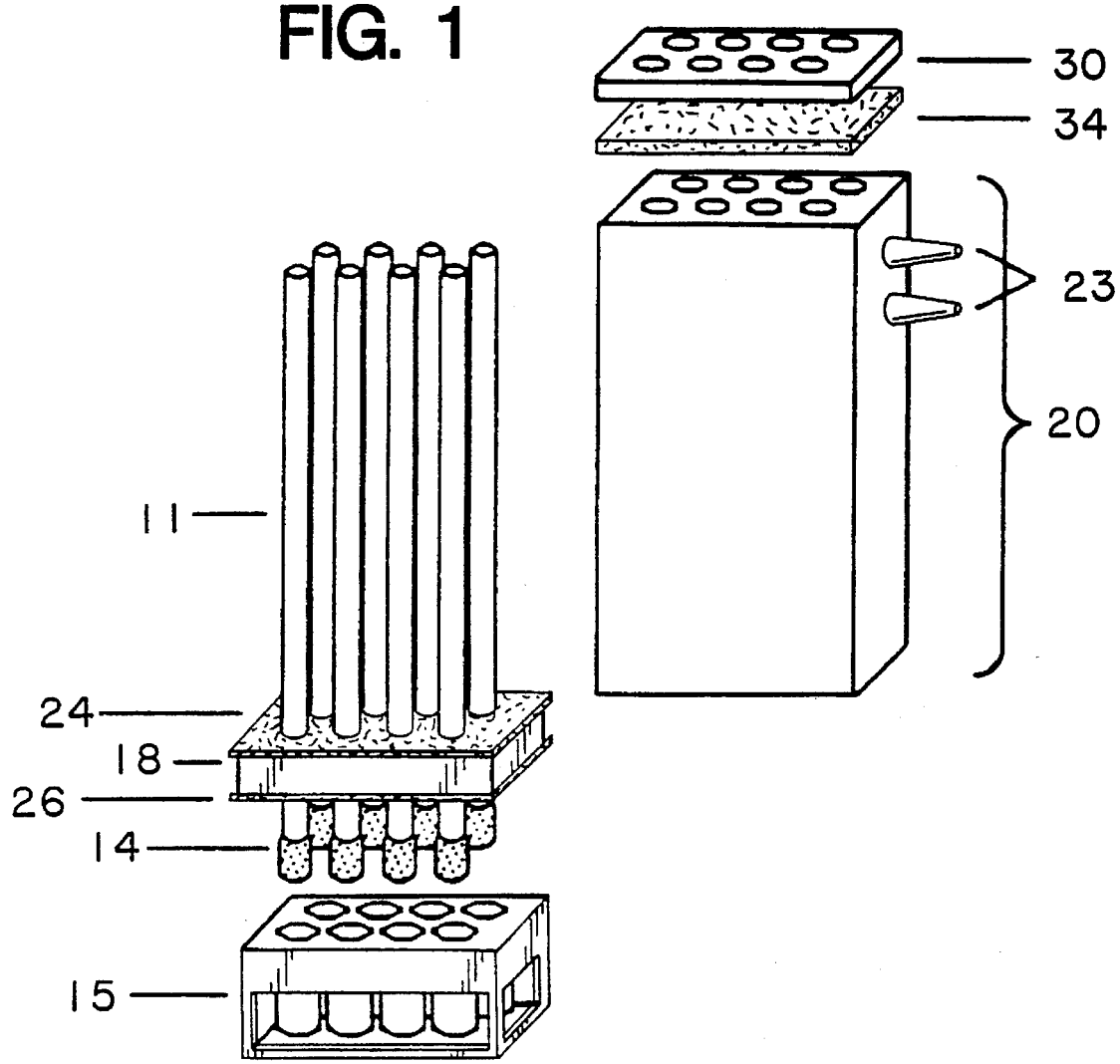
FIG. 1 is an illustration of the components of the preferred embodiment of the apparatus of the invention.

Reference will now be made in detail to the presently preferred embodiments of the invention.

The apparatus of the present invention comprises a plurality of reaction vessels. For the sake of illustration only, the accompanying drawings and description describe a device containing eight such reaction vessels, unless otherwise described. A device having a greater or lesser number of reaction vessels is entirely within the scope of the invention. Further, the apparatus is described in the accompanying drawings as having a horizontal cross-section which is rectangular in shape. An apparatus having a square or circular horizontal cross-section is also entirely within the scope of the present invention. Additionally, the apparatus may be adapted to be fully automated or semiautomated, and such adaptations are also within the scope of invention.

An initial element of the apparatus (10) as shown in FIGS. 1–6 is reaction vessels which can be any vessels capable of containing resin and organic reactants. In the preferred embodiment of the invention, the reaction vessels are a combination of reaction tubes and reaction wells. The reaction tubes are most preferably gas dispersion tubes (11). The lower ends of the reaction tubes have filters (14) and one or more pressure equalization holes (40) pierced in the reaction tubes (11) above the filters (14). The total length of each reaction tube can be from 50 to 300 mm with a preferred length of 250 mm. The upper ends of the reaction tubes may have an outside diameter of from 5 to 25 mm, with a preferred outside diameter of 8 mm. The inside diameter of the upper ends of the reaction tubes can be from 1 to 24 mm, with a preferred inside diameter of 5 mm. To allow for the materials in the reaction tube to mix with reactants, a filter (14) should be located in the lower end of the reaction tube (11). The length of the filters (14) on the lower ends of the reaction tubes can be from 1 to 300 mm, with a preferred length of 25 mm. The filters (14) on the lower ends of the reaction tubes may have an outside diameter of from 5 to 30 mm, with a preferred outside diameter of 12 mm. The filters (14) on the lower ends of the reaction tubes may have an inside diameter of from 1 to 24 mm, with a preferred inside diameter of 5 mm. Preferably, in order to allow the maximum reaction between material placed in the reaction tube and surrounding reactant, this filter (14) is preferably constructed of fritted glass. The porosity of the frit may be modified or selected to accommodate various mesh sizes of solid supports and to affect more efficient reaction mixing. The pore diameter may be from 10 to 400 μm, with a preferred pore diameter of 145 to 175 μm for 200 to 400 mesh resin. The reaction tubes, including the filters, must be constructed of a material which will not be harmed by the presence of the volatile and/or corrosive reactants which are often necessary to carry out organic chemical reactions. Such materials include glass, polytetrafluoroethylene (PTFE), stainless steel, ceramics, or alternate glasses, metals, or plastics, preferably glass. One or more (preferably one) pressure equalization holes (40) located on the reaction tube at a position above the filter and below the bottom face of the holder block provides a means to equilibrate any pressure differentials within the sealed apparatus. The position of the pressure equalization holes above the filter may be from 1 to 250 mm, with a preferred height of 20 mm above the top of the filter (14). The diameter of the pressure equalization holes must be small enough to prevent loss of resin through them or cause significant loss of air pressure during sparging. The pressure equalization holes may have a diameter from 100 to 2000 μm, with a preferred diameter of 1000 μm.

A second component of the apparatus of the present invention as shown in FIGS. 1–6 is a reservoir block (15). The reservoir block (15) contains a plurality of reaction wells (16). In a preferred embodiment, the reservoir block consists of a reservoir rack (41) which is adapted to hold at least as many removable reaction wells (16) as the number of reaction tubes (11). The reservoir rack is constructed of a material such as aluminum, stainless steel, PTFE, ceramics, or various types of plastics, glasses, or metals. The reaction wells (16) are constructed of a solid, nonporous material which is capable of withstanding the reactive components, manipulations, and pressures required for organic synthesis. Such materials include glass, stainless steel, PTFE, ceramics, and various types of plastics, metals, or glasses, preferably glass. The reaction wells (16) in the reservoir block (15) should be sufficient in number, depth and diameter to accommodate the filters (14) on the lower ends of the reaction tubes (11) with each individual reaction well (16) suitable for receiving the lower end of one reaction tube, and to simultaneously hold a quantity of reactant necessary to perform the required reactions. The reaction wells (16) should be located throughout the reservoir block (15), such that each reaction well (16) is not in direct contact with any neighboring reaction wells. The depth of the reaction well may be from 1 to 300 mm, with a preferred depth of 50 mm. The inner diameter of the reaction well may be from 7 to 100 mm, with a preferred inner diameter of 18 mm. While not necessary to fully utilize the apparatus of the present invention, in a preferred embodiment the reaction wells are constructed of a transparent material, such as glass, plexiglass, or alternate glasses or plastics, so that the reactions may be visually monitored.

A further component of the invention as shown in FIGS. 1–6 is a holder block (18) located adjacent to the reservoir block (15). A plurality of apertures (19) are located throughout the holder block (18). These apertures (19) correspond in location, and preferably in number, no the reaction wells (16) located in the reservoir block (15), such that when the holder block (18) is placed on top of the reservoir block as in FIGS. 1–6, the apertures (19) in the holder block (18) are located directly above the reaction wells (16) in the reservoir block (15). The apertures (19) in the holder block (18) must be of sufficient diameter so that the upper ends (12) of the reaction tubes (11) will pass through the apertures. The diameter of the apertures (19) must not be so large, however, that they do not closely surround and support the upper ends (12) of the reaction tubes (11). Such support allows the holder block to secure the reaction tubes so as to prevent them from torquing, wobbling, or moving vertically. The holder block also provides a means for physically handling and manipulating the plurality of reaction tubes (11) as a single unit. The holder block (18) is preferably constructed from a heat-resistant material, such as PTFE, stainless steel, ceramics, glass, or certain types of metals, glasses, or plastics, so that it will be able to withstand organic reaction conditions.

Figure 2:
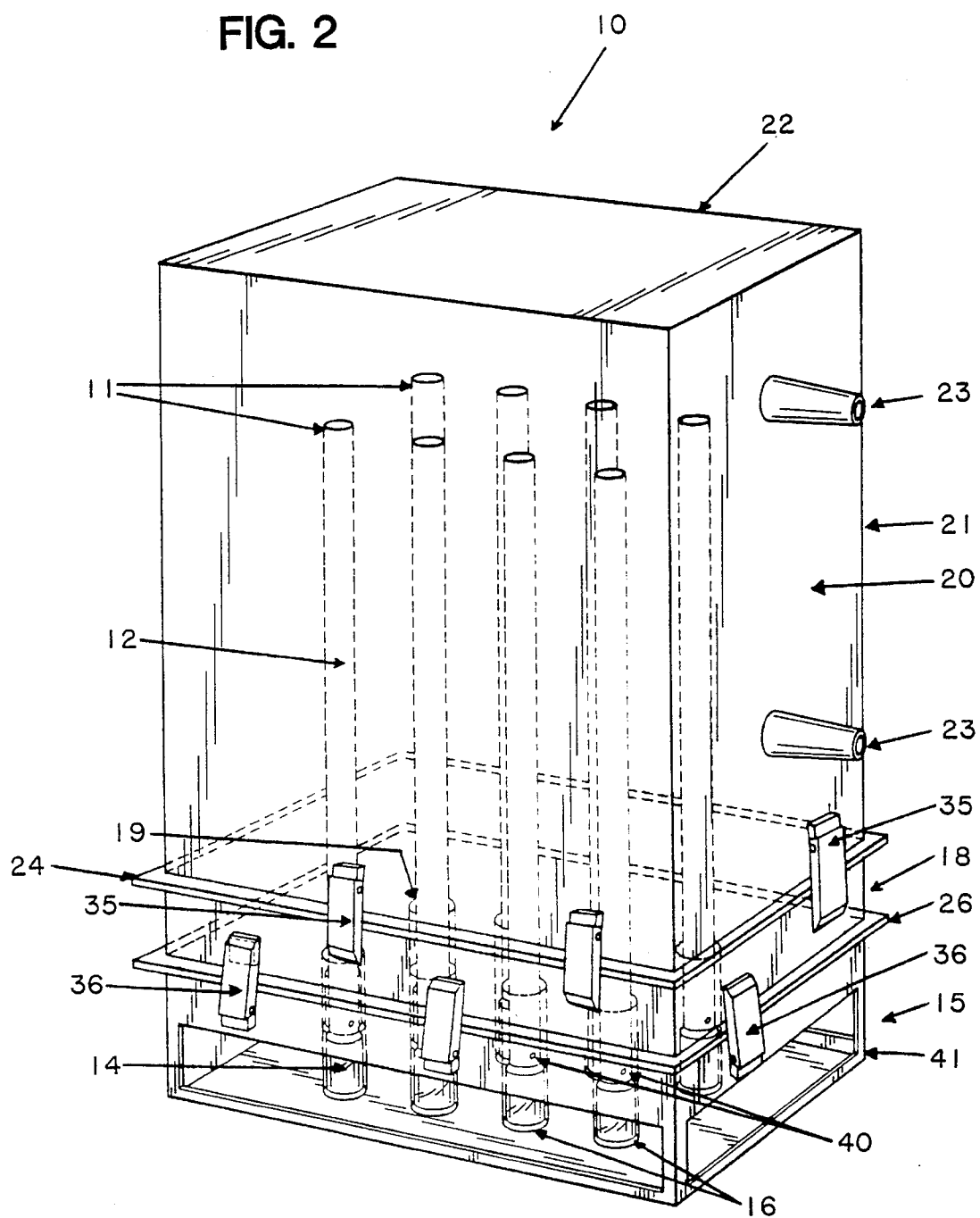
FIG. 2 is a perspective view of the components of the preferred embodiment of the apparatus of the invention.
Figure 3:
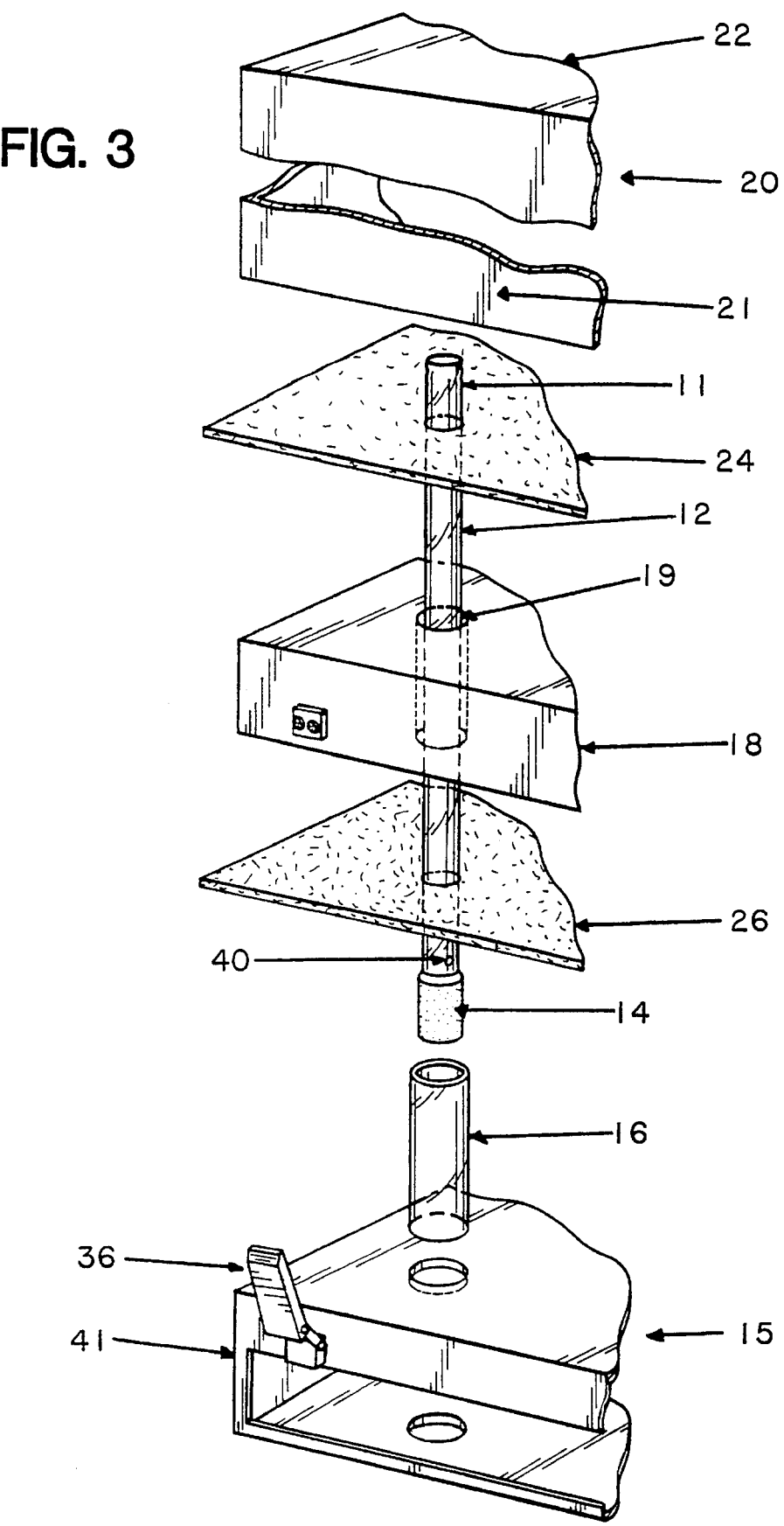
FIG. 3 is an exploded perspective view showing each of the components of the preferred embodiment of the apparatus of the invention.
Figure 4:
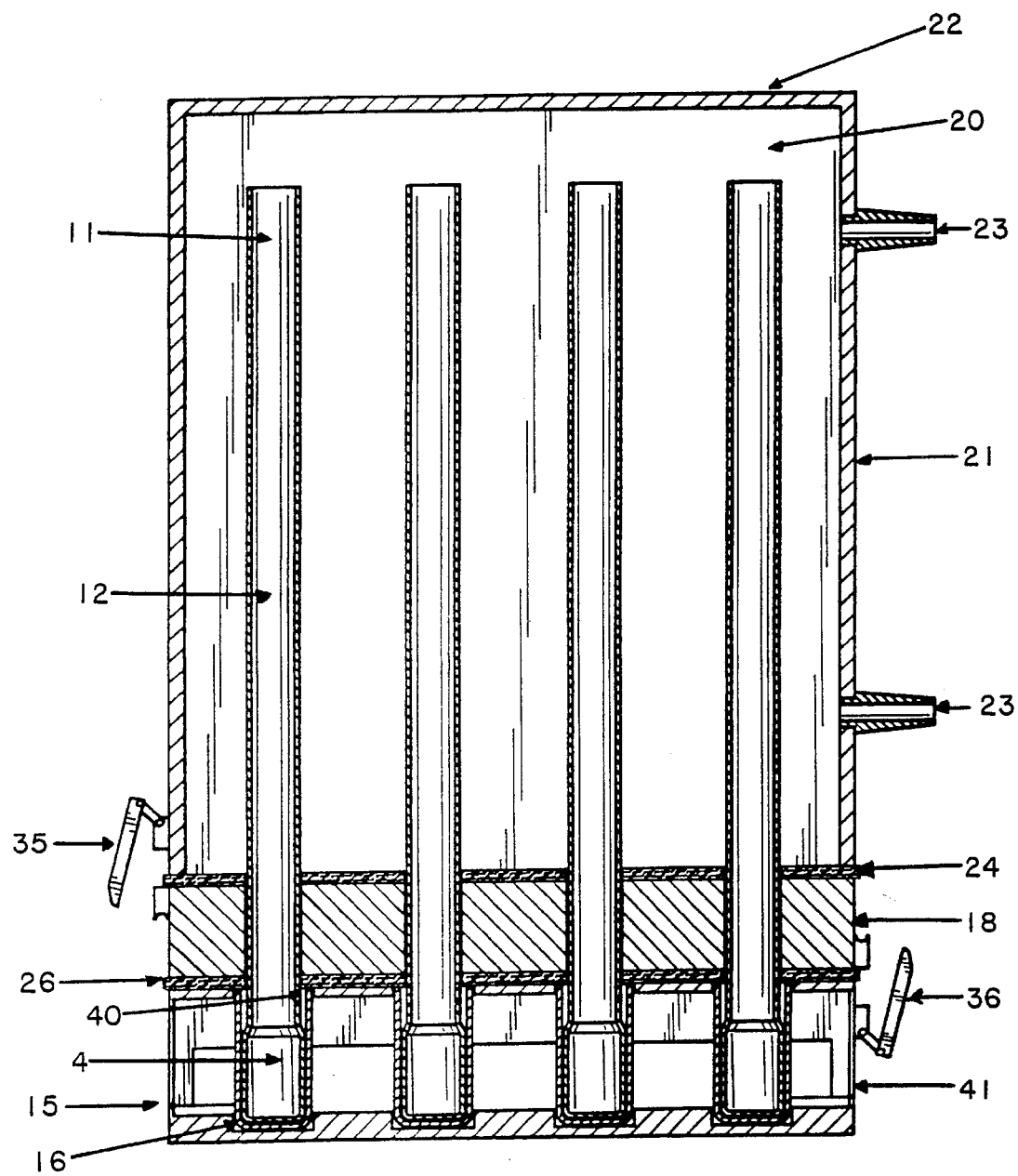
FIG. 4 is a cross-sectional view FIG. 3.
Figure 5:
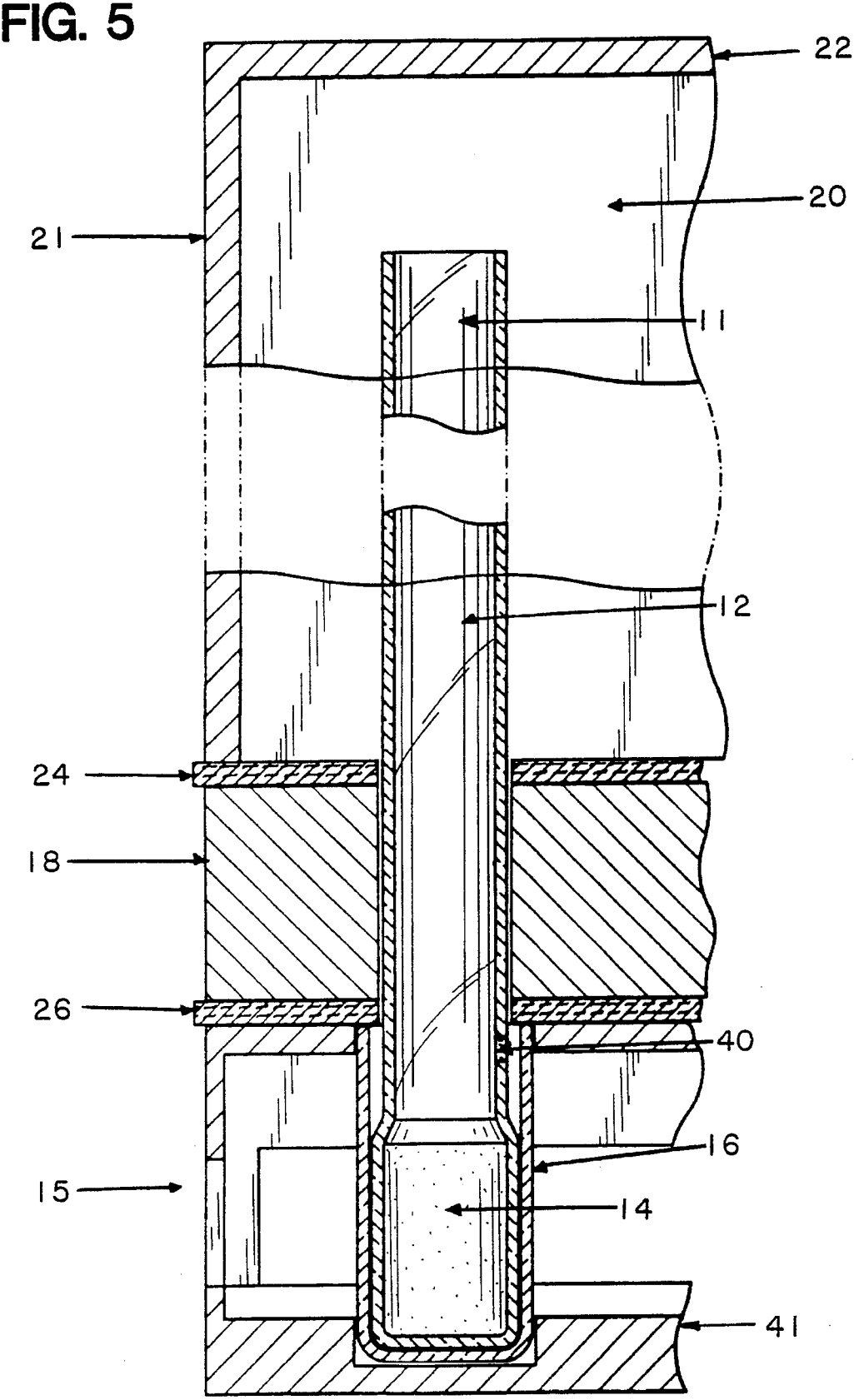
FIG. 5 is an enlarged partial cross-section of FIG. 4.

The invention further includes a manifold (20) which, as shown in FIGS. 1–6, is located adjacent to the holder block (18). The manifold (20) is in the form of a hollow chamber. Preferably, the manifold consists of four side walls (21) and a top wall (22), and has an opening on the lower end. In the preferred embodiment of the invention, the upper ends (12) of the reaction tubes, (11) after passing upward through the apertures (19) in the holder block, (18) enter and are enclosed within the manifold (20). When located adjacent to the holder block, the manifold provides an air-tight chamber which facilitates manipulations common to organic synthesis. In a preferred embodiment, the manifold (20) will have a plurality of ports (23), preferably two, located on at least one of the side walls (21) of the manifold (20). These ports may be aligned in any configuration and can be adapted to perform as inlet and outlet ports so that gaseous and/or liquid materials may be introduced into and recycled out of the manifold. The ports (23) allow control over the atmosphere within the manifold (20) and provide a means to sparge the reaction tubes (11). While not necessary to fully utilize the apparatus of the present invention, in a preferred embodiment the manifold is constructed of a transparent material, such as glass, plexiglass, or alternate glasses or plastics, so that the reactions may be visually monitored. FIG. 3 illustrates the interface of the manifold (20) and the holder block (18), which in the preferred embodiment of the invention contains a first gasket or plurality of gaskets (24) placed between the holder block and the manifold. Such placement of a first gasket(s) creates a sealing effect between the manifold and the holder block in order to allow manipulations such as pressurization, inert atmosphere, and chilled gas circulation to take place. The first gasket(s) (24) surrounds the reaction tubes (11). The first gasket(s) may be made from PTFE and/or various rubbers and/or various plastics, with preferred types of rubber being neoprene, silicone, and Viton® (copolymer of hexafluoropropylene and 1,1-difluoroenylene). In a further embodiment, a second gasket or plurality of gaskets (26) may be located at the interface of the reservoir block (15) and the holder block (18). The second gasket(s) may be made from PTFE and/or various rubbers and/or various plastics, with preferred types of rubber being neoprene, silicone, and Viton®.

Figure 6:
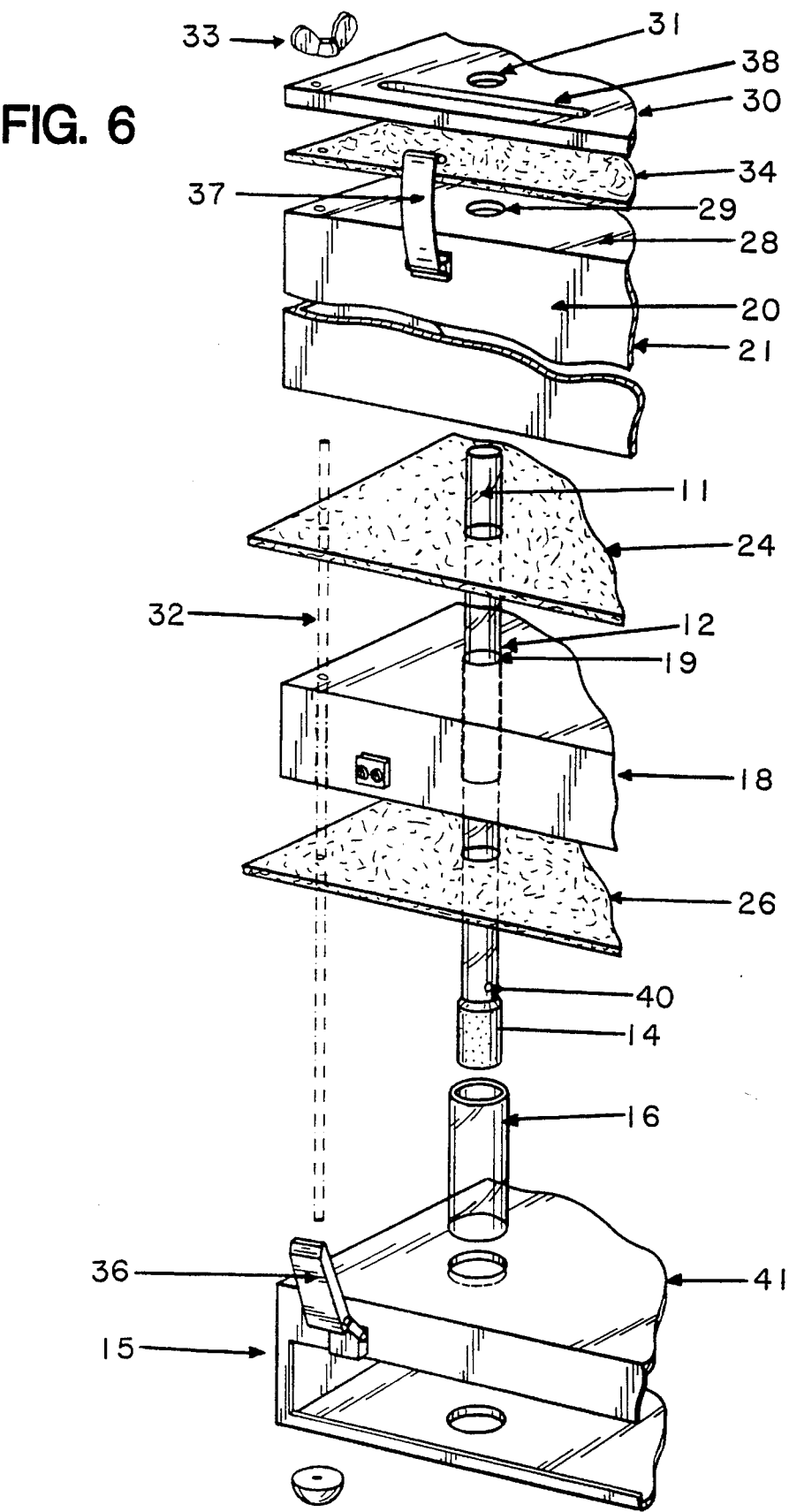
FIG. 6 is an exploded perspective view of the preferred embodiment of the invention.

FIG. 6 illustrates one further preferred embodiment of the invention. In this embodiment, the top wall of the manifold (28) contains apertures (29) which, when the manifold (20) is located on the holder block (18), correspond in number and spatial location to the apertures (19) in the holder block (18). In conjunction with this embodiment, a plate (30) with apertures (31) corresponding in number and spatial location to the apertures (29) in the top wall (28) of the manifold (20) is placed on the top wall of the manifold. A third gasket or plurality of third gaskets (34) placed between the top wall of the manifold and the plate allows the manifold (20) to remain sealed despite the apertures (29) in the top wall (28) of the manifold. In this embodiment, the third gasket(s) (34) may be made from PTFE and/or various rubbers and/or various plastics, with preferred types of rubber being neoprene, silicone, and Viton® so that it is puncturable with a needle-like object and reseals following the puncture.

A further component of the invention is a means for fastening all of the various elements together. Any means may be used so long as the elements are securely fastened together. In one embodiment, the fastening means consist of spring clips affixed to the sides of the components of the apparatus so that the elements may be releasably connected to each other. As shown in FIGS. 2–6, one or more spring clips (35) may be used for releasably connecting the manifold (20) and the holder block (18). When spring clips (35) are fastened, the manifold and the holder block may be fastened together and moved in tandem, and separated from the reservoir block (15). Such an embodiment is especially useful for removing the reaction tubes, in combination with the holder block and the manifold, from the reservoir block and draining off any excess reactant. As shown in FIG. 2, spring clips (36) are provided at the interface of the holder block (18) and the reservoir block (15) and, when fastened, allow the holder block (18) and the reservoir block (15) to be fastened together independently of the manifold (20) Spring clips (35) and spring clips (36) may all be fastened simultaneously, at which point the manifold (20), the holder block (18), and the reservoir block (15) are all tightly fastened as a single unit.

In a further preferred embodiment, illustrated in FIG. 6, the fastening means consist of a plurality of rods (32) located within the apparatus and which extend for the entire length of the apparatus, from the bottom wall of the reservoir block through the top wall of the manifold, or in a second embodiment, the plate located adjacent the top wall of the manifold. The rods (32) are preferably grooved at each end so that tighteners (33), such as wing-nuts, may be tightly screwed onto the rods so as to fasten the elements together. In a preferred embodiment, such rods are located at each of the four corners of the apparatus and additional intermediate locations dependent on the size of the apparatus.

In the embodiment illustrated in FIG. 6, a groove (38) is provided along the edge of the plate (30). Two or more spring clips (37) are attached to the side wall of the manifold (20) and snap into the grooves (38) on the upper side of the plate (30). When spring clips (37) are fastened, plate (30) and gasket(s) (34) are held tightly against the top wall (28) of the manifold (20), and allow the manifold to maintain a seal despite the presence of apertures (29). This particular embodiment is most useful when sensitive chemicals are being used in the reaction. The use of spring clips as a fastening means may be in addition to or instead of the use of the plurality of rods as earlier set forth.

Figure 7:
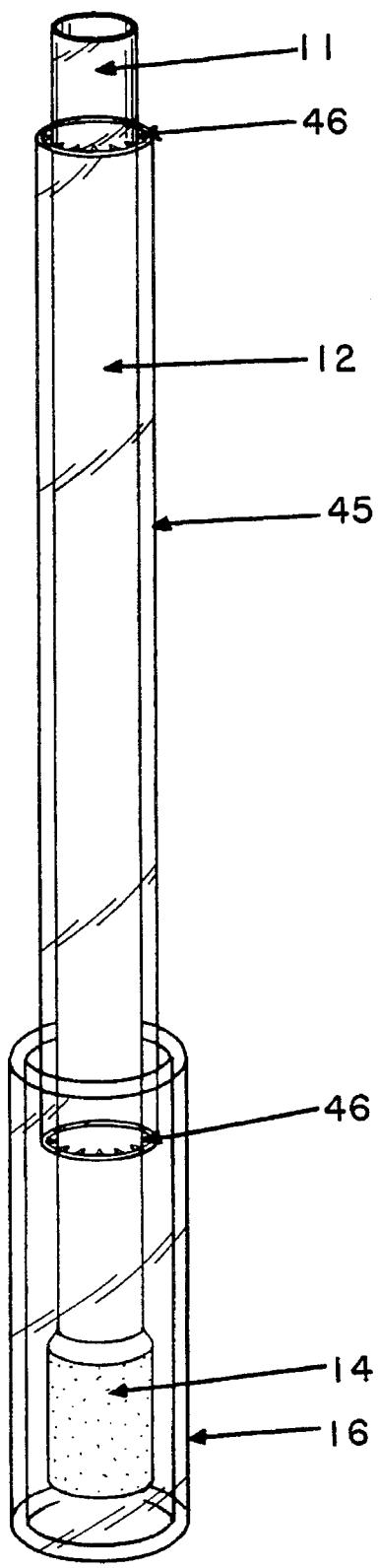
FIG. 7 is an alternative embodiment for pressure equalization by a jacketed gas dispersion tube.
Figure 8:
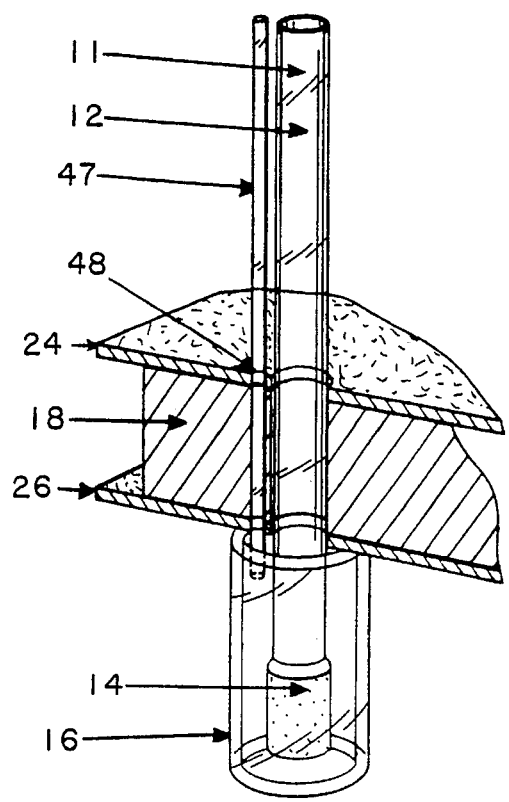
FIG. 8 is an alternative embodiment for pressure equalization by a capillary tube.

FIGS. 7 and 8 illustrate alternative embodiments for equalization of pressure between the reaction tube (11) and the reaction well (16). FIG. 7 illustrates a jacketed reaction tube (11). A hollow tube (45), constructed of a material such as glass, stainless steel, or PTFE, is placed as a jacket around the upper end of the reaction tube (11). The outside diameter of the jacket (45) may be from 8 to 36 mm, with a preferred outside diameter of 15 mm. The inside diameter of the jacket (45) may be from 6 to 33 mm, with a preferred inside diameter of 12 mm. The length of the jacket (45) can be from 1 to 300 mm, with a preferred length of 200 mm. The jacket may extend below the lower face of the holder block (18), into the reaction well (16). The length of the jacket (45) extends below the lower face of the holder block (18) by 0 to 300 mm and the reaction tube (11) is held in place by one or more protrusions (46) on the inside face of the jacket at two or more positions along the length of the jacket (45). These protrusions (46) are constructed of one or more of the following materials: glass, PTFE, or alternate plastics or glasses. Accordingly, the apertures (19) in the holder block (18) must be of sufficient diameter so that the jacket (45) will pass through the apertures.

FIG. 8 illustrates a capillary pressure release tube (47). A hollow tube, constructed of a material such as glass, stainless steel, PTFE, or alternate plastics or glasses, is placed in an aperture (48) in the holder block (18) directly adjacent to and parallel to the reaction tube (11) and within the inner diameter of the reaction well (16). The apertures (19) in the holder block (18) must be of sufficient diameter so that the capillary tubes will pass through the apertures. The diameter of the apertures (19) must not be so large, however, that they do not closely surround and support the capillary. Such support allows the holder block to secure the capillary tubes so as to prevent them from torquing, wobbling, or moving vertically. The outside diameter of the capillary tube (47) may be from 2 to 13 mm, preferably 2 mm. The inside diameter of the capillary tube (47) may be from 1 to 10 mm, preferably 1 mm. The length of the capillary tube (47) may be from 1 to 300 mm, with a preferred length of 200 mm. The lower end of the capillary tube (47) may extend below the lower face of the holder block (18), into the reaction well (16). Preferably, the lower end of the capillary tube (47) extends below the lower face of the holder block (18) by 0 to 300 mm. Accordingly, in this embodiment a second set of apertures (48) in the holder block (18) and sealing gaskets (24 and 26) must be of sufficient diameter to accommodate the capillary tube (47). The upper end of the capillary tube extends into the manifold (20).

Figure 9:
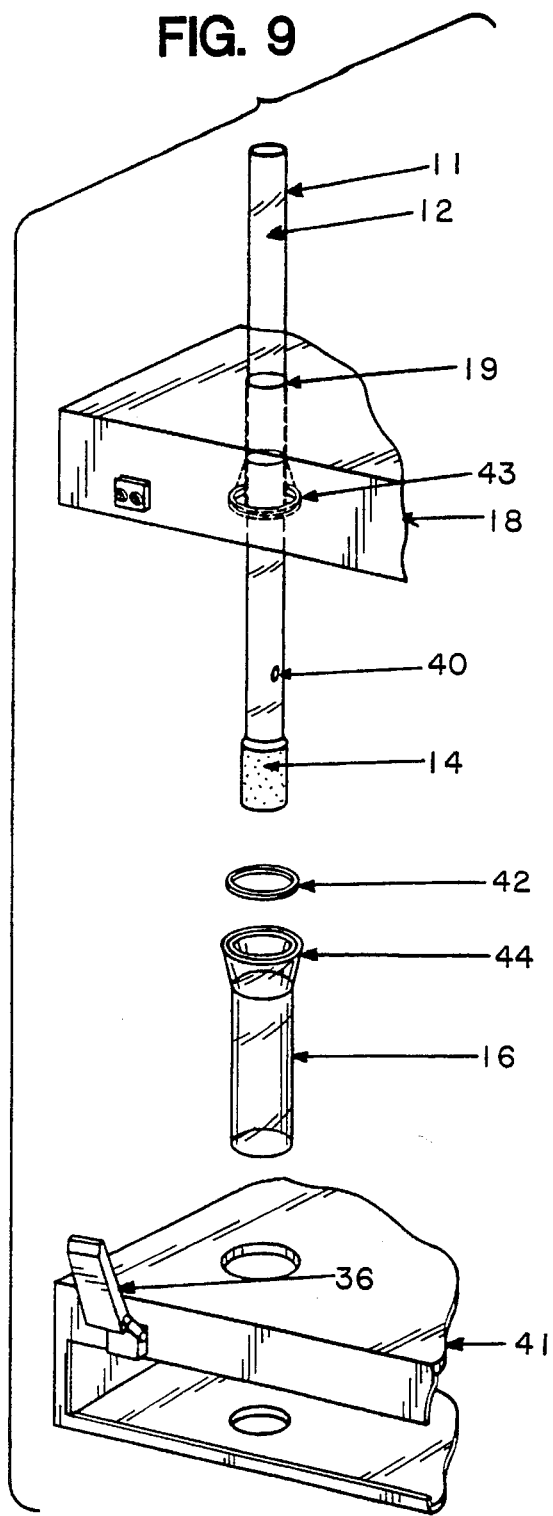
FIG. 9 is an alternative embodiment of the components for providing a gas-tight seal.

FIG. 9 illustrates an alternative embodiment for the sealing and containment of the reaction utilizing an o-shaped ring (42) seal between the reaction tube (11), the holder block (18), and the reaction well (16) to provide a greaseless, vacuum night connection. The first spherical joint (43), opening downward, tooled with a groove to accommodate the o-shaped ring (42) is fused to the outer wall of the reaction tube (11). A second spherical joint (44) having the same diameter and groove size of the first spherical joint and opening upward to accommodate the same o-shaped ring (42) is constructed at the top of the corresponding reaction well (16). The outside diameter of the first and second spherical joints (43 and 44) may be from 5 to 50 mm. The position of the first spherical joint (43) fused to the outer wall of the reaction tube (11) is above both the filter (14) and pressure equalization hole (40) and at a height necessary to adequately accommodate the glass frit within the sealed reaction well (16) when the seal is achieved. The position of the first spherical joint (43) may be from 1 to 299 mm above the top of the filter (14), with a preferred height of 25 mm above the filter, corresponding to the preferred height of the filter (14) and preferred depth of the reaction well (16) described above. The position of the corresponding second spherical joint (44) fused to the top of the reaction well (16) is also at a height necessary to adequately accommodate the filter (14) within the sealed reaction well (16) when the seal is achieved. The position of the second spherical joint (44) may be from 1 to 299 mm above the bottom of the reaction well (16), with a preferred height of 50 mm above the bottom of the reaction well (16). In this embodiment, the faces of the apertures on the lower side of the holder block (18) should be chamfered to accommodate the first spherical joint (43) attached to the outer wall of the reaction tube (11). Furthermore, the faces of the apertures on the upper side of the reservoir rack (41) should be chamfered to accommodate the second spherical joint (44) attached to the reaction well (16). The use of an o-shaped ring seal obviates the need for the second gasket (26) between the holder block (18) and the reservoir block (15).

Figure 10:
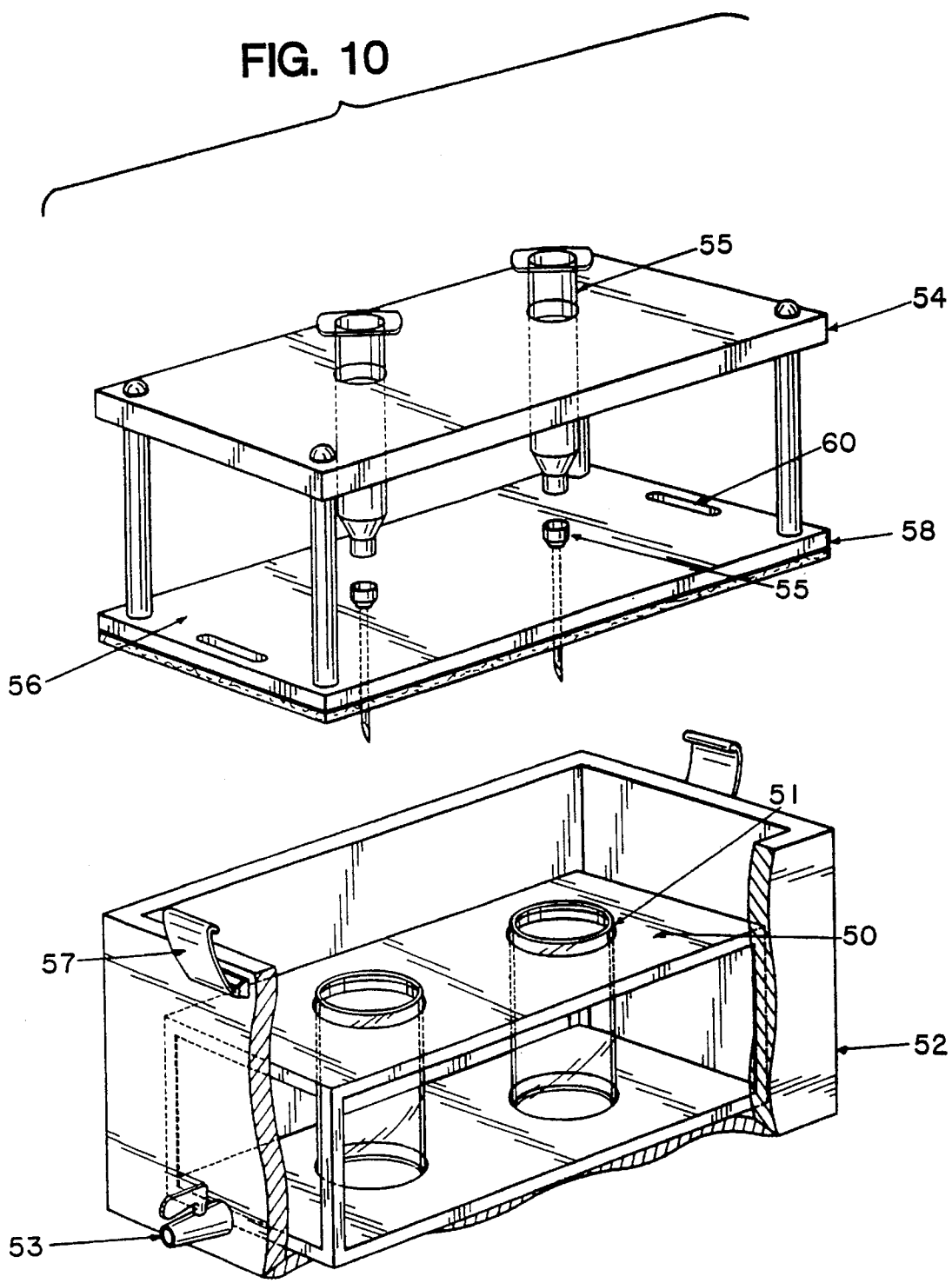
FIG. 10 is an illustration of the solid-phase extraction equipment for postcleavage manipulations.

FIG. 10 illustrates the solid phase extraction (SPE) system used for post-cleavage manipulations of the final reaction solutions. The SPE system consists of a first rack (50) having a frame which supports one or more test tubes (51), preferably the same number of test tubes as compounds synthesized in the array set forth above, for example, 8, 40, or 100 compounds. The first rack can be the same as, or compatible with, the reservoir block (15), reservoir rack (41), and reaction wells (16) described above and illustrated in FIGS. 1–6. The test tubes (51) are constructed of a solid, nonporous material such as glass, stainless steel, PTFE, ceramics, or various types of plastic. Preferably, the test tubes are constructed of glass. During operation of the SPE system, the first rack, in combination with the test tubes, is placed in a vacuum box (52). One or more valves (53) control the pressure within the vacuum box. A second rack (54) which supports one or more removable cartridges (55) fits on top of the vacuum box. The first and second racks (50 and 54) are constructed of a material such as aluminum, stainless steel, PTFE, ceramics, or various types of plastics, glasses, or metals. One or more gaskets (55) are adhered to the lower side of the base of the second rack (56) to provide a means for achieving a seal between the vacuum box and the second rack. One or more spring clips (57) are attached to the side walls of the vacuum box (52), preferably two clips are located on opposing sides, and snap into the grooves (58) in the upper side of the base of the second rack (54). When the spring clip (57) is fastened, the second rack (54) and gasket (55) are held tightly against the top wall (59) of the vacuum box (52) to maintain a seal. One or more needle-like objects (60), corresponding in number and location to the test tubes (51), are mounted in the base of the second rack (54), protrude through the gasket (55), and open into the test tubes (51). Removable cartridges (61) are used in combination with the needle-like objects (60). The lower end of each cartridge opens into the upper end of the corresponding needle-like object. The cartridges may be filled with solids or solid supports such as silica gel, drying agents, cellulose, and the like, and then eluted with solvents or reagent solutions which may be eluted through the cartridges, through the needles, and into the corresponding test tubes.

GENERAL DESCRIPTION OF EXPERIMENTAL PROCEDURE

A number of reaction tubes equal to the total number of compounds to be synthesized by the array method are loaded with 1 to 1000 mg, preferably 100 mg, of the appropriate functionalized solid support, preferably 1 to 3% cross-linked polystyrene. The individual reaction tubes are inserted into the holder block. The reaction tubes, in combination with the holder block and manifold, are inserted into the reservoir block so that each reaction tube is submerged in a volume, preferably 3 to 5 mL, of a solvent capable of swelling the polystyrene resin (such as, but not limited to, dichloromethane, chloroform, dimethylformamide (DMF), dioxane, toluene, tetrahydrofuran (THF), ethanol and the like). The polystyrene resin within the reaction tubes is preferably agitated for 15 to 30 minutes to affect swelling. Swelling times of 5 to 600 minutes, with or without agitation are also within the scope of the invention. The reaction tubes, in combination with the holder block and manifold, are removed from the reservoir block and the excess solvent within the reaction tubes is allowed to drain, preferably by gravity, although gas pressure applied to the manifold inlet (while closing the outlet) can be used to expel the solvent, if desired.

The reaction wells are emptied of solvent and the proper reactant solutions are dispensed into the new or clean reaction wells at appropriate locations in the reservoir block. If the reactant is actually one of the building blocks that is to become covalently attached to the growing compound on the solid support, the quantity of reactant is usually 1 to 100 equivalents based on the milliequivalents per gram (meq/g) loading of functionalized solid support (typically 0.1 to 1.0 meq/g for polystyrene resins) originally weighed into the reaction tube. Additional equivalents of reactants can be used if required to drive the reaction to completion in a reasonable time. The reaction tubes, in combination with the holder block and manifold, are reinserted into the reservoir block and the apparatus is fastened together. Gas flow through the manifold is initiated to provide a controlled environment, for example, nitrogen, argon, air, and the like. The gas flow may also be heated or chilled prior to flow through the manifold. Heating or cooling of the reaction wells is achieved by immersing the reservoir block in water baths, oil baths, isopropanol/dry ice baths, sand baths, and the like to perform synthetic reactions. Agitation is achieved by shaking, sonication (preferred), or magnetic stirring (within the reaction well or within the reaction tube). Reflux is achieved by circulating chilled gas through the manifold while heating the reaction wells in the reservoir block. Reactants may be injected directly into the reaction tubes through an injectable gasket on the top of the manifold. The reaction is allowed to proceed for an amount of time deemed necessary from the preliminary validation experiments or monitored by removal and quantitative analysis of filtrate aliquots from selected wells by methods such as GC/ISTD or HPLC/ISTD. If necessary, the complete assembly is allowed to return to ambient temperature, then the holder block and manifold, in combination with the reaction tubes, are detached from and raised above the reservoir block and the excess reagent solution is drained by gravity followed by gas pressure applied to the manifold inlet (while closing the outlet) to expel the excess reagents, solvents, and by-products. The resin-bound intermediate within each reaction tube is washed clean of excess retained reagents, solvents, and by-products by repetitive exposure to clean solvent(s) by one of two methods: 1) the reaction wells are filled with solvent (preferably 1–5 mL), the reaction tubes, in combination with the holder block and manifold, are immersed and agitated for 5 to 300 minutes, preferably 15 minutes, and drained by gravity followed by gas pressure applied through the manifold inlet (while closing the outlet) to expel the solvent; 2) the manifold is removed from the holder block, aliquots of solvent (preferably 5 mL) are dispensed through the top of the reaction tubes and drained by gravity through the filter into a receiving vessel such as a test tube or vial. Both of the above washing procedures are repeated 1 to 50 times (preferably 10 times), monitoring the efficiency of reagent, solvent, and byproduct removal by methods such as TLC, GC, or visualization of the wash filtrates.

The above described procedure of reacting the resin-bound compound with reagents within the reaction wells followed by removal of excess reagents, byproducts, and solvents is repeated with each successive transformation until the final or penultimate resin-bound compound is prepared.

Detachment of the final product from the solid support is achieved by immersion of the reaction tubes, in combination with the holder block and manifold, in reaction wells containing a solution of the cleavage reagent (preferably 3–5 mL). Gas flow, temperature control, agitation, and reaction monitoring are implemented as above and as desired to affect the detachment reaction. The reaction tubes, in combination with the holder block and manifold, are disassembled from the reservoir block and raised above the solution level but below the upper lip of the reaction wells and gas pressure is applied through the manifold inlet (while closing the outlet) to efficiently expel the final product solution into the reservoir wells. The spent resin in the reaction tubes is then washed 2 to 5 times as above with 3 to 5 mL of an appropriate solvent to extract (wash out) as much of the detached product as possible. The final product solutions are combined, taking care to avoid cross-mixing. The individual solutions/extracts are then manipulated as needed to isolate the final compounds. Typical manipulations include, but are not limited to, evaporation, concentration, liquid/liquid extraction, acidification, basification, neutralization or additional reactions in solution.

The final compounds are individually tested for biological activity once they are isolated. For example, the method of Sweetnam, et al, *Molecular Pharmacology* 1986;29:299 employing bovine cortical membranes as a receptor source and a radiolabeled benzodiazepine, such as Flunitrazepam, to determine competitive ligand binding to the benzodiazepine receptor (central [brain] localized) and some quantitative measure of relative binding potency such as $K_D$ or $IC_{50}$ values. Performing this type of assay serves two purposes: 1) to discover new compounds with biological activity in a given biological screening assay and 2) the development of a relationship between the structural variations contained within the series and biological potency. This second utility is known as development of a structure activity relationship (SAR). This type of assay can be done using the compounds isolated from the array synthesis for any receptor binding screen or assay (screening for receptor agonists or antagonists), enzyme functional assays (measuring competitive or noncompetitive inhibition of the catalyzed reaction), and the like.

This strategy may be used to screen for pharmaceutical agents, veterinary agents, agricultural agents, diagnostic reagents, and the like.

Typical compounds and pharmaceutical applications include: (1) nitrogen containing heterocyclic compounds; imidazopyridines having antiulcer or anxiolytic activities, dihydropyridines having calcium antagonist activity, nucleoside and nucleoside analogs having antiviral activity, indazoles having $5HT_3$ antagonist activity, piperidines having antidopamine, antiserotonin, antidepressant, or antihistamine activities, benzazepines having antiparkinsonism and antidopamine activities, indoles and condensed indoles with 5HT antagonist activities, quinolines and isoquinolines having anti-infective and antiulcer activities, pyrrolidines having anti-infective and antihypertensive activities, aminopyrimidines having antihypertensive activities, pyrrolizidines having antiarrhythmic activities, guanidines having anticancer activities, tetrazoles having antiallergenic; (2) oxygen containing heterocycles; benzopyrans having potassium agonist and antagonist activities, coumarins having antiplatelet aggregating and antithrombotic activities, prostaglandins and prostacyclins having antiplatelet, antiulcer, labor inducing activities, psoralens having antipsoriasis activities, tetrahydrofurans and pyrans having antidiabetic activity; (3) nitrogen and sulfur containing compounds; beta-lactams and cephalosporins having anti-infective activities; (4) carbocyclic compounds; tocopherol analogs having antipsoriasis activities, vitamin D analogs having antipsoriasis activities, steroids having anti-inflammatory, bronchiodilating, antihyperplasia and antifertility activities, naphthalenes having antifungal activities, anthracene analogs having anticancer activities; (5) alicyclic compounds; polyunsaturated alkenes having antithrombotic activities, hydroxypropanolamines having adrenergic blocking activities, benzofused bicyclic amines having analgesic activities, aryl amides having anesthetic, gastroprokinetic, antidepressant, and anti-inflammatory activities; and (6) cyclic peptides and cyclic nucleotide having anti-infective and antiautoimmune activities; and the like.

In alternative uses, the apparatus and methods may be implemented without using a solid support, for example, standard solution techniques. An additional alternative use of the apparatus is for the optimization of chemical reactions, for example, reaction yields or reaction times, on solid supports or in solution. This use is accomplished by performing the same reaction in all reaction well locations but systematically determining and varying dependent reaction variables across the array. For example, the reagent concentration and/or reagent equivalency (mole percentage) can be varied from near zero to the maximum achievable with an undiluted reagent. Typically, one varies this variable from 0.001 to 25 mol. Reaction times can be varied within the array by withdrawal of the contents of the reaction well, followed by for example workup, and/or isolation, and/or purification, and/or quantitation of the final solution. Statistical experimental design strategies or quantitative structure activity relationship (QSAR) strategies may also be implemented to select a subset of locations within the original array which will provide the necessary information for final analysis and conclusions, therefore reducing the number of reactions necessary in the final array.

SYNTHESIS OF DIPEPTIDES

In the operation of the present invention, the synthesis of dipeptides is achieved using the apparatus hand applying 9-fluorenylmethyloxycarbonyl (FMOC) strategy, as taught in Meienhofer, et al, *International Journal Peptide Protein Research* 1979;13:35 and Atherton, et al, *Bioorganic Chemistry*, 1979;8:351 on a variety of commercially available polystyrene resins (see Table 1). For peptide acids the p-benzyloxy benzyl alcohol cross-linked divinylbenzene-styrene (WANG) resin, as taught in Wang, *Journal American Chemistry Society* 1973;95:1328, is utilized. Eight FMOC amino acid resins including phenylalanine, glycine, alanine, isoleucine, leucine, proline, valine, and tryptophan are deprotected, reacted with either FMOC alanine or FMOC isoleucine, deprotected again, then cleaved from the resin to generate 16 discrete dipeptides. A total of 3 to 20 mg (28–85%) of each crude dipeptide is isolated as the trifluoroacetic acid (TFA) salt and analyzed by HPLC, mass spectroscopy (MS), and proton nuclear magnetic resonance spectroscopy ($^1$H NMR) (see Table 1).

SYNTHESIS OF HYDANTOINS

The synthesis of an array of 40 hydantoins, including phenytoin, is achieved using the apparatus described herein. Five samples of eight FMOC or BOC protected amino acid resins (phenylalanine, glycine, isoleucine, leucine, alanine, valine, tryptophan, and 2,2-diphenylglycine) are deprotected then separately reacted with five isocyanates (trimethylsilyl, n-butyl, allyl, 2-trifluorotolyl, or 4-methoxyphenyl isocyanate) followed by treatment with aqueous 6N hydrochloric acid (HCl) to generate 40 discrete hydantoins (see Scheme 2 and Table 2).

The synthesis of 40 hydantoins in an array illustrates a standard protocol for a typical parallel array synthesis. In this example, a robotic sample processor (Tecan® 5032) is used for every liquid sample handling step. Some of the key features which demonstrate the strengths, flexibility and scope of the method and apparatus are highlighted below. Forty BOC or FMOC protected resin-bound amino acids are weighed into the reaction tubes, assembled in the apparatus, and simultaneously deprotected employing GC/ISTD calibration methods to determine the completion of the FMOC deprotection reactions. The ability to simultaneously perform different reactions with vastly different reagents (for example, piperidine, DMF and TFA) further demonstrates the flexibility of the apparatus. Residual solvents, reactants, or byproducts are removed by wash cycles which include submersion and sonication of the reaction tubes in a series of solvents, followed by robotic spotting of the filtrates on a TLC plate and observation of the results under ultraviolet (UV) light to insure the thoroughness of the wash cycles. Following the wash cycles, the resin-bound amines are reacted with the desired isocyanates in DMF. Again, GC/ISTD calibration methods are used to quantitatively monitor the uptake of the isocyanates. After washing, the resin-bound ureas are cyclized by heating in aqueous 6N HCl to produce the desired hydantoins. Following the HCl treatment, the spent resins in the reaction tubes are washed with methanol to completely extract the hydantoins from the resins. All filtrates are combined, concentrated on a commercial centrifugal vacuum system (SpeedVac®), weighed, and analyzed to yield the expected hydantoins, in all but one example (see Table 2). A total of 0 to 11.5 mg corresponding to 0 to 81% yield of each crude hydantoin is isolated and analyzed by TLC, MS, and $^1$H NMR.

SYNTHESIS OF BENZODIAZEPINES AND BIOLOGICAL TESTING

The investigation of an array synthesis of benzodiazepines as potential targets was prompted by a brief communication by Camps, et al, *Anales De Quimica* 1974;70:848 who reported a one-step synthesis of several benzodiazepines starting with a resin-bound amino acid. A two-step route is outlined in Scheme 3. The first step in the sequence is the formation of an imine between a resin-bound amino acid and a 2-aminobenzophenone. Initially, a number of condensation methods were explored, but all proved unsatisfactory. Replacement of the imine condensation with a transimination reaction, as taught by O'Donnell and Polt, *Journal Organic Chemistry* 1982;47:2663, to form a mixture of E and Z imine isomers proved satisfactory. The resin-bound amino acid imines are then converted to the corresponding benzodiazepines by heating in TFA.

The synthesis of 40 benzodiazepines in the array is similar to that outlined for the dipeptides and hydantoins with several modifications, which demonstrate the flexibility of both the method and the apparatus (see Scheme 3 and Table 3). Five amino acid Merrifield resins (alanine, glycine, 2-bromobenzyloxycarbonyl-tyrosine, tryptophan, and valine) as their TFA salts are separately reacted with eight 2-aminobenzophenone imines. The reactions are not monitored, but are reacted long enough to accommodate the slowest example (valine resin with N-isopropyl 2-amino-4-methylbenzophenone imine) based on previous validation studies. Following wash cycles to extract the unreacted imine, the resin bound imines are heated in TFA for a time sufficient to ensure cyclization of the slowest examples (imines of N-methyl 2-amino- 5-nitrobenzophenone), while minimizing decomposition of the tryptophan derived benzodiazepines. When the reaction is complete, the spent resins in the reaction tubes are washed and the combined filtrates concentrated to dryness. In this case, an aqueous bicarbonate work-up is implemented (utilizing the Tecan® 5032 robotic sample processor) to remove residual TFA. For each reaction tube the corresponding organic extracts are combined, dried, and concentrated to yield the expected benzodiazepines in all but one example (see Table 3). The 40 (39 desired) products are characterized by TLC, $^1$H-NMR, and MS. The crude yields range from 7 to >100% and the estimated purities from NMR and TLC are greater than 60% in most cases.

To verify that the compounds produced could be used directly in a biological assay, the crude benzodiazepines are tested for activity in a benzodiazepine receptor binding assay without further purification. (The assay was performed using the commercially available NovaScreen® assay system contracted by Scios-Nova Pharmaceutical Corp., Baltimore, Md., whereby bovine cortical membrane preparations were used as the source of receptor and the radioligand employed was [$^3$H]Flunitrazipam while the positive control was Clonazepam.) The calculated $IC_{50}$'s from three concentrations (average of two determinations) for the individual compounds are shown in Table 3.

The following nonlimiting examples are offered by way of illustration and are not intended to limit the invention in any manner.

EXAMPLE 1

Synthesis of Dipeptides

The synthesis of 16 dipeptides is summarized in Table 1.

101 to 153 mg each of eight FMOC protected amino acids (phenylalanine, glycine, alanine, isoleucine, leucine, proline, valine, and tryptophan) on a commercially available WANG resin (loading= 0.37–0.60 meq/g, 200–400 mesh) was measured into each of 16 gas dispersion tubes (reaction tubes). The reaction tubes were fitted into the holder block with two gaskets, one above and one below the holder block. The array of reaction tubes was fitted into a matching array of reaction wells in an appropriate reservoir block, in this case a test tube rack, and 3 mL of DMF was dispensed through the aperture at the top of the reaction tubes to wash any residual resin to the bottom of the glass frit. The manifold was fitted over the holder block and a nitrogen atmosphere was initiated through the ports on the manifold. The apparatus was then agitated in a sonic bath for 15 minutes to swell the resin support in preparation for the first reaction. Following swelling of the resin, the holder block and the manifold, in combination with the reaction tubes, were raised above the reservoir block and the reaction tubes were allowed to drain by gravity.

To deprotect the FMOC amino acids, the reaction tubes were submerged in reaction wells containing 2 mL of a solution of 22% piperidine in DMF (v/v) with an internal standard (e.g., anthracene at 1.97 mg/mL). The apparatus was fastened together with clamps and agitated in a sonic bath for 2 hours, while maintaining a positive nitrogen flow through the manifold. The reaction progress was monitored by removing a sample of the filtrate (10–100 µl) and analyzing for the FMOC-piperidine adduct and dibenzofulvene by GC/ISTD calibration methods. At the end of the reaction, the holder block and the manifold, in combination with the reaction tubes, were raised above the reservoir block and the reaction tubes were allowed to drain by gravity, then sparged with nitrogen. The reaction tubes were sparged by introducing nitrogen into one port of the manifold and closing off the second port.

The reaction tubes were subjected to a series of wash cycles to remove residual solvents, reagents, and byproducts. A standard protocol included sequentially submerging the reaction tubes in 2 to 5 mL each of 2×DMF, 2×methanol, 2×water, 2×water:dioxane (1:1), 2×dioxane, and 2×DMF, followed by agitation by sonication for 10 to 15 minutes, and finally draining by gravity and nitrogen sparge. The efficiency of the wash cycles was monitored by TLC or GC/ISTD of the wash filtrates.

In order to couple the FMOC amino acids, the following DMF solutions were sequentially admixed in two 8-unit reservoir blocks, to generate the activated esters: 1.0 mL of 0.46M FMOC alanine or FMOC isoleucine, 0.5 mL of 1.02M Benzotriazol-1-yloxy-tris-(dimethylamino)-phosphonium hexafluorophosphate (BOP), 1.0 mL of 1.02M N-Hydroxybenzotriazole (HOBT), and 0.5 mL of 1.84M N-methylmorpholine. The apparatus was assembled as above and agitated on a rotational platform shaker for 18 hours, while maintaining a positive nitrogen flow through the manifold. The reaction progress was monitored by removing a sample of the resin following the wash cycles and colorometrically analyzing for primary amines (Bromophenol blue or Kaiser/Ninhydrin). At the end of the reaction, the holder block and the manifold, in combination with the reaction tubes, were raised above the reservoir block and the reaction tubes were allowed to drain by gravity then sparged with nitrogen.

The reaction tubes were subjected to the same series of wash cycles as previously set forth.

The deprotection of the above formed FMOC protected dipeptides was repeated following the same procedure as previously set forth.

The reaction tubes were again subjected to the same series of wash cycles as previously set forth.

In order to cleave the product from the solid support, the reaction tubes were submerged in reaction wells containing 3 mL of a solution of anisole:TFA (5:95). The apparatus was sealed with clamps and agitated in a sonic bath, while maintaining a positive nitrogen flow through the manifold. After 3 hours, the holder block and the manifold, in combination with the reaction tubes, were raised above the reservoir block and the reaction tubes were allowed to drain by gravity then sparged with nitrogen.

To isolate and purify the products, a holder block was fitted with disposable glass pipers which were submerged in the TFA filtrates. The filtrates were concentrated in a well-ventilated hood or glove box fitted with a scrubber by initiating and maintaining a positive, subsurface nitrogen flow through the manifold. The TFA salt was dissolved in 2 mL of water and extracted with 2 mL of ethyl acetate. The reaction reservoirs were vortexed to affect efficient extraction and the upper organic layer was withdrawn via syringe. The extraction cycle was repeated until the organic layer contained no residues as determined by TLC or GC/ISTD (3 times). The aqueous layers were concentrated on a Speed-Vac® in tared vials. The dipeptides generated in the apparatus including, alanylphenylalanine; alanylglycine; alanylisoleucine; alanylleucine; alanylalanine; alanylproline; alanylvaline; alanyltryptophan; isoleucylphenylalanine; isoleucylglycine; isoleucylisoleucine; isoleucylleucine; isoleucylalanine; isoleucylproline; isoleucylvaline; and isoleucyltryptophan, are set forth in Table 1.

EXAMPLE 2

Synthesis Of Hydantoins

The synthesis of 40 hydantoins is summarized in Scheme 2 and Table 2.

95 to 105 mg each of seven FMOC protected amino acids (phenylalanine, glycine, isoleucine, leucine, alanine, valine, and tryptophan) on a commercially available WANG resin (loading=0.37 to 0.60 meq/g, 200 to 400 mesh) and 95 to 105 mg of BOC protected diphenylglycine loaded on a commercially available cross-linked hydroxymethyl divinylbenzene-styrene resin (loading=1.04 meq/g, 200–400 mesh) was measured into 40 reaction tubes. The apparatus was assembled, swelled with 4 mL of DMF, and drained as set forth in Example 1.

To deprotect the FMOC amino acids, the appropriate reaction tubes were submerged in reaction wells containing 3 mL of a solution of 25% piperidine in DMF (v/v) with an internal standard (anthracene at 1.74 mg/mL). To deprotect the BOC amino acids the appropriate reaction tubes are submerged in wells containing 3 mL of 50% TFA/DMF. The apparatus was assembled as set forth in Example 1 and agitated in a sonic bath while maintaining a positive nitrogen flow through the manifold. The reaction progress was monitored by removing a sample of the filtrate (e.g. 10–100 μl) and analyzing for the FMOC-piperidine adduct and dibenzofulvene by GC/ISTD calibration methods. The reaction was complete after 6 hours in a sonic bath. At the end of the reaction, the reaction tube array was drained and sparged as set forth in Example 1.

The reaction tubes were subjected to the standard wash cycle set forth in Example 1.

To facilitate urea formation, the appropriate reaction tubes were submerged in reaction wells containing 3 mL of a solution of 0.19 to 0.23M isocyanate (trimethylsilyl isocyanate, butyl isocyanate, allyl isocyanate, trifluoro-o-tolyl isocyanate, and 4-methoxyphenyl isocyanate) in DMF, containing an internal standard (e.g., anthracene at 1.89–2.00 mg/mL). The apparatus was sealed as set forth in Example 1 and agitated in a sonic bath for 6 hours, while maintaining a positive nitrogen flow through the manifold. The reaction progress was monitored by removing a sample of the filtrate (10–100 μl), derivatization with an appropriate amine or alcohol, and analysis by GC/ISTD calibration methods. At the end of the reaction, the reaction tube array was drained and sparged as set forth in Example 1.

The reaction tubes were subjected to the standard wash cycle set forth in Example 1.

To facilitate cleavage of the final product from the solid support, the reaction tubes, in combination with the holder block and manifold, were submerged in reaction wells containing 3 mL each of 6N HCl. The apparatus was sealed with clamps and submerged in an oil bath (at 105° C.) and heated at 85° to 100° C. while maintaining a positive chilled nitrogen flow through the manifold. (The chilled nitrogen flow through the manifold was affected by submersion of the nitrogen inlet tubing in an isopropanol/dry ice bath.) After 2 hours, the reaction tube array was cooled, drained and sparged as set forth in Example 1.

To isolate and purify the products, the reaction tubes, in combination with the holder block and manifold, were submerged in reaction wells containing 3 mL each of methanol. The apparatus was agitated in a sonic bath for 10 to 15 minutes to extract the hydantoins from the resins then drained by gravity and nitrogen sparge. The methanol extraction protocol was repeated until the filtrates were free of any organic components as determined by TLC (4 times). The HCl and methanol filtrates were concentrated on a Speed-Vac® in tared vials to afford 39 of the 40 desired hydantoins. The hydantoins generated in the apparatus, including: 5-methyl-2,4-imidazolidinedione; 5-(phenylmethyl)- 2,4-imidazolidinedione; 2,4-imidazolidinedione; 5-(1-methylpropyl)-2,4-imidazolidinedione; 5-(2-methylpropyl)-2,4-imidazolidinedione; 5-(1-methylethyl)-2,4-imidazolidinedione; 5-(1H-indol- 2-ylmethyl)-2,4-imidazolidinedione; 5,5-diphenyl- 2,4-imidazolidinedione; 3-butyl-5-methyl- 2,4-imidazolidinedione; 3-butyl-5-(phenylmethyl)- 2,4-imidazolidinedione; 3-butyl-2,4-imidazolidinedione, 3-butyl-5-(1-methylpropyl)-2,4-imidazolidinedione; 3-butyl-5-(2-methylpropyl)-2,4-imidazolidinedione; 3-butyl-5-(1-methylethyl)-2,4-imidazolidinedione; 3-butyl-5-(1H-indol-2-ylmethyl)-2,4-imidazolidinedione; 3-butyl-5,5-diphenyl-2,4-imidazolidinedione; 5-methyl- 3-(2-propenyl)-2,4-imidazolidinedione; 5-(phenylmethyl)- 3-(2-propenyl)-2,4-imidazolidinedione; 3-(2-propenyl)-2,4-imidazolidinedione; 5-(1-methylpropyl)-3-(2-propenyl)-2,4-imidazolidinedione; 5-(2-methylpropyl)-3-(2-propenyl)- 2,4-imidazolidinedione; 5-(1-methylethyl)- 3-(2-propenyl)-2,4-imidazolidinedione; 5-(1H-indol- 2-ylmethyl)-3-(2-propenyl)-2,4-imidazolidinedione; 5,5-diphenyl-3-(2-propenyl)-2,4-imidazolidinedione; 5-methyl-3-[2-(trifluoromethyl)phenyl]- 2,4-imidazolidinedione; 5-(phenylmethyl)- 3-[2-(trifluoromethyl)phenyl]-2,4-imidazolidinedione; 3-[2-(trifluoromethyl)phenyl]-2,4-imidazolidinedione; 5-(1-methylpropyl)-3-[2-(trifluoromethyl)phenyl]- 2,4-imidazolidinedione; 5-(2-methylpropyl)- 3-[2-(trifluoromethyl)phenyl]-2,4-imidazolidinedione; 5-(1-methylethyl)-3-[2-(trifluoromethyl)phenyl]- 2,4-imidazolidinedione; 5-(1H-indol-2-ylmethyl)- 3-[2-(trifluoromethyl)phenyl]-2,4-imidazolidinedione; 5,5-diphenyl-3-[2-(trifluoromethyl)phenyl]- 2,4-imidazolidinedione; 3-(4-methoxyphenyl)-5-methyl- 2,4-imidazolidinedione; 3-(4-methoxyphenyl)-5-(phenylmethyl)-2,4-imidazolidinedione; 3-(4-methoxyphenyl)-2,4-imidazolidinedione; 3-(4-methoxyphenyl)-5-(1-methylpropyl)-2,4-imidazolidinedione; 3-(4-methoxyphenyl)-5-(2-methylpropyl)- 2,4-imidazolidinedione; 3-(4-methoxyphenyl)- 5-(1-methylethyl)-2,4-imidazolidinedione; 5-(1H-indol- 2-ylmethyl)-3-(4-methoxyphenyl)-2,4-imidazolidinedione; 3-(4-methoxyphenyl)-5,5-diphenyl- 2,4-imidazolidinedione; are set forth in Table 2.

EXAMPLE 3

Synthesis of Benzodiazepines

The synthesis of 40 benzodiazepines is summarized in Scheme 3 and Table 3.

Five commercially available BOC amino acid Merrifield resins (alanine, glycine, 2-bromobenzyloxy carbonyl-tyrosine, tryptophan, and valine; 0.57–0.89 meq/g, 200–400 mesh) were deprotected in bulk (1–5 g) instead of within the apparatus, using TFA:CH$_2$Cl$_2$ (1:1) at room temperature overnight. After washing with dioxane and CH$_2$Cl$_2$, the resins were dried under vacuum and used directly.

99 to 107 mg of each amino acid resin prepared above, as its TFA salt, was loaded into 40 reaction tubes. The apparatus was assembled, swelled with 3 mL of CH$_2$Cl$_2$, and drained as set forth in Example 1. The appropriate reaction tubes are submerged in reaction wells containing a solution of the appropriate 2-aminobenzophenoneimines (3–6 eq) in 3 mL of dichloroethane (see Scheme 2). The apparatus was sealed as set forth in Example 1 and heated at 60° C. (oil bath temp.), while maintaining a positive chilled nitrogen flow through the manifold. In this case the reactions were not monitored, but were reacted for sufficient time (24 hours) to drive the slowest reaction (valine resin with N-isopropyl 2-amino-4-methyl benzophenone imine) to completion based on earlier validation studies. The reaction tube array was allowed to cool and then drained and sparged as set forth in Example 1.

In this example, the reaction tubes were washed by adding 4 mL portions of $CH_2Cl_2$ through the top of each reaction tube repeatedly (12 times) until the washes were no longer colored (indicating the absence of 2-amino benzophenone imine or its corresponding ketone from hydrolysis).

The reaction tube array was then sparged as set forth in Example 1 and the reaction tubes are submerged in reaction wells containing 3 mL of 100% TFA. The apparatus is sealed as set forth in Example 1 and heated at 60° C. (oil bath temp.) for 20 hours, while maintaining a positive chilled nitrogen flow through the manifold as set forth in Example 2. Again, the reactions were not monitored, but were allowed to react for a time sufficient to ensure conversion of the slowest reactions (N-methyl 2-amino-5-nitro benzophenone imine), while minimizing decomposition of the tryptophan derived benzodiazepines. The reaction tube array was allowed to cool and then drained as set forth in Example 1.

The reaction tubes are then washed as above with 3×2 mL portions of $CH_2Cl_2$.

The appropriate washes are then combined and evaporated under a stream of nitrogen as set forth in Example 1, except in this case the piper tips were maintained above the surface of the liquid. A simple extraction procedure was implemented using the Tecan® robot. The residues from evaporation were dissolved in 3 mL $CH_2Cl_2$ and mixed with 3 mL saturated sodium bicarbonate. The organic phase was withdrawn and the aqueous layer was extracted twice more with 1.5 mL of $CH_2Cl_2$. The combined organic extracts were dried with $MgSO_4$, filtered, and concentrated as before to yield the expected benzodiazepines in all but one example (see Table 3). The 40 (39 desired) products were characterized by TLC, $^1H$-NMR, and MS. The crude yields range from 4 to >100% and the estimated purities from NMR and TLC are greater than 60% in most cases. The desired products including: 1,3-dihydro-3-methyl-5-phenyl-2H-1,4-benzodiazepin-2-one; 7-chloro-1,3-dihydro-3-methyl-5-phenyl-2H-1,4-benzodiazepin-2-one; 1,3-dihydro-5-(4-methoxyphenyl)-3-methyl-2H-1,4-benzodiazepin-2-one; 1,3-dihydro-3-methyl-7-nitro-5-phenyl-2H-1,4-benzodiazepin-2-one; 1,3-dihydro-1-isopropyl-3,6-dimethyl-2H-1,4-benzodiazepin-2-one; 7-nitro-1,3-dihydro-1,3-dimethyl-5-phenyl-2H-1,4-benzodiazepin-2-one; 5-cyclohexyl-1,3-dihydro-3-methyl-2H-1,4-benzodiazepin-2-one; 1,3-dihydro-3-methyl-5-(2-thienyl)-2H-1,4-benzodiazepin-2-one; 1,3-dihydro-5-phenyl-2H-1,4-benzodiazepin-2-one; 7-chloro-1,3-dihydro-5-phenyl-2H-1,4-benzodiazepin-2-one; 1,3-dihydro-5-(4-methoxyphenyl)-2H-1,4-benzodiazepin-2-one; 1,3-dihydro-7-nitro-5-phenyl-2H-1,4-benzodiazepin-2-one; 1,3-dihydro-1-isopropyl-6-methyl-2H-1,4-benzodiazepin-2-one; 7-nitro-1,3-dihydro-1-methyl-5-phenyl-2H-1,4-benzodiazepin-2-one; 5-cyclohexyl-1,3-dihydro-2H-1,4-benzodiazepin-2-one; 1,3-dihydro-5-(2-thienyl)-2H-1,4-benzodiazepin-2-one; 1,3-dihydro-3-(4-hydroxyphenyl)-5-phenyl-2H-1,4-benzodiazepin-2-one; 7-chloro-1,3-dihydro-3-(4-hydroxyphenyl)-5-phenyl-2H-1,4-benzodiazepin-2-one; 1,3-dihydro-5-(4-methoxyphenyl)-3-(4-hydroxyphenyl)-2H-1,4-benzodiazepin-2-one; 1,3-dihydro-7-nitro-3-(4-hydroxyphenyl)-5-phenyl-2H-1,4-benzodiazepin-2-one; 1,3-dihydro-1-isopropyl-6-methyl-3-(4-hydroxyphenyl)-2H-1,4-benzodiazepin-2-one; 7-nitro-1,3-dihydro-1-methyl-3-(4-hydroxyphenyl)-5-phenyl-2H-1,4-benzodiazepin-2-one; 5-cyclohexyl-1,3-dihydro-3-(4-hydroxyphenyl)-2H-1,4-benzodiazepin-2-one; 1,3-dihydro-3-(4-hydroxyphenyl)-5-(2-thienyl)-2H-1,4-benzodiazepin-2-one; 1,3-dihydro-3-(1H-indol-2-ylmethyl)-5-phenyl-2H-1,4-benzodiazepin-2-one; 7-chloro-1,3-dihydro-3-(1H-indol-2-ylmethyl)-5-phenyl-2H-1,4-benzodiazepin-2-one; 1,3-dihydro-3-(1H-indol-2-ylmethyl)-5-(4-methoxyphenyl)-2H-1,4-benzodiazepin-2-one; 1,3-dihydro-3-(1H-indol-2-ylmethyl)-7-nitro-5-phenyl-2H-1,4-benzodiazepin-2-one; 1,3-dihydro-3-(1H-indol-2-ylmethyl)-1-isopropyl-6-methyl-2H-1,4-benzodiazepin-2-one; 7-nitro-1,3-dihydro-3-(1H-indol-2-ylmethyl)-1-methyl-5-phenyl-2H-1,4-benzodiazepin-2-one; 5-cyclohexyl-1,3-dihydro-3-(1H-indol-2-ylmethyl)-2H-1,4-benzodiazepin-2-one; 1,3-dihydro-3-(1H-indol-2-ylmethyl)-5-(2-thienyl)-2H-1,4-benzodiazepin-2-one; 1,3-dihydro-3-(1-methylethyl)-5-phenyl-2H-1,4-benzodiazepin-2-one; 7-chloro-1,3-dihydro-3-(1-methylethyl)-5-phenyl-2H-1,4-benzodiazepin-2-one; 1,3-dihydro-5-(4-methoxyphenyl)-3-(1-methylethyl)-2H-1,4-benzodiazepin-2-one; 1,3-dihydro-3-(1-methylethyl)-7-nitro-5-phenyl-2H-1,4-benzodiazepin-2-one; 1,3-dihydro-1-isopropyl-6-methyl-3-(1-methylethyl)-2H-1,4-benzodiazepin-2-one; 7-nitro-1,3-dihydro-1-methyl-3-(1-methylethyl)-5-phenyl-2H-1,4-benzodiazepin-2-one; 5-cyclohexyl-1,3-dihydro-3-(1-methylethyl)-2H-1,4-benzodiazepin-2-one; 1,3-dihydro-3-(1-methylethyl)-5-(2-thienyl)-2H-1,4-benzodiazepin-2-one; are set forth in Table 3.

EXAMPLE 4

Synthesis of Quinolones

The synthesis of 36 quinolones is summarized in Scheme 4 and Table 4.

Thirty-six gas dispersion tubes are loaded each with 100±5 mg of hydroxymethyl polystyrene resin (1% cross-linked, 1.0 meq/g, loading) and placed in the holder block. The apparatus is assembled, swelled with 3 mL of $CH_2Cl_2$, and drained as set forth in Example 1.

To three sets of 12 reaction wells within the array is added 2 mL of a 0.2M $CH_2Cl_2$ solution of either 3-(2,4,5-trifluorophenyl)-3-oxo-1-propanoic acid, 3-(2,3,4,5-tetrafluorophenyl)-3-oxo-1-propanoic acid, or 3-(2,4-dichloro-5-fluoropyridyl)-3-oxo-3-propanoic acid. An additional 1 mL of a $CH_2Cl_2$ stock solution containing 0.4M dicyclohexylcarbodiimide and 0.4M 1-hydroxybenzotriazole is added to all 36 reaction wells of the array and the appropriate reaction tubes are submerged in the corresponding reaction wells. The apparatus is sealed as set forth in Example 1 and agitated in a sonic bath for 12 hours, while maintaining a positive chilled nitrogen flow through the manifold as set forth in Example 2. At the end of the reaction, the reaction tube array is drained and sparged as set forth in Example 1.

The reaction tube array is then washed using $CH_2Cl_2$ (10 times) as set forth in Example 3.

Into every well of the array is added 3 mL of a solution of acetic anhydride/triethyl orthoformate (1:1 v/v) and the apparatus is sealed as set forth in Example 1. The apparatus is then heated at 150° C. (oil bath temp.) for 3 hours, while maintaining a positive chilled nitrogen flow through the manifold as set forth in Example 2. At the end of the reaction, the reaction tube array is drained and sparged as set forth in Example 1.

The reaction tubes are washed as set forth in Example 3, using $CH_2Cl_2$ (10 times, 3 mL.)

To three sets of 12 reaction wells within the array is added 3 mL of a t-butanol solution 0.13M in both ethyl amine and t-butoxide, or cyclopropyl amine and t-butoxide, or 2,4-difluoroaniline and t-butoxide. The apparatus is reassembled as set forth in Example 1, immersed in an oil bath (60° C.)

and heated for 12 hours as set forth in Example 3. At the end of the reaction, the reaction tube array is allowed to cool and then drained and sparged as set forth in Example 1.

The reaction tubes are then washed as set forth in Example 3, using $CH_2Cl_2$ (12 times, 3 mL.)

To four sets of nine reaction wells within the array is added 3 mL of a 0.26M acetonitrile solution of either piperazine, piperidine, N-methyl piperazine, or 3-(ethylaminomethyl)pyrrolidine. The apparatus is assembled as set forth in Example 1, and heated in an oil bath (80° C.) for 4 hours as set forth in Example 3. At the end of the reaction, the reaction tube array is allowed to cool and then drained and sparged as set forth in Example 1.

The reaction tubes are then washed as set forth in Example 3, using $CH_2Cl_2$ (12 times, 3 mL.)

The reaction tubes are submerged in reaction wells containing 3 mL of 2N NaOH in 1:1 dioxane:water. The apparatus is assembled as set forth in Example 1, and allowed to stand at room temperature for 6 hours to affect ester hydrolysis. At the end of the reaction, the reaction tube array is drained and sparged as set forth in Example 1.

The reaction tubes are then washed as set forth in Example 3, using 3×3 mL of 0.1N NaOH in dioxane:water (1:1). The filtrates are then combined and the dioxane is removed by evaporation as set forth in Example 3. The resulting aqueous solutions are acidified with 5N HCl solution and evaporated to give the 36 individual expected crude quinolones.

EXAMPLE 5

Synthesis of Keto-ureas

The synthesis of eight keto-ureas is summarized in Scheme 5 and Table 5.

100 g of Merrifield's chloromethyl polystyrene resin (1–3% cross-linked, loading=0.78 meq/g, 200–400 mesh) is heated for 20 hours at 150°–155° C. in 500 mL of DMSO with 5 eq of $NaHCO_3$ to form the resin-bound benzaldehyde. The resin is filtered and washed sequentially with excess DMSO, hot water, dioxane:water (2:1), water, dioxane, acetone, ethanol, $CH_2Cl_2$, and benzene. The dried aldehyde resin is then reacted with O-methylhydroxylamine hydrochloride (7.5 eq) and pyridine (7.8 eq) in refluxing ethanol to form the resin-bound oxime, which is washed with excess MeOH and $CH_2Cl_2$, and then directly reduced with sodium cyanoborohydride (10 eq) in EtOH saturated with HCl at room temperature for 3 hours using methyl orange as an indicator and adjusting the pH to 3.1 with additional EtOH/HCl. The resin is washed sequentially with excess MeOH, hot water, dioxane:water (1:1), dioxane, and $CH_2Cl_2$ and used directly below.

100 mg of O-Methyl hydroxylamine resin from above is measured into each of the eight gas dispersion tubes (reaction tubes). The apparatus is assembled, swelled with 3 mL of $CH_2Cl_2$, and drained as set forth in Example 1.

To facilitate coupling of the Boc-amino benzoic acids, the appropriate reaction tubes are submerged in reaction wells containing 3 mL of a solution of 0.08M diisopropylethylamine, 0.16M BOP (Benzotriazol- 1-yloxy-tris-(dimethylamino)-phosphonium hexafluorophosphate), and 0.08M Boc-amino benzoic acid (either 3-amino-4-chlorobenzoic acid or 4-amino- 3-hydroxybenzoic acid) in $CH_2Cl_2$. The apparatus is sealed as set forth in Example 1 and agitated in a sonic bath for 8 hours while maintaining a positive nitrogen flow through the manifold. At the end of the reaction, the reaction tube array is drained and sparged as set forth in Example 1.

The reaction tube array is subjected to the standard wash cycle set forth in Example 1.

The appropriate reaction tubes are submerged in reaction wells containing a solution of 4 mL of sat. HCl-Ether:dioxane (2:1). The apparatus is sealed as set forth in Example 1 and agitated in a sonic bath for 2 hours, while maintaining a positive nitrogen flow through the manifold. At the end of the reaction, the reaction tube array is drained and sparged as set forth in Example 1.

The reaction tube array is subjected to the standard wash cycle set forth in Example 1.

The appropriate reaction tubes are submerged in reaction wells containing a solution of 3 mL of 0.16M phenyl isocyanate or ethyl isocyanate in dioxane with an internal standard (e.g., anthracene at 2–4 mg/mL). The apparatus is sealed as set forth in Example 1 and agitated in a sonic bath for 6 hours, while maintaining a positive nitrogen flow through the manifold. The reaction progress is monitored by GC/ISTD as set forth in Example 1. At the end of the reaction, the reaction tube array is drained and sparged as set forth in Example 1.

The reaction tube array is subjected to the standard wash cycle set forth in Example 1.

In order to cleave the product from the solid support, the reaction tubes are submerged in reaction wells containing a solution of 3 mL of dry $CH_2Cl_2$ at −78° C. The apparatus is sealed as set forth in Example 1 and placed in an isopropanol/dry ice bath while maintaining a positive chilled nitrogen flow through the manifold. A solution of either methylmagnesium bromide 1.4M in toluene/tetrahydrofuran or phenylmagnesium bromide 1.0M in tetrahydrofuran (0.2 mL) is added to the top of the appropriate reaction tubes through the gasket at the top of the manifold and the apparatus is sonicated at −78° C. (maintained at −10° C. by circulating chilled fluid through the sonic bath). After 2 hours, 10% HCl (0.5 mL) is added to each reaction tube through the gasket at the top of the manifold and the apparatus is allowed to warm to room temperature. At the end of the reaction, the reaction tube array is drained and sparged as set forth in Example 1.

To isolate and purify the products, the reaction tubes are washed as set forth in Example 1, using 3 mL portions of methanol. The methanol extraction protocol is repeated until the filtrates are free of any organic components as determined by TLC (1–2 times). The appropriate HCl and methanol filtrates are then combined and concentrated on a Speed-Vac® in tared vials to afford eight discrete keto-ureas.

EXAMPLE 6

Synthesis of $N^2$-Substituted Hydantoins

The synthesis of eight $N^2$-substituted hydantoins is summarized in Scheme 6 and Table 6.

100 mg each of the commercially available FMOC-protected amino acids on WANG resins (FMOC-Alanine and FMOC-Phenylalanine, loading=0.37–0.60 meq/g, 200–400 mesh) are measured into two sets of four gas dispersion tubes (reaction tubes). The apparatus is assembled, swelled with 3 mL of DMF, and drained as set forth in Example 1.

To deprotect the FMOC amino acids, the appropriate reaction tubes are submerged in reaction wells containing a solution of 4 mL of 25% piperidine in DMF (v/v) containing an internal standard (anthracene at 2–4 mg/mL). The apparatus is sealed as set forth in Example 1 and agitated in a sonic bath while maintaining a positive nitrogen flow through the manifold. The reaction progress is monitored by removing a sample of the filtrate (e.g., 10–100 μL) and analyzing for the FMOC-piperidine adduct and dibenzofulvene by GC/ISTD calibration methods. At the end of the reaction, the reaction tube array is drained and sparged as set forth in Example 1.

The reaction tube array is subjected to the standard wash cycle set forth in Example 1.

The appropriate reaction tubes are submerged in reaction wells containing a solution of 4 mL of 0.10 to 0.30M acetaldehyde or benzaldehyde in dioxane containing an internal standard (e.g., anthracene at 2–4 mg/mL). The apparatus is sealed and agitated in a sonic bath for 12 hours, while maintaining a positive nitrogen flow through the manifold. The reaction progress is monitored by GC/ISTD calibration methods as set forth in Example 1. At the end of the reaction, the reaction tube array is drained and sparged as set forth in Example 1.

The reaction tube array is subjected to the standard wash cycle set forth in Example 1.

The appropriate reaction tubes are submerged in reaction wells containing a solution of 4 mL of 0.10–0.30M sodium cyanoborohydride in methanol with an indicator (e.g., methyl orange at 2–4 mg/mL). The apparatus is sealed as set forth in Example 1 and agitated in a sonic bath while maintaining a positive nitrogen flow through the manifold. The reaction progress is monitored by visually observing the color of the filtrates. When neutral or basic conditions are observed, the pH is adjusted by injection of dilute aqueous HCl into the appropriate reaction tubes through the gasket at the top of the manifold. Stabilization of pH changes indicates completion of the reduction reaction. At the end of the reaction, the reaction tube array is drained and sparged as set forth in Example 1.

The reaction tube array is subjected to the standard wash cycle set forth in Example 1.

The appropriate reaction tubes are submerged in reaction wells containing a solution of 4 mL of 0.10–0.30M trimethylsilyl isocyanate or allyl isocyanate in DMF containing an internal standard (e.g., anthracene at 2–4 mg/mL). The apparatus is sealed as set forth in Example 1 and agitated in a sonic bath for 6 hours, while maintaining a positive nitrogen flow through the manifold. The reaction progress is monitored by removing a sample of the filtrate (10–100 μL), derivatization with an appropriate amine or alcohol, and analysis by GC/ISTD calibration methods as set forth in Example 1. At the end of the reaction, the reaction tube array is drained and sparged as set forth in Example 1.

The reaction tube array is subjected to the standard wash cycle set forth in Example 1.

In order to cleave the product from the solid support, the reaction tubes are submerged in reaction wells containing a solution of 4 mL of aqueous 6N HCl. The apparatus is sealed as set forth in Example 1, placed in an oil bath and heated at 95° to 100° C. for 2 hours while maintaining a positive chilled nitrogen flow through the manifold as set forth in Example 2. At the end of the reaction, the reaction tube array is drained and sparged as set forth in Example 1.

To isolate and purify the products, the reaction tubes are washed as set forth in Example 1 using 4 mL portions of methanol. The methanol extraction protocol is repeated until the filtrates are free of any organic components as determined by TLC (1–2 times). The appropriate HCl and methanol filtrates are then combined and concentrated on a Speed-Vac® in tared vials to afford eight discrete hydantoins.

EXAMPLE 7

Synthesis of (R)-4-Benzamido-5-oxopentanoic Acids

The synthesis of 12 oxopentanoic acids is summarized in Scheme 7 and Table 7.

5 g of α-2-Trimethysilylethyl-N-BOC-glutamic acid is linked through the γ-carboxyl group to commercially available p-benzyloxybenzyl alcohol resin (loading= 1.2 meq/g, 200–400 mesh) using N,N'-diisopropylcarbodiimide (4 eq) and HOBT (2 eq) in 3 mL of DMF for 24 hours. The resulting resin is then washed with excess MeOH and $CH_2Cl_2$ and used directly below.

95 to 105 mg of the above formed resin is measured into each of 12 gas dispersion tubes (reaction tubes). The apparatus is assembled, swelled with 3 mL of dioxane, and drained as set forth in Example 1.

The reaction tubes are submerged in reaction wells containing a solution of tetrabutylammoniun fluoride (5 eq) in dioxane (3 mL) at room temperature. The apparatus is sealed as set forth in Example 1 and agitated at room temperature for 8 hours in a sonic bath as set forth in Example 5, while maintaining a positive nitrogen flow through the manifold. At the end of the reaction, the reaction tube array is drained and sparged as set forth in Example 1.

The reaction tubes are washed as set forth in Example 3, using 2×3 mL each of the following solutions, dioxane:$H_2O$ (1:1), dioxane and $CH_2Cl_2$.

The reaction tubes are submerged in reaction wells containing a solution of ethylchloroformate (3 eq) and triethylamine (3 eq) in dioxane (3 mL) at −10° C. The apparatus is sealed as set forth in Example 1 and agitated in a sonic bath at room temperature for 4 hours as set forth in Example 5, while maintaining a positive nitrogen flow through the manifold. At the end of the reaction, the reaction tube array is allowed to warm to room temperature and then drained and sparged as set forth in Example 1.

The reaction tubes are washed as set forth in Example 3, using 4×2 mL of anhydrous DMF. Because of the labile nature of the above formed acyl-carbonates, the reaction tubes are rapidly washed in order to minimize unwanted hydrolysis.

The appropriate reaction tubes are submerged in reaction wells containing a solution of 4 eq of either n-butylamine, cycloheptylamine, 8-azaspiro[4.5]decane, or dipentylamine in dioxane (4 mL) at −10° C. The apparatus is sealed as set forth in Example 1 and agitated in a sonic bath at −10° C. as set forth in Example 5 for 1 hour and then 3 hours at room temperature, while maintaining a positive nitrogen flow through the manifold. At the end of the reaction, the reaction tube array is drained and sparged as set forth in Example 1.

The reaction tubes are washed as set forth in Example 3, using 2×3 mL each of the following solutions, dioxane:$H_2O$ (1:1), dioxane:1N HCl (1:1), dioxane: $H_2O$ (1:1), dioxane: 0.1N NaOH (1:1), dioxane: $H_2O$ (1:1), and dioxane.

The reaction tubes are submerged in reaction wells containing a solution of 20% piperidine in DMF at room temperature. The apparatus is sealed as set forth in Example 1 and agitated at room temperature in a sonic bath for 6 hours as set forth in Example 5, while maintaining a positive nitrogen flow through the manifold. At the end of the reaction, the reaction tube array is drained and sparged as set forth in Example 1.

The reaction tubes are washed as set forth in Example 3, using 2×3 mL each of the following solutions, DMF, dioxane:$H_2O$ (1:1), dioxane and $CH_2Cl_2$.

The appropriate reaction tubes are submerged in reaction wells containing a solution of 2 eq of either benzoyl chloride, 3-methoxybenzoyl chloride, or 3-nitrobenzoyl chloride in pyridine (3 mL) at 0° C. The apparatus is sealed as set forth in Example 1 and agitated in a sonic bath at 0° C. for 3 hours as set forth in Example 5, while maintaining a positive nitrogen flow through the manifold. At the end of the reaction, the apparatus is allowed to warm to room temperature, and the reaction tubes are drained and sparged as set forth in Example 1.

The reaction tubes are washed as set forth in Example 3, using 3×2 mL each of the following solutions, dioxane, dioxane:$H_2O$ (1:1), and dioxane.

In order to cleave the product from the solid support, the reaction tubes are submerged in reaction wells containing 3 mL each of trifluoroacetic acid. The apparatus is sealed as set forth in Example 1 and agitated in a sonic bath at 0° C. for 2 hours and then at room temperature for 4 hours as set forth in Example 5, while maintaining a positive nitrogen flow through the manifold. After 6 hours in a sonic bath, the apparatus is allowed to warm to room temperature, and the reaction tubes are drained and sparged as set forth in Example 1.

The reaction tubes are washed as set forth in Example 3, using 2×3 mL of methylene chloride. The filtrates are then combined and concentrated as set forth in Example 3. The crude products are then redissolved, transferred to tared vials, and reconcentrated to yield the final crude products.

EXAMPLE 8

Synthesis of Diketopiperazines

The synthesis of 40 diketopiperazines is summarized in Scheme 8 and Table 8.

95 to 105 mg of Merrifield's resin (loading=0.66 meq/g, 200–400 mesh) is measured into each of 40 gas dispersion tubes (reaction tubes) containing a magnetic stirring bar. The apparatus is assembled, swelled with 3 mL of DMF, and drained as set forth in Example 1.

The reaction tubes are submerged into wells containing a solution of 75.0 mg BOC 4-hydroxyproline cesium salt in 5 mL of DMF. The apparatus is assembled and sealed with clamps as set forth in Example 1, and placed into an oil bath over a magnetic stirring plate while maintaining a positive chilled nitrogen flow through the manifold as set forth in Example 2 and reacted at 50° C. After 24 hours, the reaction tube array is drained and sparged as set forth in Example 1.

The reaction tube array is subjected to the standard wash cycle set forth in Example 1, ending however in $CH_2Cl_2$, to remove residual reagents and byproducts.

The appropriate reaction tubes are submerged in reaction wells containing a solution of 5 mL of 0.07M acyl halide (either, benzoyl bromide, acetyl chloride, 4-biphenylcarbonyl chloride, p-anisoyl chloride, 4-chlorobenzoyl chloride, 4-nitrobenzoyl chloride, pivaloyl chloride, or trifluoroacetyl chloride) and 0.07M triethylamine in $CH_2Cl_2$. The apparatus is sealed as set forth in Example 1 and agitated as above while maintaining a positive nitrogen flow through the manifold. After 72 hours, the reaction tube array is drained and sparged as set forth in Example 1, using DMF, methanol, and $CH_2Cl_2$.

The reaction tubes are submerged in 5 mL of 0.08M TFA in $CH_2Cl_2$ to remove the BOC protecting group from $N_1$. The apparatus is assembled and the reactions stirred as above. After 72 hours, the reaction tubes are drained and washed with DMF, methanol, 1.0M TFA in $CH_2Cl_2$, and $CH_2Cl_2$ as set forth in Example 1.

A solution (5 mL) of 0.07M BOC amino acid, 0.07M diisopropylcarbodiimide and 0.07M TFA in $CH_2Cl_2$ are stirred for 3 hours at room temperature. The appropriate reaction tubes are then submerged in the above reaction wells, and the apparatus is assembled as set forth in Example 1. Five BOC amino acids are employed, BOC-glycine, BOC-alanine, BOC-valine, BOC-phenylalanine, and BOC-diphenylglycine. After 72 hours, the reaction tube array is drained and sparged as set forth in Example 1.

The reaction tube array is subjected to the standard wash cycle set forth in Example 1, ending however in $CH_2Cl_2$.

Cyclization to the final product and thus cleavage from the resin is accomplished by removal of the BOC (t-butyloxycarbony) group of the amino acid. The reaction tubes are submerged in reaction wells containing a solution of 5 mL of saturated HCl in $CH_2Cl_2$. The apparatus is assembled as set forth in Example 1 and the reactions stirred as above at room temperature. After 24 hours, the reaction tube array is drained and sparged as set forth in Example 1. The contents in the reaction wells are concentrated to dryness using a stream of nitrogen as set forth in Example 3.

A solution of 5 mL of 1.0M triethylamine in $CH_2Cl_2$ is added to each reaction well and the reaction tubes are then submerged in these wells. The apparatus is assembled as set forth in Example 1, and the reactions stirred as above. After 24 hours, the reaction tube array is drained and sparged as set forth in Example 1.

The contents in the reaction wells are concentrated no dryness using a stream of nitrogen as set forth in Example 3. These crude produce are partitioned between $CH_2Cl_2$ and a saturated solution of $NaHCO_3$ using a Tecan® robot to deliver the necessary liquids and to remove the aqueous layer. The basic aqueous wash is repeated and the residual $CH_2Cl_2$ layers are dried by passing the samples through a bed of $MgSO_4$ contained in standard SPE cartridges employing the vacuum SPE apparatus described above, giving the crude diketopiperazines.

EXAMPLE 9

Synthesis of
Tetrahydro-4-hydroxy-6-[2-(1H-pyrrol-1yl)
ethyl]-2H-pyran-2-ones

The synthesis of three 2H-pyranones is summarized in Scheme 9 and Table 9.

Three dispersion tubes are loaded each with 100±5 mg of hydroxymethyl polystyrene resin (1% cross-linked, 1.0 meq/g, loading) and placed in the holder block. The apparatus is assembled, swelled with 3 mL of acetonitrile, and drained as sen forth in Example 1.

The appropriate reaction tubes are submerged in reaction wells containing 2 mL of a solution of either 0.2M acetic anhydride, propanoic anhydride, or 2-phenylacetic anhydride in acetonitrile, and 1.0 mL of a 0.4M solution of triethylamine in $CH_2Cl_2$. The apparatus is sealed as set forth in Example 1, and agitated in a sonic bath while maintaining a positive nitrogen flow through the manifold for 12 hours.

At the end of the reaction, the reaction tube array is drained and sparged as set forth in Example 1.

The reaction tubes are washed as set forth in Example 3, using 10×4 mL of $CH_2Cl_2$.

The reaction tubes are submerged in reaction wells containing 3 mL of a solution of 0.2M lithium diisopropylamide in THF and the apparatus is sealed as set forth in Example 1 and agitated in a sonic bath at room temperature as set forth in Example 5, while maintaining a positive nitrogen flow through the manifold for 4 hours.

1 mL of a solution (in THF) of either 1.0M 5-[2-(4-fluorophenyl)-3-phenyl-4-carboxamidophenyl- 5-isopropyl-1-pyrrololyl]-3-oxo-1-pentanoic acid methyl ester (to wells #1 and #2), or 1.0M 5-[2,3,4-triphenyl-5-methyl-1-pyrroloyl]-3-oxo- 1-pentanoic acid methyl ester (to well #3) is added to the top of the appropriate reaction tubes through the gasket at the top of the manifold and sonicated at room temperature for 12 hours as set forth in Example 5. At the end of the reaction, the reaction tube array is drained and sparged as set forth in Example 1.

The reaction tubes are washed as set forth in Example 3, using 10×4 mL of $CH_2Cl_2$.

The reaction tubes are submerged in reaction wells containing 2.0 mL of a 0.26M THF solution of diethyl methoxy borane and the apparatus is sealed as set forth in Example 1. 1.0 mL of a 1.0M THF solution of sodium borohydride is added to the top of the appropriate reaction tubes through the gasket at the top of the manifold and the apparatus is sonicated at room temperature for 4 hours as set forth in Example 5. At the end of the reaction, the reaction tube array is drained and sparged as set forth in Example 1.

The reaction tubes are washed as set forth in Example 3, using 10×4 mL of $CH_2Cl_2$.

The reaction tubes are submerged in reaction wells containing 3.0 mL of 3% hydrogen peroxide in 1:1 dioxane:water and the apparatus is assembled as set forth in Example 1, and sonicated at room temperature for 6 hours as set forth in Example 5 to affect boron oxidation. At the end of the reaction, the reaction tube array is drained and sparged as set forth in Example 1.

The reaction tubes are washed as set forth in Example 3, using 10×3 mL of dioxane:water (1:1).

The reaction tubes are submerged in reaction wells containing a solution of 0.1M HCl in 1:1 dioxane:water (3 mL). The apparatus is assembled as set forth in Example 1, and sonicated at room temperature for 6 hours as set forth in Example 5 to affect hydrolysis/ring closure. At the end of the reaction, the reaction tube array is drained and sparged as set forth in Example 1.

The reaction tubes are washed as set forth in Example 3, using 3×3 mL of dioxane:water (1:1). The appropriate filtrates are then combined and concentrated as set forth in Example 3 to give the three individual expected lactone products.

EXAMPLE 10

Synthesis Of N-Arylpiperazines

The synthesis of 12 N-arylpiperazines is summarized in Scheme 10 and Table 10.

100 mg of hydroxymethyl polystyrene (2% cross-linked, 1.2 meq/g, loading) resin is measured into each of 12 gas dispersion tubes (reaction tubes). The apparatus is assembled, swelled with 3 mL of DMF, and drained as set forth in Example 1.

To facilitate coupling of the acid, the appropriate reaction tubes are submerged in reaction wells containing a solution of 0.09M 4-chlorobutyric acid or 3-chloropropionic acid; and 0.09M N,N'-diisopropylcarbodiimide and 0.09M 4,4-dimethylaminopyridine in DMF (3 mL) at room temperature. The apparatus is sealed as set forth in Example 1 and agitated in a sonic bath for 2 hours, while maintaining a positive nitrogen flow through the manifold. At the end of the reaction, the reaction tube array is drained and sparged as set forth in Example 1.

The reaction tube array is subjected to the standard wash cycle set forth in Example 1.

The appropriate reaction tubes are submerged in reaction wells containing a solution of 3 mL of either 0.09M piperazine, phenylpiperazine, or 1-(2-pyridyl) piperazine; 0.18M potassium carbonate; and 0.18M potassium iodide in DMF. The apparatus is sealed as set forth in Example 1, placed in an oil bath, and heated at 95° to 100° C. while maintaining a positive chilled nitrogen flow through the manifold as set forth in Example 2. After 6 hours, the reaction is stopped and the reaction tube array is drained and sparged as set forth in Example 1.

The reaction tube array is subjected to the standard wash cycle set forth in Example 1.

The appropriate reaction tubes are submerged in reaction wells containing a solution of 3 mL of toluene-20% 1,2-dimethoxyethane at 0° C. The apparatus is sealed as set forth in Example 1 and agitated in a sonic bath at 0° C. as set forth in Example 5, while maintaining a positive argon flow.

To form the enolate, 0.5 mL of a solution (in THF) of 0.15M trityllithium is added to the top of the appropriate reaction tubes through the gasket at the top of the manifold and sonicated at 0° C. for 15 minutes as set forth in Example 5.

After 15 minutes, 0.5 mL of 0.28M acid chloride (either nicotinoyl chloride or naphthoyl chloride) in THF is added to the top of the appropriate reaction tubes through the gasket at the top of the manifold and sonicated at room temperature for 1 hour as set forth in Example 5. At the end of the reaction, the reaction tube array is drained and sparged as set forth in Example 1.

The reaction tube array is subjected to the standard wash cycle set forth in Example 1.

In order to cleave the product from the solid support, the reaction tubes are submerged in reaction wells containing a solution of 3 mL of dry HBr in TFA. The apparatus is sealed as set forth in Example 1 and agitated in a sonic bath while maintaining a positive nitrogen flow through the manifold. After 1 hour, the reaction is stopped, and the reaction tube array is drained and sparged as set forth in Example 1.

To isolate and purify the products, the reaction tubes are washed as set forth in Example 1, using 3 mL portions of methanol. The methanol extraction protocol is repeated until the filtrates are free of any organic components as determined by TLC (1–2 times). The appropriate HCl and methanol filtrates are then combined and concentrated on a Speed-Vac® in tared vials to afford 12 discrete products.

In an example of a post-cleavage reaction, a modified Wolff-Kishner reduction is done on half of the amount of each of the isolated compounds. The compounds are placed in the appropriate reaction wells containing 3 mL of 0.09M potassium hydroxide, and 0.09M hydrazine hydrate in diethylene glycol. The reaction tubes are filled with 0.5 g sodium sulfate (to absorb water) and submerged in the reaction wells. The apparatus is sealed as set forth in Example 1, placed in an oil bath, and heated at 80° C. while maintaining a positive chilled nitrogen flow through the manifold as set forth in Example 2. After 12 hours, the reaction is stopped and the reaction tube array is drained and sparged as set forth in Example 1. Each product is isolated by adding 4 mL of a solution of 1:1 water:$CH_2Cl_2$. Each organic layer is separated, dried, and concentrated as set forth in Example 8 to yield another 12 desired products.

EXAMPLE 11

Synthesis of Benzisothiazolones

The synthesis of nine benzisothiazolones is summarized in Scheme 11 and Table 11.

95 to 105 mg of Merrifield's resin (loading 0.66 meq/g, 200–400 mesh) is measured into each of nine gas dispersion tubes (reaction tubes). The apparatus is assembled, swelled with 3 mL of dioxane and drained as set forth in Example 1.

The appropriate reaction tubes are submerged in reaction wells containing a solution of 5 mL of either 0.2M thiosalicylic acid, 5-chloro-thiosalicylic acid, or 2-mercaptonicotinic acid; and 0.4M triethylamine in dioxane and magnetic stirring bars. The apparatus is sealed with clamps as set forth in Example 1 and placed over a magnetic stirring plate, while maintaining a positive nitrogen flow through the manifold. After 96 hours, the reaction is stopped and the reaction tube array is drained and sparged as set forth in Example 1.

The reaction tubes are washed as set forth in Example 3, using 3×3 mL each of water, 1N HCl, 1N HCL:dioxane (1:1), and finally dioxane to remove residual reagents and byproducts.

The reaction tubes are submerged in reaction wells containing a solution of 5 mL of 0.20M carbonyldiimidazole in dioxane. The apparatus is assembled and agitated as above. After 5 hours, the reaction is stopped and the reaction tube array is drained and sparged as set forth in Example 1.

The reaction tubes are washed as set forth in Example 3, using 4×3 mL each of DMF then dioxane.

The appropriate reaction tubes are submerged in reaction wells containing a solution of 5 mL of either 0.20M 4-methoxyaniline, cyclohexylamine, or benzylamine in dioxane. The apparatus is assembled as set forth in Example 1, while maintaining a flow of cold nitrogen. The apparatus is placed in an oil bath over a magnetic stirring plate and the reactions are warmed to reflux and stirred as above. After 24 hours, the reaction is stopped and the reaction tube array is drained and sparged as set forth in Example 1.

The reaction tubes are washed as set forth in Example 3, using 4×3 mL each of DMF, methanol, $CH_2Cl_2$, and then dioxane.

The reaction tubes are submerged in reaction wells containing a solution of 5 mL of 0.13M $NaBrO_2$ in dioxane/water (8:1). The apparatus is assembled as set forth in Example 1, while maintaining a flow of nitrogen. The apparatus is placed over a magnetic stirring plate and stirred at room temperature as above. After 1 hour, the reaction is stopped and the reaction tube array is drained and sparged as set forth in Example 1.

The reaction tubes are washed as set forth in Example 3, using 4×3 mL each of dioxane, water, dioxane/water (1:1), methanol, and then $CH_2Cl_2$.

Cyclization to the final product and thus cleavage from the resin is accomplished by addition of trichloroacetic anhydride to the sulfoxide and rearrangement as taught by Wright, et al, *Tetrahedron Letters* 1991;33:153. Thus, reaction tubes are submerged in reaction wells containing a solution of 5 mL of $CH_2Cl_2$. The apparatus is assembled as set forth in Example 1, while maintaining a flow of nitrogen. The apparatus is then placed in a cold bath at 0° C. and the reactions stirred as above. Trichloroacetic anhydride (0.18 mL) is then added to the top of each reaction tube through the gasket at the top of the manifold and the temperature of the reaction is allowed to warm to 25° C. over 7 hours. At the end of the reaction, the reaction tube array is drained and sparged as set forth in Example 1.

The reaction tubes are washed as set forth in Example 3, using 2×3 mL each of $CH_2Cl_2$, dioxane, MeOH, and $CH_2Cl_2$.

The appropriate filtrates are then combined and concentrated as set forth in Example 3. These crude products are partitioned between $CH_2Cl_2$ and 2N NaOH using a Tecan® robot to deliver the necessary liquids and to remove the aqueous layer. The basic aqueous wash is repeated and the residual $CH_2Cl_2$ layers are dried by passing the samples through a bed of $MgSO_4$ contained in standard SPE cartridges employing the vacuum SPE apparatus described above to yield the crude benzisothiazolones.

EXAMPLE 12

Synthesis of Isoindolone-Based Spirosuccinimdes

The synthesis of nine spirosuccinimides is summarized in Scheme 12 and Table 12.

A solution of 0.10 mol cyanoacetic acid and 0.10 mol carbonyldiimidazole are combined in 500 mL of dioxane. After 5 hours, 10 g of benzylhydroxy polystyrene resin (loading=1.08 meq/g, 200 400 mesh) is added. The reaction is refluxed for 8 hours, cooled to room temperature, filtered, and washed with DMF, methanol, dioxane, and finally $CH_2Cl_2$. The product resin, benzyl cyanoacetate polystyrene resin, is used directly in the next step.

95 of 105 mg of the resin prepared above (loading= 1.08 meq/g, 200–400 mesh) is measured into each of nine gas dispersion tubes (reaction tubes). The apparatus is assembled, swelled with 3 mL of DMF and drained as set forth in Example 1.

The appropriate reaction tubes are submerged in reaction wells containing a solution of 5 mL of either 0.20M 3-imino-1-oxoisoindoline, 6-chloro-3-imino- 1-oxoisoindoline, or 6-phenyl-1-oxoisoindoline in diglyme with stirring magnetic bars. The 3-imino- 1-oxoisoindoline employed are prepared by the method of Wrobel, et al, *Journal of Medicinal Chemistry* 1992;35:4613. The apparatus is sealed with clamps as set forth in Example 1, and placed in an oil bath over a magnetic stirring plate while maintaining a positive flow of cold nitrogen as set forth in Example 2. The reaction vessels are warmed to reflux, and after 2 hours the reaction is stopped, and the reaction tube array is drained and sparged as set forth in Example 1.

The reaction tubes are washed as set forth in Example 3, using 3×3 mL each of dioxane, $CH_2Cl_2$, and DMF.

The appropriate reaction tubes are submerged in reaction wells containing a solution of 0.20M alkyl halide (either methyl iodide, benzyl bromide and 3-bromobenzyl bromide) and 1 mmol $K_2CO_3$ in 5 mL of DMF. The apparatus is assembled as set forth in Example 1, while maintaining a positive flow of cold nitrogen as set forth in Example 2. The oil bath is then warmed to 100° C. and agitated as above. After 24 hours, the reaction is stopped and the reaction tube array is drained and sparged as set forth in Example 1.

The reaction tubes are washed as set forth in Example 3, using 3×3 mL each of DMF, water, MeOH, dioxane, $CH_2Cl_2$, and DMSO.

The reaction tubes are submerged in reaction wells containing a solution of 5 mL of 0.20M potassium cyanide in DMSO. The apparatus is assembled as set forth in Example 1 and agitated as above. After 24 hours at 25° C., the reaction is stopped and the reaction tube array is drained and sparged as set forth in Example 1.

The reaction tubes are washed as set forth in Example 3, using 3×3 mL each of DMF, water, MeOH, water, and 10% aqueous HCl.

The reaction tubes are submerged in reaction wells containing a solution of saturated dry HCl in MeOH. The apparatus is assembled as set forth in Example 1 and agitated as above. After 3 days at 25° C., the reaction is stopped and the reaction tube array is drained and sparged as set forth in Example 1.

The reaction tubes are washed as set forth in Example 3, using 3×3 mL each of MeOH, dioxane, and $CH_2Cl_2$.

The appropriate filtrates are then combined and concentrated as set forth in Example 3.

The crude products are dissolved in glacial HOAc and a holder block with nine clean empty reactions tubes is attached. The apparatus is assembled as set forth in Example 1 and agitated as above. After 24 hours at 25° C., the reaction is stopped and the reaction tube array is drained and sparged as set forth in Example 1.

The reaction tubes are washed as set forth in Example 3, using 3×3 mL of MeOH.

The appropriate filtrates are then combined and concentrated as set forth in Example 3 to yield the crude spiro[1H-isoindole-1,3'-pyrolidine]-2',3,5'(2H)-triones.

EXAMPLE 13

Synthesis of Pilocarpine Analogs

The synthesis of four pilocarpine analogs is summarized in Scheme 13 and Table 13.

95 to 105 mg of 2-Chloro-triphenylmethyl resin as taught by Barlos, et al, *Tetrahedron Letters* 1989;30:3947 is measured into each of four gas dispersion tubes (reaction tubes). The apparatus is assembled, swelled with 3 mL of DMF, and drained as set forth in Example 1.

FMOC-histidine methyl ester is coupled to the resin. The reaction tubes are submerged in reaction wells containing a solution of 0.2M FMOC-histidine methyl ester and 0.4M pyridine in 3 mL dry THF. The apparatus is sealed as set forth in Example 1 and agitated in a sonic bath for 6 hours, while maintaining a positive nitrogen flow through the manifold. At the end of the reaction, the reaction tube array is drained and sparged as set forth in Example 1.

The reaction tube array is subjected to the standard wash cycle set forth in Example 1.

To deprotect the FMOC amino acids, reaction tubes are submerged in reaction wells containing 3 mL of a solution of 25% piperidine in DMF. The apparatus is sealed as set forth in Example 1 and placed in a sonic bath, while maintaining a positive nitrogen flow through the manifold. The reaction is stopped after 4 hours. At the end of the reaction, the reaction tube array is drained and sparged as set forth in Example 1.

The reaction tube array is subjected to the standard wash cycle set forth in Example 1.

The appropriate reaction tubes are submerged in reaction wells containing a solution of 0.2M anhydride (either acetic anhydride or isobutyric anhydride) and 0.4M triethylamine in 3 mL of dry THF. The apparatus is sealed as set forth in Example 1 and agitated in a sonic bath for 12 hours, while maintaining a positive nitrogen flow through the manifold. At the end of the reaction, the reaction tube array is drained and sparged as set forth in Example 1.

The reaction tube array is subjected to the standard wash cycle set forth in Example 1.

The apparatus is sealed as set forth in Example 1 while maintaining a positive nitrogen flow through the manifold. A solution of lithium aluminum hydride (LAH) in dry THF (0.1M, 3 mL) is then added to the top of each reaction tube through the gasket at the top of the manifold. The apparatus is placed in an oil bath heated at 67° C. for 8 hours, while maintaining a positive chilled nitrogen flow through the manifold (as set forth in Example 2). The apparatus is cooled to room temperature and 1 mL of water is added to the top of each reaction tube through the gasket at the top of the manifold, and the apparatus sonicated at room temperature for 30 minutes to neutralize any unreacted LAH. At the end of the reaction, the reaction tube array is drained and sparged as set forth in Example 1.

The reaction tube array is subjected to the standard wash cycle set forth in Example 1, except that a base wash cycle is added to remove the neutralized LAH salts.

The cyclic carbamate is formed according to the method of Gonzalez, et al, *Tetrahedron Letters* 1989;30:2145. The reaction tubes are submerged in reaction wells containing a solution of 0.2M diethyl carbonate and 0.4M NaOMe in MeOH. The apparatus is sealed as set forth in Example 1 and agitated in a sonic bath for 12 hours, while maintaining a positive nitrogen flow through the manifold. At the end of the reaction, the reaction tube array is drained and sparged as set forth in Example 1.

The reaction tube array is subjected to the standard wash cycle set forth in Example 1.

The appropriate reaction tubes are submerged in reaction wells containing a solution of 0.2M iodoalkane (either 1-iodohexane, or iodomethane) in 3 mL of $CH_2Cl_2$. The apparatus is sealed as set forth in Example 1 and agitated in a sonic bath while maintaining a positive nitrogen flow through the manifold for 1 hour. The apparatus then placed in an oil bath heated at 37° C., while maintaining a positive chilled nitrogen flow through the manifold (as set forth in Example 2) for 6 hours. At the end of the reaction, the reaction tube array is drained and sparged as set forth in Example 1.

The reaction tube array is subjected to the standard wash cycle set forth in Example 1.

To isolate and purify the products, the reaction tubes are submerged in reaction wells containing a solution 3 mL each of MeOH. The apparatus is sealed as set forth in Example 1, placed in an oil bath and heated at 64° C. while maintaining a positive chilled nitrogen flow through the manifold as set forth in Example 2. At the end of the reaction, the reaction tube array is allowed to cool and then drained and sparged as set forth in Example 1.

The reaction tubes are washed as set forth in Example 1, using 3 mL portions of methanol. The methanol extraction

EXAMPLE 24

3-Substituted 1-(Aminomethyl)-3,4-dihydro-5,6-dihydroxy-1H-2-benzopyrans

The synthesis of six benzopyrans is summarized in Scheme 14 and Table 14.

10 g of Merrifield's chloromethyl polystyrene resin (2% cross-linked, loading=1.2 meq/g, 200–400 mesh) is reacted with excess sodium ethyl acetoacetate (10 eq) in DMF at 80° C. for 16 hours. After washing with DMF and dioxane the crude beta-keto ester is hydrolyzed and decarboxylated 4N HCl:dioxane (1:1) at 60° C. to give the phenethyl ketone resin, after washing with dioxane. This is further reacted with excess catechol and cat. p-TsOH in toluene at 90° C. for 30 hours. The resin is thoroughly washed with toluene, dioxane, and $CH_2Cl_2$ to remove all catechol. The crude resin is then used directly below.

95 to 105 mg of the catechol ketal resin prepared above is measured into each of six gas dispersion tubes (reaction tubes). The reaction tubes are fitted into the appropriate holder block and swelled and drained as set forth in Example 1.

The appropriate reaction tubes are submerged in reaction wells containing a solution of nBuLi (1 eq) in THF at 0° C. The apparatus is sealed as set forth in Example 1 and agitated in a sonic bath (maintained at 0° C. as set forth in Example 5), while maintaining a positive nitrogen flow through the manifold. After 1 hour, the bath is warmed to room temperature and sonicated for 3 hours more. The bath is then re-cooled to 0° C. and a solution of either cyclohexyl- or phenylethyleneoxide (2 eq) in THF (0.5 mL) is then added to the top of the appropriate reaction tube through the gasket at the top of the manifold. The bath is again warmed to room temperature and sonicated for 2 hours. The apparatus is then removed from the sonic bath, and 0.5 mL of $THF:H_2O$ (1:1) are added to the top of each reaction tube through the gasket at the top of the manifold as above, to quench any excess n-BuLi. At the end of the reaction, the reaction tube array is drained and sparged as set forth in Example 1.

The reaction tubes are washed as set forth in Example 3, using 3×3 mL each of dioxane:sat $NH_4Cl$ (1:1), dioxane:$H_2O$ (1:1), and dioxane.

The appropriate reaction tubes are submerged in reaction wells containing a solution of (2 eq) of either bromoacetaldehyde dimethyl acetal (4 reaction tubes) or [(formylamino)methyl]acetaldehyde dimethyl acetal (2 reaction tubes); and $BF_3OEt_2$ (3 eq) in $Et_2O$ (3 mL) at 0° C. The apparatus is sealed as set forth in Example 1 and agitated in a sonic bath at room temperature for 24 hours, while maintaining a positive nitrogen flow through the manifold. At the end of the reaction, the reaction tube array is drained and sparged as set forth in Example 1.

The reaction tubes are washed as set forth in Example 3, using 3×3 mL each of dioxane:$H_2O$ (1:1), dioxane:$H_2O$ 0.1N NaOH (1:1), dioxane:$H_2O$ (1:1), dioxane.

The appropriate four reaction tubes are submerged in reaction wells containing a solution of either allylamine or benzylamine (2 eq) in dioxane (4 mL) at room temperature. The other two reaction tubes (those which are reacted with [(formylamino)methyl]acetaldehyde dimethyl acetal above) are submerged in wells containing a solution of dioxane:MeOH:15% NaOH (2:2:1) 5 mL at room temperature. The apparatus is sealed as set forth in Example 1 and agitated in a sonic bath at 60° C. as set forth in Example 5, while maintaining a positive chilled nitrogen flow through the manifold as set forth in Example 2. After 8 hours the reaction is stopped, the reaction tube array is allowed to cool, and then drained and sparged as set forth in Example 1.

The reaction tubes are washed as set forth in Example 3, using 3×2 mL each of dioxane, dioxane:$H_2O$ (1:1), dioxane.

In order to cleave the products from the solid support, the reaction tubes are submerged in reaction wells containing a solution of 3 mL of 5M HCl in dioxane:ethanol (1:1). The apparatus is sealed as set forth in Example 1 and agitated in a sonic bath at 80° C. for 4 hours as set forth in Example 5, while maintaining a positive chilled nitrogen flow through the manifold as set forth in Example 2. After 4 hours the reaction is stopped, the reaction tube array is allowed to cool, and then drained and sparged as set forth in Example 1.

The reaction tubes are washed as set forth in Example 3, using 3×3 mL of dioxane:ethanol (1:1). The filtrates are then combined and concentrated as set forth in Example 3. The crude products are then redissolved, transferred to tared vials, and reconcentrated. The final crude products including, cis-1-(aminomethyl)-3-cyclohexyl-3,4-dihydro- 5,6-dihydroxy-1H-2-benzopyran hydrochloride; cis- 1-(aminomethyl)-3-phenyl-3,4-dihydro-5,6-dihydroxy-1H- 2-benzopyran hydrochloride; cis-1-[(allylamino)methyl]- 3-cyclohexyl-3,4-dihydro-5,6-dihydroxy-1H-2-benzopyranhydrochloride; cis-1-[(allylamino)methyl]-3-phenyl- 3,4-dihydro-5,6-dihydroxy-1H-2-benzopyranhydrochloride; cis-1-[(benzylamino)methyl]-3-cyclohexyl-3,4-dihydro-5,6-dihydroxy-1H-2-benzopyran hydrochloride; cis-1-[(benzylamino)methyl]-3-phenyl-3,4-dihydro- 5,6-dihydroxy-1H-2-benzopyran hydrochloride; are set forth in Table 14.

EXAMPLE 15

6,7-Dihydro-4H-pyrazolo[1,5-a]pyrrolo[3,4-d]-pyrimidine-5,8-diones

The synthesis of eight pyrimidinediones is summarized in Scheme 15 and Table 15.

15 g of Merrifield's chloromethyl polystyrene resin (2% cross-linked, loading=0.7 meq/g, 200–400 mesh) is reacted with excess cesium acrylate (10 eq) and NaI (0.1 eq) in DMF at 80° C. for 14 hours to yield the desired ester. The resin is thoroughly washed with DMF, dioxane:$H_2O$ (1:1), dioxane, and $CH_2Cl_2$ to remove excess reagents. The crude resin is then used directly below.

95 to 105 mg of the acrylate ester resin prepared above is measured into each of eight gas dispersion tubes (reaction tubes). The reaction tubes are fitted into the holder block and swelled and drained as set forth in Example 1.

The appropriate reaction tubes are submerged in reaction wells containing a solution of either cyclohexylamine or n-hexylamine (1 eq) in 3 mL of DMF at room temperature. The apparatus is sealed as set forth in Example 1 and agitated in a sonic bath (maintained at room temperature as set forth in Example 5), while maintaining a positive nitrogen flow through the manifold. After 24 hours, a solution of diethyl oxalate (1 eq) and $Na_2CO_3$ (1 eq) in 1 mL of DMF is added to the top of the each reaction tube through the gasket at the top of the manifold. The bath is warmed to 60° C. and sonicated for 2 hours. At the end of the reaction, the reaction tube array is allowed to cool and then drained and sparged as set forth in Example 1.

The reaction tubes are washed as set forth in Example 3, using 3×2 mL each of dioxane:sat. $NH_4Cl$ (1:1), dioxane:1N HCl (1:1), dioxane:$H_2O$ (1:1), and dioxane.

In order to cleave the products from the solid support, the appropriate reaction tubes are submerged in reaction wells containing a solution of (1 eq) of either 5-phenylpyrazol-3-amine or 5-(4-chlorophenyl) pyrazol-3-amine in HOAc (4 mL) at room temperature. The apparatus is sealed as set forth in Example 1 and agitated in a sonic bath at 100° C. for 2 hours as set forth in Example 5, while maintaining a positive chilled nitrogen flow through the manifold as set forth in Example 2. At the end of the reaction, the reaction tube array is allowed to cool and then drained and sparged as set forth in Example 1.

The reaction tubes are washed as set forth in Example 3, using 3×2 mL of dioxane:ethanol. The filtrates are then combined and concentrated as set forth in Example 3. The crude products are then redissolved, transferred to tared vials, and reconcentrated.

In an example of a post-cleavage reaction, a solution of either 2-chloroacetophenone (2 eq) and $K_2CO_3$ (1.1 eq) in DMF (3 mL) or 1-bromo-5-hexene (2 eq) and $K_2CO_3$ (1.1 eq) in DMSO (3 mL) is added to the appropriate reaction wells. A holder block with clean empty reaction tubes is added and the apparatus is sealed and agitated as set forth in Example 1 in a sonic bath at 40° C. for 22 hours as set forth in Example 5, while maintaining a positive chilled nitrogen flow through the manifold as set forth in Example 2. At the end of the reaction, the reaction tube array is allowed to cool and then drained and sparged as set forth in Example 1

The crude reaction mixtures are transferred to the corresponding tubes in the SPE apparatus equipped with 20 mL columns and 5 μm filters. Each reaction mixture is diluted and mixed with 15 mL of $H_2O$ to precipitate the desired products. The suspensions are then filtered and washed with $H_2O$ and $Et_2O$ (3×2 mL, each). The resulting solids are then dissolved with $CH_2Cl_2$ (3×2 mL washes) run through the filter and collected in clean tubes. These solutions are then concentrated as set forth in Example 3. The crude products are then redissolved, transferred to tared vials, and reconcentrated. The final crude products including, 6-Cyclohexyl-6,7-dihydro-4-(phenylmethyl)-2-phenyl- 4H-pyrazolo[1,5a] pyrrolo[3,4-d]-pyrimidine-5,8-dione; 6-Cyclohexyl-6,7-dihydro-4-(2-oxo-2-phenylethyl)- 2-phenyl-4H-pyrazolo[1,5-a]pyrrolo[3,4-d]-pyrimidine- 5,8-dione; 6-Cyclohexyl-6, 7-dihydro-4-(phenylmethyl)- 2-(4-chlorophenyl)-4H-pyrazolo[1,5-a]pyrrolo[3,4-d]pyrimidine- 5,8-dione; 6-Cyclohexyl-6,7-dihydro- 4-(2-oxo-2-phenylethyl)-2-(4-chlorophenyl)- 4H-pyrazolo[1,5-a]pyrrolo[3,4-d]-pyrimidine-5,8-dione; 6-Hexyl-6,7-dihydro-4-(phenylmethyl)-2-phenyl- 4H-pyrazolo[1,5-a]pyrrolo[3,4-d]-pyrimidine-5,8-dione; 6-Hexyl-6,7-dihydro-4-(2-oxo-2-phenylethyl)-2-phenyl- 4H-pyrazolo[1,5-a]-pyrrolo[3,4-d]-pyrimidine-5,8-dione; 6- Hexyl-6,7-dihydro-4-(phenylmethyl)-2-(4-chlorophenyl)- 4H-pyrazolo[1,5-a]pyrrolo[3,4-d]-pyrimidine- 5,8-dione; 6-Hexyl-6,7-dihydro-4-(2-oxo-2-phenylethyl)- 2-(4-chlorophenyl)-4H-pyrazolo[1,5-a] pyrrolo[3,4-d]-pyrimidine- 5,8-dione are set forth in Table 15.

EXAMPLE 16

Synthesis of Tepoxalin Derivatives

The synthesis of eight tepoxalin derivatives is summarized in Scheme 16 and Table 16.

95 to 105 mg of benzylhydroxy polystyrene resin (loading=1.08 meq/g, 200–400 mesh) is measured into each of eight gas dispersion tubes (reaction tubes). The apparatus is assembled, swelled with 3 mL of DMF, and drained as set forth in Example 1.

A solution (5 mL) of either 0.20M 6-phenyl- 4,6-dioxohexanoic acid, or 6-(4-chlorophenyl)- 4,6-dioxohexanoic acid and 0.20M carbonyldiimdazole in $CH_2Cl_2$ are stirred for 6 hours at room temperature. The two 6-aryl-4,6-dioxohexanoic acids employed are prepared by the method of Murray, et al, *Journal of Organic Chemistry* 1990;55:3424.

The appropriate reaction tubes are submerged in the reaction wells above. The apparatus is sealed as set forth in Example 1 and agitated in a sonic bath while maintaining a positive nitrogen flow through the manifold. After 12 hours, the reaction is stopped and the reaction tube array is drained and sparged as set forth in Example 1.

The reaction tubes are washed as set forth in Example 3, using 3×3 mL each of DMF, MeOH, dioxane, $CH_2Cl_2$, and MeOH.

The appropriate reaction tubes are submerged in reaction wells containing a solution of 5 mL of either 0.2M 4-methoxyphenylhydrazine hydrochloride or 4-methylphenylhydrazine hydrochloride and 0.2M triethylamine in MeOH. The apparatus is sealed as set forth in Example 1 and agitated in a sonic bath, while maintaining a positive nitrogen flow through the manifold. After 12 hours, the reaction is stopped and the reaction tube array is drained and sparged as set forth in Example 1.

The reaction tubes are washed as set forth in Example 3, using 3×3 mL each of DMF, MeOH, dioxane, and $CH_2Cl_2$.

Cleavage is accomplished by aminolysis of the resin ester linkage. Thus, the appropriate reaction tubes are submerged in reaction wells containing a solution of 5 mL of either 0.20M methylhydroxylamine hydrochloride or benzylhydroxylamine hydrochloride and 0.2M triethylamine in $CH_2Cl_2$ along with stirring bars. The apparatus is sealed with clamps as set forth in Example 1 and placed in an oil bath over a magnetic stirring plate while maintaining a positive flow of cold nitrogen as set forth in Example 2. The reaction vessels are warmed to reflux and stirred as above. After 24 hours, the reaction is stopped and the reaction tube array is drained and sparged as set forth in Example 1.

The reaction tubes are washed as set forth in Example 3, using 3×3 mL each of MeOH, dioxane, and $CH_2Cl_2$.

The appropriate filtrates are then combined and concentrated as set forth in Example 3. These crude products are partitioned between $CH_2Cl_2$ and 1M HCl using a Tecan® robot to deliver the necessary liquids and to remove the aqueous layer. The acidic aqueous wash is repeated and the residual $CH_2Cl_2$ layers are dried by passing the samples through a bed of $MgSO_4$ contained in standard SPE cartridges employing the vacuum SPE apparatus described above to yield tepoxalin and the expected tepoxalin derivatives.

SCHEME 1

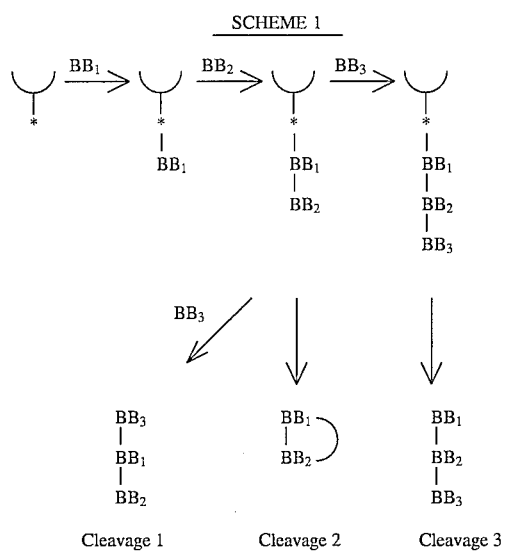

BB$_N$ represents the building blocks which are bifunctional to allow sequential attachment. The curved structure represents the solid support where the asterisk is the functionality capable of covalently attaching the growing molecule to the solid support.

The three possible cleavage model are illustrated. Cleavage 1 represents the third building block attacking the solid support linkage to cleave the final molecule. This provides structural variation at the former site of attachment to the support. Cleavage 2 represents a distal functionality attacking the solid support linkage to cleave the final molecule as a cyclized product. Cleavage 3 represents a cleavage by an invariant agent. This provides a constant functional group at the former site of attachment to the support.

SCHEME 2

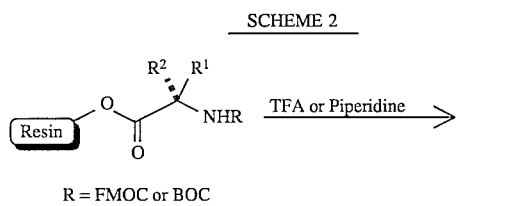

R = FMOC or BOC

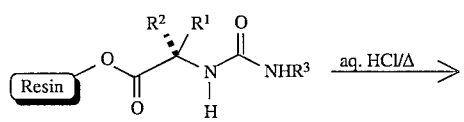

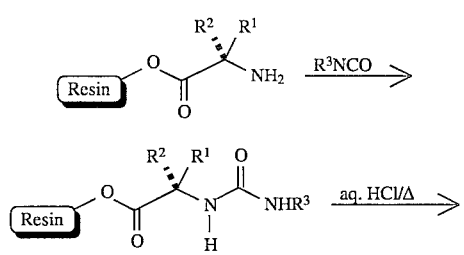

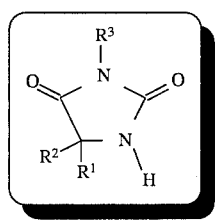

SCHEME 3

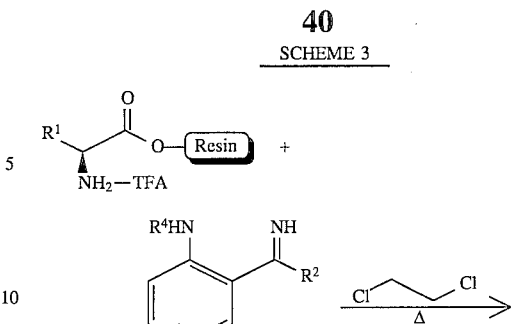

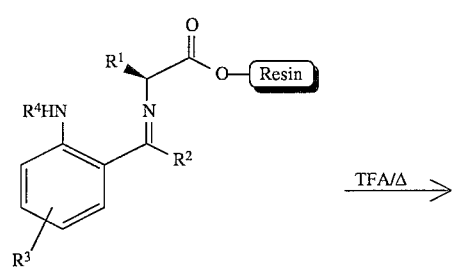

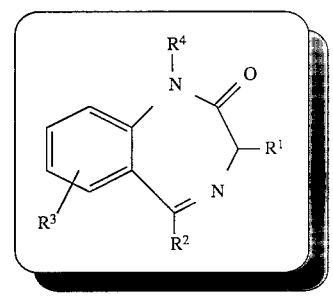

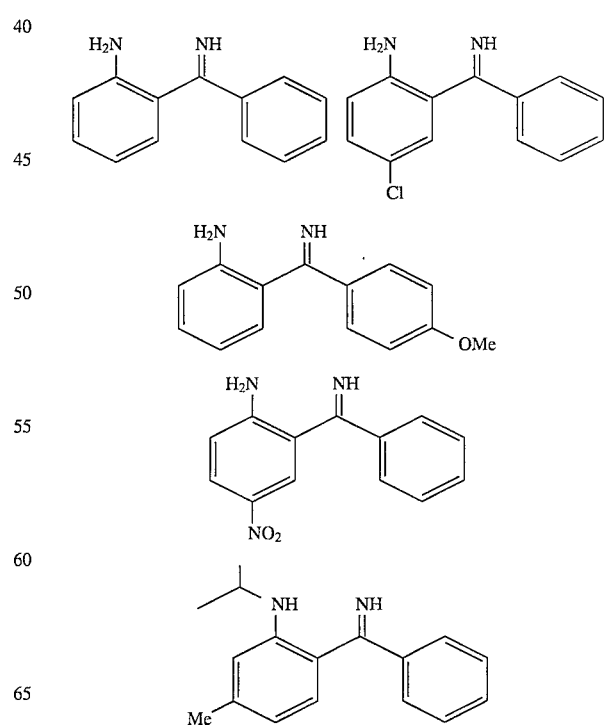

Imines:

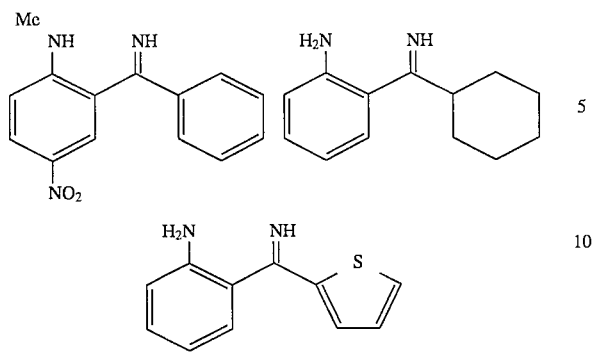
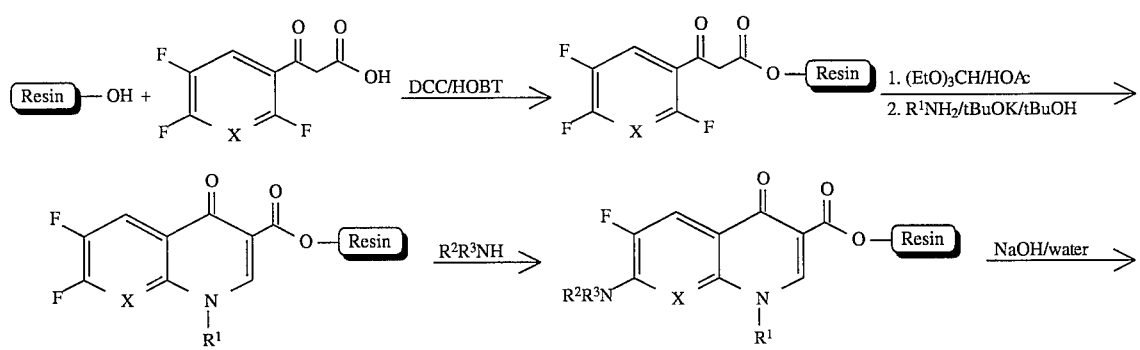
SCHEME 4
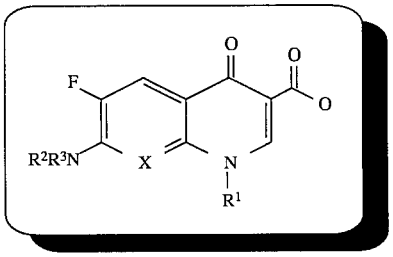
SCHEME 5
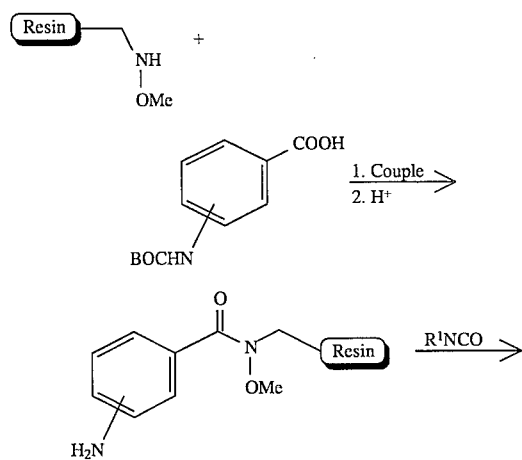

5,565,173
43
-continued
SCHEME 5
44
SCHEME 6
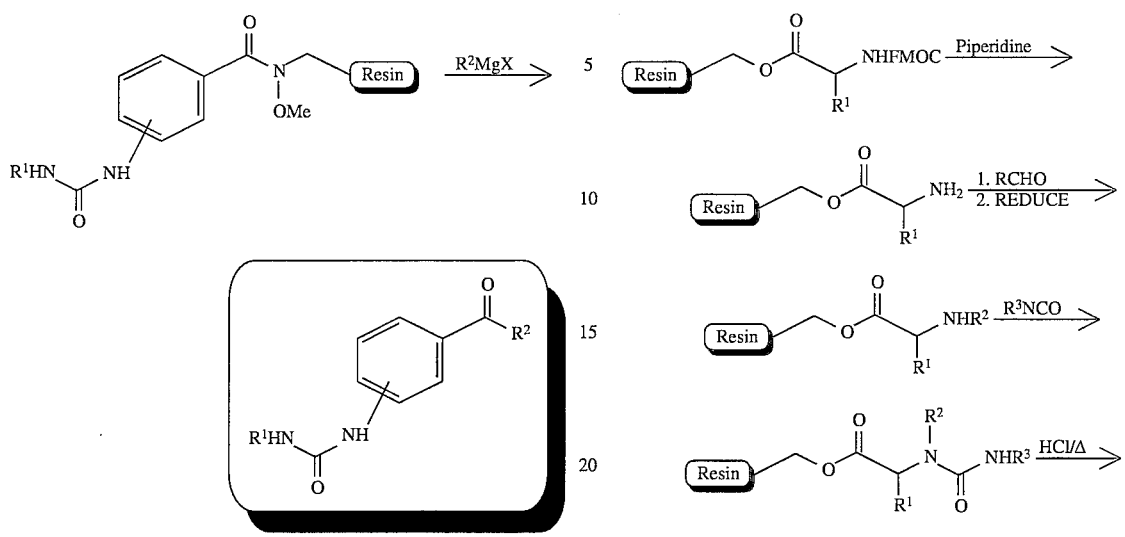
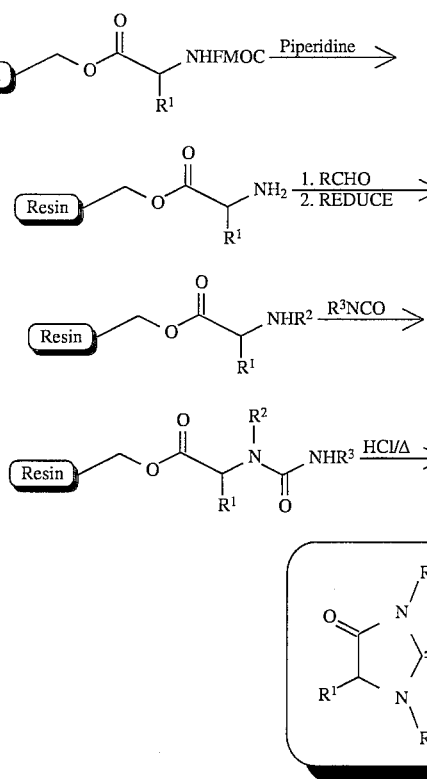
SCHEME 7
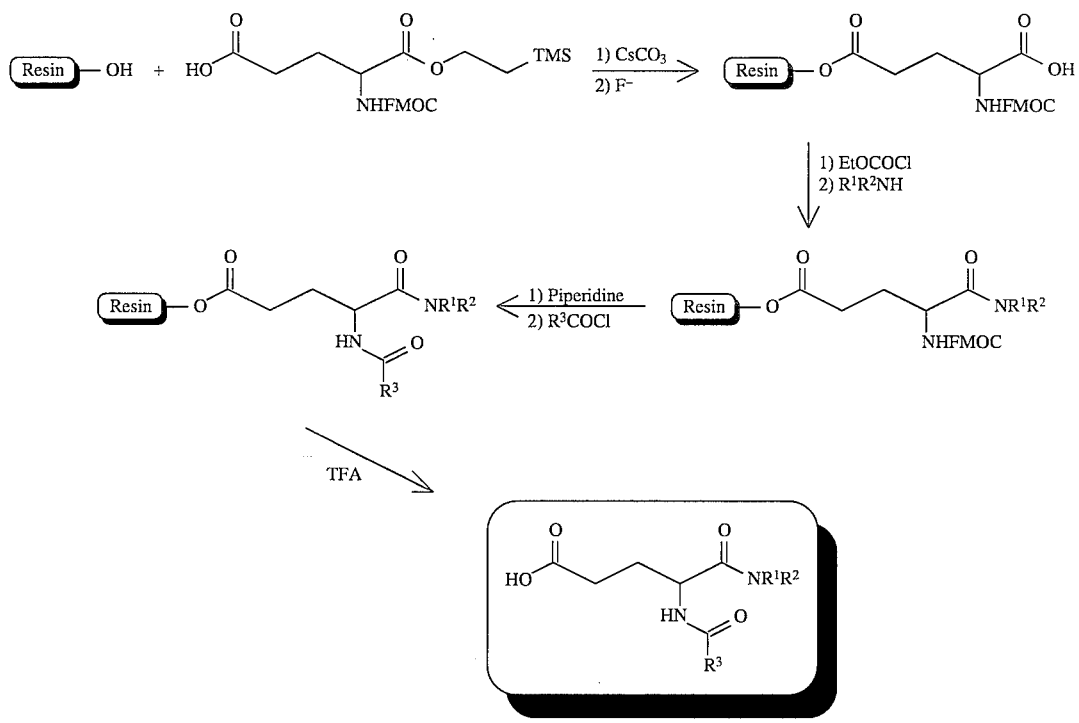

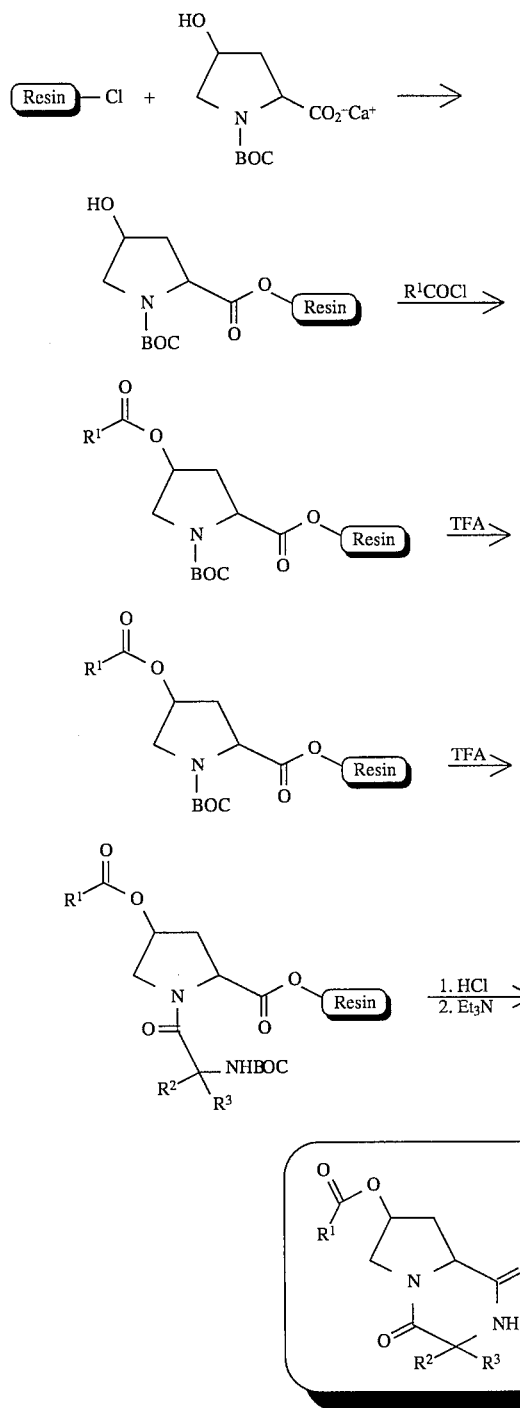

SCHEME 11
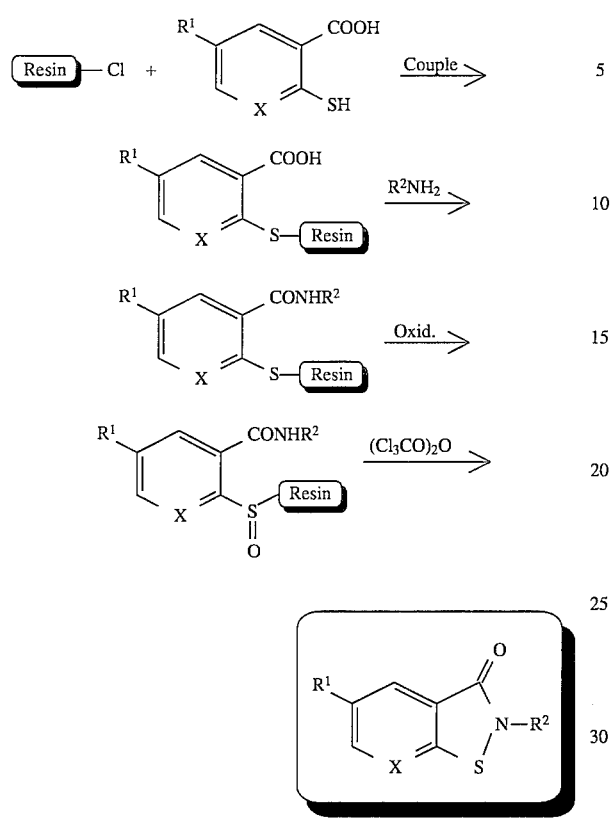
SCHEME 12
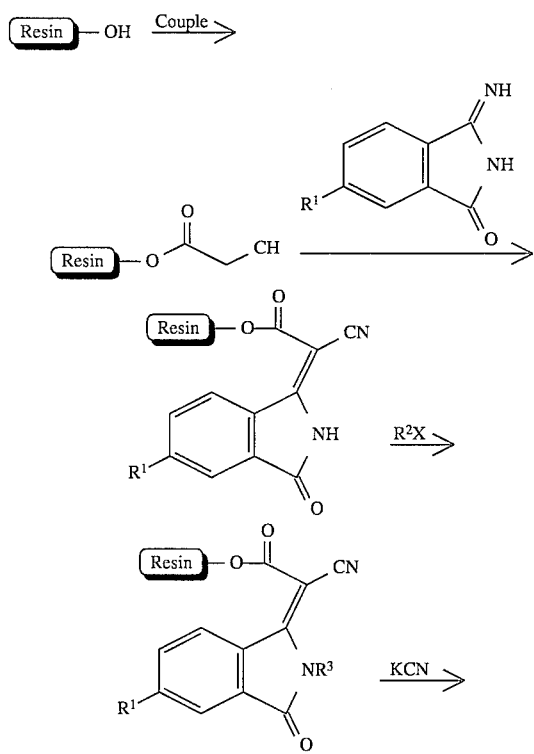
SCHEME 12 -continued
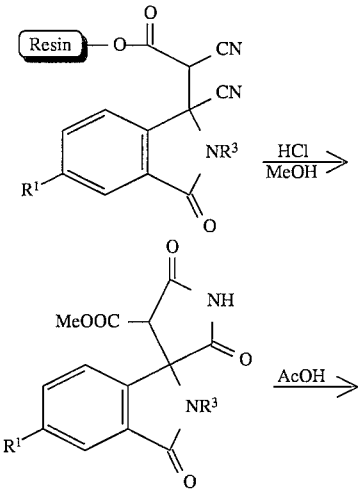
SCHEME 13
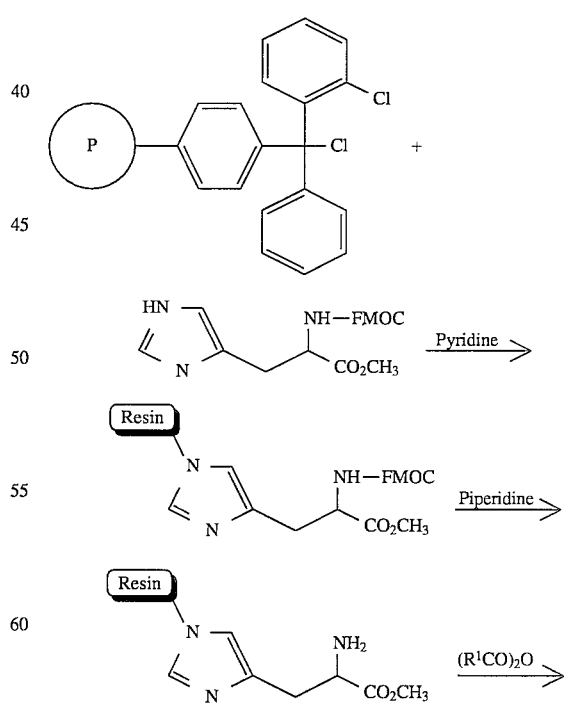

49
-continued
SCHEME 13
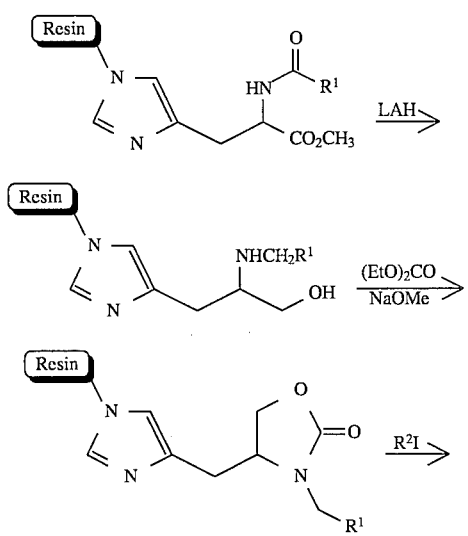
50
-continued
SCHEME 13
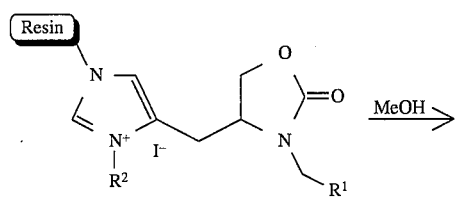
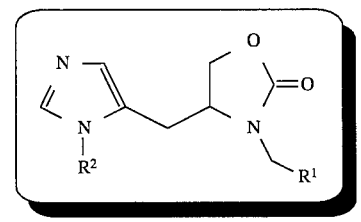
SCHEME 14
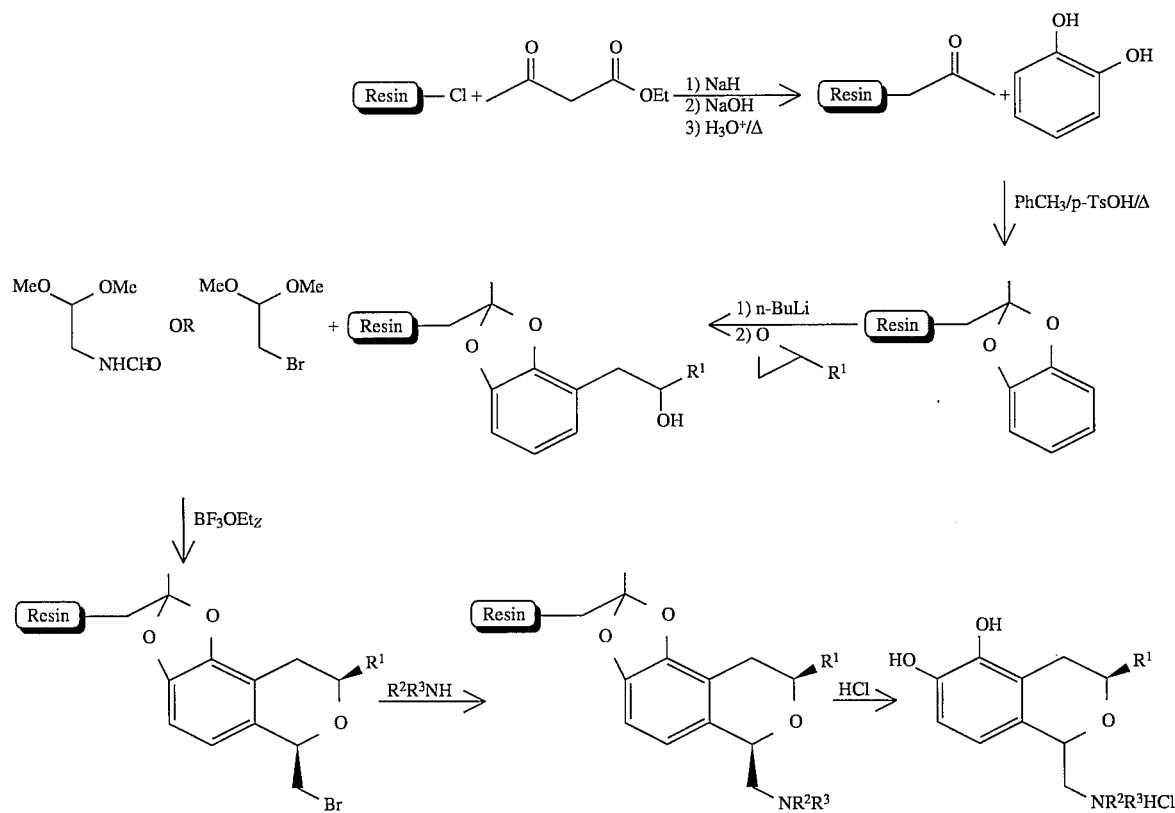
OR -continued
SCHEME 14

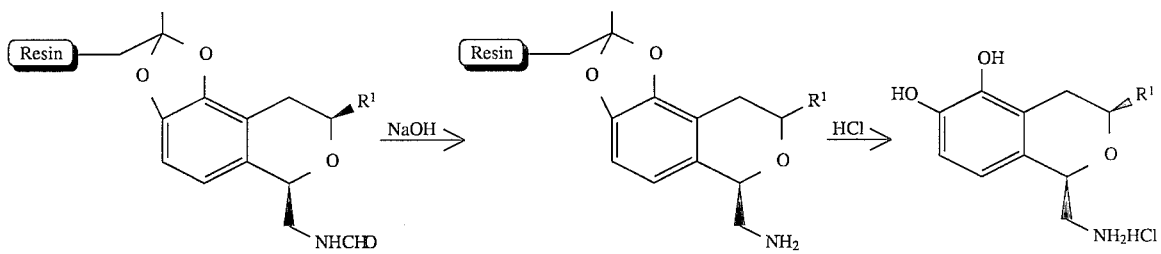

SCHEME 15

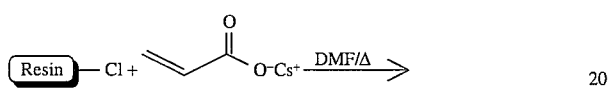

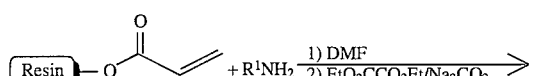

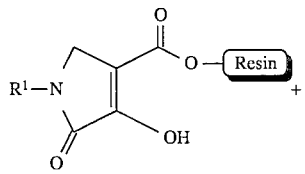

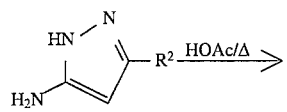

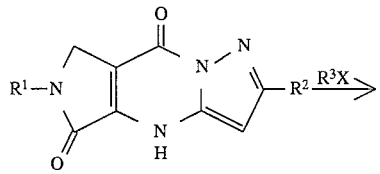

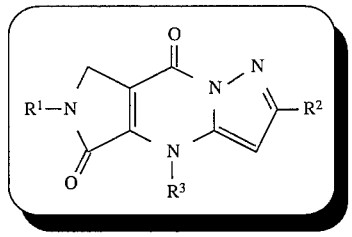

SCHEME 16

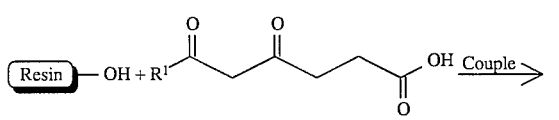

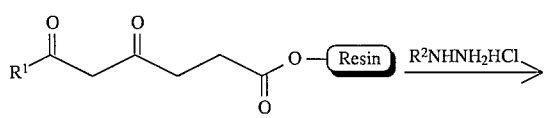

-continued
SCHEME 16

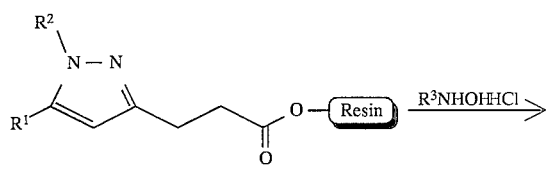

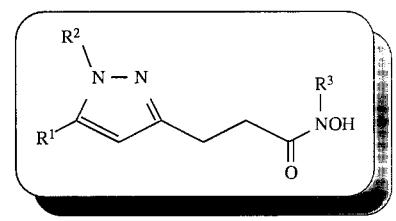

TABLE 1

| Dipeptide | Molecular Formula | M.W. g/mol | Yield (%)* |
|---|---|---|---|
| AlaPhe | $C_{12}H_{16}N_2O_3$.TFA | 350.29 | 40 |
| AlaGly | $C_5H_{10}N_2O_3$.TFA | 260.17 | 41 |
| AlaIle | $C_9H_{18}N_2O_3$.TFA | 316.28 | 85 |
| AlaLeu | $C_9H_{18}N_2O_3$.TFA | 316.28 | 57 |
| AlaAla | $C_6H_{12}N_2O_3$.TFA | 274.19 | 45 |
| AlaPro | $C_8H_{14}N_2O_3$.TFA | 300.23 | 28 |
| AlaVal | $C_8H_{16}N_2O_3$.TFA | 302.25 | 77 |
| AlaTrp | $C_{14}H_{17}N_3O_3$.TFA | 389.33 | 37 |
| IlePhe | $C_{15}H_{22}N_2O_3$.TFA | 392.37 | 35 |
| IleGly | $C_8H_{16}N_2O_3$.TFA | 302.25 | 26 |
| IleIle | $C_{12}H_{24}N_2O_3$.TFA | 358.36 | 85 |
| IleLeu | $C_{12}H_{24}N_2O_3$.TFA | 358.36 | 30 |
| IleAla | $C_9H_{18}N_2O_3$.TFA | 316.28 | 38 |
| IlePro | $C_{11}H_{20}N_2O_3$.TFA | 342.31 | 29 |
| IleVal | $C_{11}H_{23}N_3O_3$.TFA | 344.33 | 62 |
| IleTrp | $C_{11}H_{23}N_3O_3$.TFA | 431.41 | 32 |

*Yields based upon indicated loading of commercially available functionalized resins (0.37–0/60 mmeq./gm)

TABLE 2

Hydantoins

| Number | R1 | R2 | R3 | Yield mg | Yield % |
|---|---|---|---|---|---|
| 1 | H | methyl | H | 4.1 | 67% |
| 2 | H | benzyl | H | 2.5 | 38% |
| 2 | H | H | H | 3.3 | 65% |
| 4 | H | s-butyl | H | 3.1 | 42% |
| 5 | H | i-butyl | H | 4.9 | 61% |
| 6 | H | i-propyl | H | 4.9 | 58% |
| 7 | H | 2-methylindole | H | 5.0 | 35% |
| 8 | phenyl | phenyl | H | 1.4 | 5% |
| 9 | H | methyl | butyl | 1.6 | 17% |
| 10 | H | benzyl | butyl | 3.9 | 47% |
| 11 | H | H | butyl | 1.0 | 13% |
| 12 | H | s-butyl | butyl | 5.3 | 48% |
| 13 | H | i-butyl | butyl | 0.7 | 7% |
| 14 | H | i-propyl | butyl | 0.9 | 8% |
| 15 | H | 2-methylindole | butyl | 0.9 | 5% |
| 16 | phenyl | phenyl | butyl | 1.6 | 5% |
| 17 | H | methyl | allyl | 0.3 | 4% |
| 18 | H | benzyl | allyl | 2.4 | 29% |
| 19 | H | H | allyl | 3.7 | 48% |
| 20 | H | s-butyl | allyl | 3.6 | 36% |
| 21 | H | i-butyl | allyl | 5.0 | 54% |
| 22 | H | i-propyl | allyl | 1.6 | 14% |
| 23 | H | 2-methylindole | allyl | 1.9 | 11% |
| 24 | phenyl | phenyl | allyl | 2.1 | 7% |
| 25 | H | methyl | 2-trifluorotolyl | 2.6 | 23% |
| 26 | H | benzyl | 2-trifluorotolyl | 2.2 | 23% |
| 27 | H | H | 2-trifluorotolyl | 2.9 | 28% |
| 28 | H | s-butyl | 2-trifluorotolyl | 5.7 | 46% |
| 29 | H | i-butyl | 2-triflurorotolyl | 4.7 | 37% |
| 30 | H | i-propyl | 2-trifluorotolyl | 4.9 | 33% |
| 31 | H | 2-methylindole | 2-trifluorotolyl | 3.0 | 15% |
| 32 | phenyl | phenyl | 2-trifluorotolyl | 0.0 | 0% |
| 33 | H | methyl | 4-methoxyphenyl | 3.1 | 22% |
| 34 | H | benzyl | 4-methoxyphenyl | 3.5 | 32% |
| 35 | H | H | 4-methoxyphenyl | 5.6 | 46% |
| 36 | H | s-butyl | 4-methoxyphenyl | 11.5 | 81% |
| 37 | H | i-butyl | 4-methoxyphenyl | 3.2 | 21% |
| 38 | H | i-propyl | 4-methoxyphenyl | 4.1 | 24% |
| 39 | H | 2-methylindole | 4-methoxyphenyl | 4.9 | 22% |
| 40 | phenyl | phenyl | 4-methoxyphenyl | 3.0 | 7% |

*Yields based upon reported loading of commercially available functionalized resins (0.34–1.04 mEq/g)

TABLE 3

Benzodiazepines

| Number | R1 | R2 | R3 | R4 | Yield mg | Yield % | IC$_{50}$ nM |
|---|---|---|---|---|---|---|---|
| 1 | methyl | phenyl | H | H | 10.0 | 66% | 5795 |
| 2 | methyl | phenyl | 5-chloro | H | 13.0 | 72% | 89 |
| 3 | methyl | 4-methoxyphenyl | H | H | 14.0 | 81% | >1 mM |
| 4 | methyl | phenyl | 5-nitro | H | 16.0 | 87% | 482 |
| 5 | methyl | phenyl | 4-methyl | isopropyl | 7.0 | 37% | >1 mM |
| 6 | methyl | phenyl | 5-nitro | methyl | 6.0 | 31% | 1000 |
| 7 | methyl | cyclohexyl | H | H | 7.0 | 43% | >1 mM |
| 8 | methyl | thienyl | H | H | 15.0 | 96% | 5902 |
| 9 | H | phenyl | H | H | 24.0 | 109% | 515 |
| 10 | H | phenyl | 5-chloro | H | 13.0 | 54% | 32 |
| 11 | H | 4-methoxyphenyl | H | H | 12.0 | 50% | 28255 |
| 12 | H | phenyl | 5-nitro | H | 10.0 | 37% | 16 |
| 13 | H | phenyl | 4-methyl | isopropyl | <1 | <5% | 18581 |
| 14 | H | phenyl | 5-nitro | methyl | 15.0 | 56% | 64 |
| 15 | H | cyclohexyl | H | H | 4.0 | 18% | 25723 |
| 16 | H | thienyl | H | H | 17.0 | 75% | 1117 |
| 17 | 2-methylindole | phenyl | H | H | 12.0 | 54% | >1 mM |
| 18 | 2-methylindole | phenyl | 5-chloro | H | 7.0 | 29% | >1 mM |
| 19 | 2-methylindole | 4-methoxyphenyl | H | H | 6.0 | 25% | >1 mM |
| 20 | 2-methylindole | phenyl | 5-nitro | H | 5.0 | 19% | 12700 |
| 21 | 2-methylindole | phenyl | 4-methyl | isopropyl | 4.0 | 15% | >1 mM |
| 22 | 2-methylindole | phenyl | 5-nitro | methyl | 3.0 | 12% | >1 mM |
| 23 | 2-methylindole | cyclohexyl | H | H | 7.0 | 31% | >1 mM |
| 24 | 2-methylindole | thienyl | H | H | 7.0 | 31% | >1 mM |
| 25 | 4-hydroxytolyl | phenyl | H | H | 12.0 | 60% | >1 mM |
| 26 | 4-hydroxytolyl | phenyl | 5-chloro | H | 11.0 | 50% | >1 mM |
| 27 | 4-hydroxytolyl | 4-methoxyphenyl | H | H | 9.0 | 42% | >1 mM |
| 28 | 4-hydroxytolyl | phenyl | 5-nitro | H | 8.0 | 35% | >1 mM |
| 29 | 4-hydroxytolyl | phenyl | 4-methyl | isopropyl | 9.0 | 39% | >1 mM |
| 30 | 4-hydroxytolyl | phenyl | 5-nitro | methyl | <1 | <5% | >1 mM |
| 31 | 4-hydroxytolyl | cyclohexyl | H | H | 21.0 | 104% | >1 mM |
| 32 | 4-hydroxytolyl | thienyl | H | H | 30.0 | 145% | >1 mM |
| 33 | i-propyl | phenyl | H | H | 17.0 | 77% | >1 mM |
| 34 | i-propyl | phenyl | 5-chloro | H | 10.0 | 39% | >1 mM |
| 35 | i-propyl | 4-methoxyphenyl | H | H | 7.0 | 29% | >1 mM |
| 36 | i-propyl | phenyl | 5-nitro | H | 7.0 | 27% | >1 mM |
| 37 | i-propyl | phenyl | 4-methyl | isopropyl | 11.0 | 42% | >1 mM |
| 38 | i-propyl | phenyl | 5-nitro | methyl | 6.0 | 22% | >1 mM |
| 39 | i-propyl | cyclohexyl | H | H | 7.0 | 30% | >1 mM |
| 40 | i-propyl | thienyl | H | H | 20.0 | 87% | >1 mM |

*Yields based on indicated loading of commercially available functionalized resins (0.37–0.60 mmEq/g)
†IC$_{50}$ values were also obtained for the commercially available Diazepam (0.67 nM), Nordiazepam (0.2 nM), and Nitrazeam (1.46 nM) the latter 2 corresponding to samples Number 10 and 12, respectively.

TABLE 4

Quinolones

Structure: Quinolone core with F at 6-position, R²R³N at 7-position, X at 8-position, R¹ on N-1, 4-oxo, 3-carboxylic acid.

| Cpd No. | R¹ | R²R³N | X |
|---|---|---|---|
| 1 | 2,4-difluorophenyl | piperidin-1-yl | CH |
| 2 | 2,4-difluorophenyl | piperazin-1-yl (NH) | CH |
| 3 | 2,4-difluorophenyl | 4-methylpiperazin-1-yl | CH |
| 4 | 2,4-difluorophenyl | 3-(ethylaminomethyl)pyrrolidin-1-yl | CH |
| 5 | cyclopropyl | piperidin-1-yl | CH |
| 6 | cyclopropyl | piperazin-1-yl (NH) | CH |
| 7 | cyclopropyl | 4-methylpiperazin-1-yl | CH |
| 8 | cyclopropyl | 3-(ethylaminomethyl)pyrrolidin-1-yl | CH |
| 9 | Ethyl | piperidin-1-yl | CH |
| 10 | Ethyl | piperazin-1-yl (NH) | CH |
| 11 | Ethyl | 4-methylpiperazin-1-yl | CH |
| 12 | Ethyl | 3-(ethylaminomethyl)pyrrolidin-1-yl | CH |
| 13 | 2,4-difluorophenyl | piperidin-1-yl | CF |
| 14 | 2,4-difluorophenyl | piperazin-1-yl (NH) | CF |
| 15 | 2,4-difluorophenyl | 4-methylpiperazin-1-yl | CF |
| 16 | 2,4-difluorophenyl | 3-(ethylaminomethyl)pyrrolidin-1-yl | CF |

TABLE 4-continued
Quinolones
| Cpd No. | R¹ | R²R³N | X |
|---|---|---|---|
| 17 |  |  | CF |
| 18 | 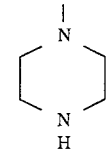 |  | CF |
| 19 | 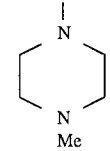 |  | CF |
| 20 |  |  | CF |
| 21 | Ethyl | 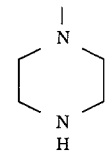 | CF |
| 22 | Ethyl | 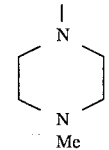 | CF |
| 23 | Ethyl | 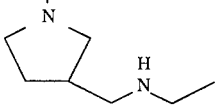 | CF |
| 24 | Ethyl | 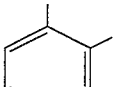 | CF |
| 25 |  | 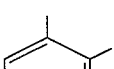 | N |
| 26 | 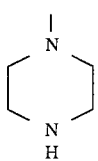 | 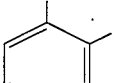 | N |
| 27 |  | 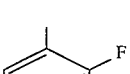 | N |
| 28 | 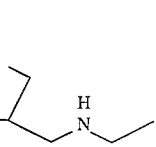 |  | N |
| 29 | 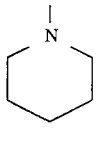 | 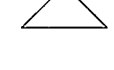 | N |
| 30 | 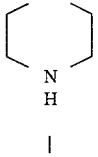 | 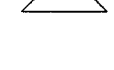 | N |
| 31 |  |  | N |
| 32 |  |  | N |

TABLE 4-continued

Quinolones

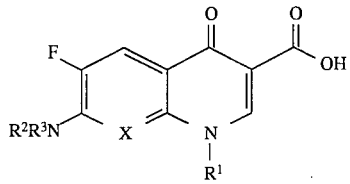

| Cpd No. | R¹ | R²R³N | X |
|---|---|---|---|
| 33 | Ethyl | 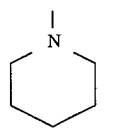 | N |
| 34 | Ethyl | 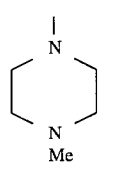 | N |
| 35 | Ethyl | 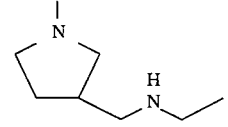 | N |
| 36 | Ethyl |  | N |

TABLE 5

Keto-ureas

| Cpd No. | R¹ | R² |
|---|---|---|
| 1 | Ethyl |  |
| 2 |  |  |
| 3 | Ethyl | Methyl |

TABLE 5-continued

Keto-ureas

| Cpd No. | R¹ | R² |
|---|---|---|
| 4 |  | Methyl |

| | | |
|---|---|---|
| 5 | Ethyl |  |
| 6 |  |  |
| 7 | Ethyl | Methyl |
| 8 |  | Methyl |

TABLE 6

N²-Substituted Hydantoins

| Cpd No. | R¹ | R² | R³ |
|---|---|---|---|
| 1 | $CH_3$ | $CH_3CH_2$ | H |
| 2 | $CH_3$ | $CH_3CH_2$ | $CH_2CH=CH_2$ |
| 3 | $CH_3$ | $C_6H_5CH_2$ | H |
| 4 | $CH_3$ | $C_6H_5CH_2$ | $CH_2CH=CH_2$ |
| 5 | $C_6H_5CH_2$ | $CH_3CH_2$ | H |
| 6 | $C_6H_5CH_2$ | $CH_3CH_2$ | $CH_2CH=CH_2$ |
| 7 | $C_6H_5CH_2$ | $C_6H_5CH_2$ | H |
| 8 | $C_6H_5CH_2$ | $C_6H_5CH_2$ | $CH_2CH=CH_2$ |

TABLE 7
(R)-4-BENZAMIDO-5-OXOPENTANOIC ACIDS
| Cpd No. | R¹R²N | R³ |
|---|---|---|
| 1 | nBuHN | 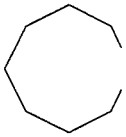 |
| 2 |  |  |
| 3 | (CH$_3$CH$_2$CH$_2$CH$_2$CH$_2$)$_2$N |  |
| 4 |  | 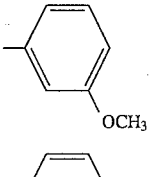 |
| 5 | nBuHN | 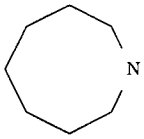 |
| 6 | 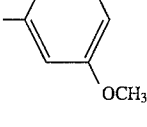 | 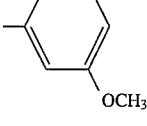 |
| 7 | (CH$_3$CH$_2$CH$_2$CH$_2$CH$_2$)$_2$N |  |
| 8 | 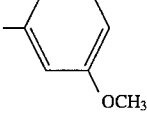 | 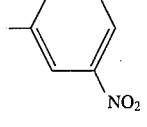 |
| 9 | nBuHN | 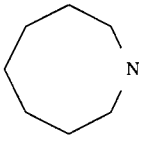 |
| 10 | 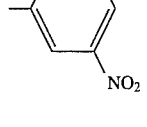 |  |
TABLE 7-continued
(R)-4-BENZAMIDO-5-OXOPENTANOIC ACIDS
| Cpd No. | R¹R²N | R³ |
|---|---|---|
| 11 | (CH$_3$CH$_2$CH$_2$CH$_2$CH$_2$)$_2$N |  |
| 12 |  | 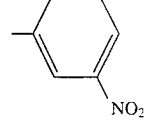 |
TABLE 8
Diketopiperazines
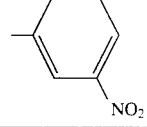
| Cpd No. | R¹ | R² | R³ |
|---|---|---|---|
| 1 |  | H | H |
| 2 | 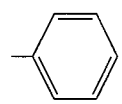 | H | CH$_3$ |
| 3 | 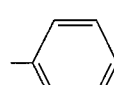 | H | (CH$_3$)$_2$CH |
| 4 | 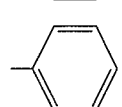 | H | PhCH$_2$ |
| 5 | 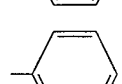 | Ph | Ph |

TABLE 8-continued

Diketopiperazines

| Cpd No. | R¹ | R² | R³ |
|---|---|---|---|
| 6 | 4-Ph-C₆H₄ | H | H |
| 7 | 4-Ph-C₆H₄ | H | CH₃ |
| 8 | 4-Ph-C₆H₄ | H | (CH₃)₂CH |
| 9 | 4-Ph-C₆H₄ | H | PhCH₂ |
| 10 | 4-Ph-C₆H₄ | Ph | Ph |
| 11 | 4-Cl-C₆H₄ | H | H |
| 12 | 4-Cl-C₆H₄ | H | CH₃ |
| 13 | 4-Cl-C₆H₄ | H | (CH₃)₂CH |
| 14 | 4-Cl-C₆H₄ | H | PhCH₂ |
| 15 | 4-Cl-C₆H₄ | Ph | Ph |
| 16 | 4-OCH₃-C₆H₄ | H | H |
| 17 | 4-OCH₃-C₆H₄ | H | CH₃ |
| 18 | 4-OCH₃-C₆H₄ | H | (CH₃)₂CH |
| 19 | 4-OCH₃-C₆H₄ | H | PhCH₂ |
| 20 | 4-OCH₃-C₆H₄ | Ph | Ph |
| 21 | —CH₃ | H | H |
| 22 | —CH₃ | H | CH₃ |
| 23 | —CH₃ | H | (CH₃)₂CH |
| 24 | —CH₃ | H | PhCH₂ |
| 25 | —CH₃ | Ph | Ph |
| 26 | 4-NO₂-C₆H₄ | H | H |
| 27 | 4-NO₂-C₆H₄ | H | CH₃ |
| 28 | 4-NO₂-C₆H₄ | H | (CH₃)₂CH |
| 29 | 4-NO₂-C₆H₄ | H | PhCH₂ |
| 30 | 4-NO₂-C₆H₄ | Ph | Ph |
| 31 | —CF₃ | H | H |
| 32 | —CF₃ | H | CH₃ |
| 33 | —CF₃ | H | (CH₃)₂CH |
| 34 | —CF₃ | H | PhCH₂ |
| 35 | —CF₃ | Ph | Ph |
| 36 | -tBu | H | H |
| 37 | -tBu | H | CH₃ |
| 38 | -tBu | H | (CH₃)₂CH |
| 39 | -tBu | H | PhCH₂ |
| 40 | -tBu | Ph | Ph |

TABLE 9

2H-Pyranones

| Cpd No. | R¹ | R² |
|---|---|---|
| 1 | H | 1-(4-fluorophenyl)-5-isopropyl-2-phenyl-N-phenyl-pyrrole-3-carboxamide, N-propyl (attached via position 2 of pyrrole bearing 4-fluorophenyl; 4-position bears Ph; 3-position bears CONHPh; 5-position bears isopropyl; N bears propyl) |
| 2 | $CH_3CH_2$ | same pyrrole substituent as Cpd 1 |

TABLE 9-continued

2H-Pyranones

| Cpd No. | R¹ | R² |
|---|---|---|
| 3 | $C_6H_5CH_2$ | N-propyl-2,3,4-triphenyl-5-methyl-pyrrole (attached at position 2; 3,4-Ph; 5-CH₃; N-propyl) |

TABLE 10

N-aryl Piperazines

| Cpd No. | R¹ | R² | Cpd No. | R¹ | R² |
|---|---|---|---|---|---|
| 1 | H | 3-pyridyl | 7 | H | 3-pyridyl |
| 2 | H | 2-naphthyl | 8 | H | 2-naphthyl |
| 3 | phenyl | 3-pyridyl | 9 | phenyl | 3-pyridyl |
| 4 | phenyl | 2-naphthyl | 10 | phenyl | 2-naphthyl |
| 5 | 2-pyridyl | 3-pyridyl | 11 | 2-pyridyl | 3-pyridyl |
| 6 | 2-pyridyl | 2-naphthyl | 12 | 2-pyridyl | 2-naphthyl |

TABLE 10-continued

N-aryl Piperazines

| Cpd No. | R¹ | R² | Cpd No. | R¹ | R² |
|---|---|---|---|---|---|
| 13 | H | 3-pyridyl | 19 | H | 3-pyridyl |
| 14 | H | 2-naphthyl | 20 | H | 2-naphthyl |
| 15 | phenyl | 3-pyridyl | 21 | phenyl | 3-pyridyl |
| 16 | phenyl | 2-naphthyl | 22 | phenyl | 2-naphthyl |
| 17 | 2-pyridyl | 3-pyridyl | 23 | 2-pyridyl | 3-pyridyl |
| 18 | 2-pyridyl | 2-naphthyl | 24 | 2-pyridyl | 2-naphthyl |

TABLE 11

Benzoisothiazolones

| Cpd No. | X | R¹ | R² |
|---|---|---|---|
| 1 | CH | H | 4-methoxyphenyl |
| 2 | CH | H | cyclohexyl |
| 3 | CH | H | benzyl (CH₂-phenyl) |

TABLE 11-continued

Benzoisothiazolones

| Cpd No. | X | R¹ | R² |
|---|---|---|---|
| 4 | CH | Cl | 4-methoxyphenyl |
| 5 | CH | Cl | cyclohexyl |
| 6 | CH | Cl | benzyl (CH₂-phenyl) |

TABLE 11-continued
Benzoisothiazolones
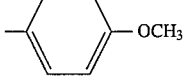
| Cpd No. | X | R¹ | R² |
|---|---|---|---|
| 7 | N | H |  —OCH₃ |
| 8 | N | H | 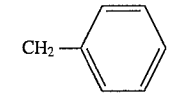 |
| 9 | N | H | CH₂—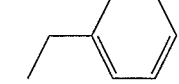 |
TABLE 12
Spirosuccimides
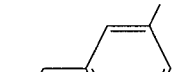
| Cpd No. | R¹ | R² |
|---|---|---|
| 1 | H | CH₃ |
| 2 | H | 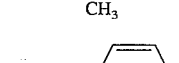 |
| 3 | H |  Br |
| 4 | Cl | CH₃ |
| 5 | Cl | 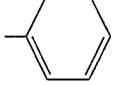 |
TABLE 12-continued
Spirosuccimides
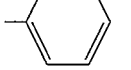
| Cpd No. | R¹ | R² |
|---|---|---|
| 6 | Cl | 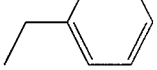 Br |
| 7 | 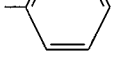 | CH₃ |
| 8 | 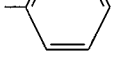 | 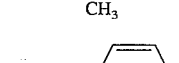 |
| 9 | 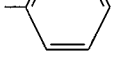 | 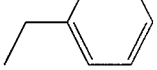 Br |
TABLE 13
Pilocarpine Analogs
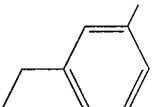
| Cpd No. | R¹ | R² |
|---|---|---|
| 1 | CH₃ | CH₃ |
| 2 | CH₃ | Hexyl |
| 3 | (CH₃)₂CH | CH₃ |
| 4 | (CH₃)₂CH | Hexyl |

TABLE 14

3-Substituted 1-(aminomethyl)-3,4-dihydro-5,6-dihydroxy-1H-2-benzopyrans

| Cpd No. | R¹ | R²R³N |
|---|---|---|
| 1 | phenyl | NH₂ |
| 2 | cyclohexyl | NH₂ |
| 3 | phenyl | HN-CH₂-phenyl |
| 4 | cyclohexyl | HN-CH₂-phenyl |
| 5 | phenyl | HN-CH₂CH=CH₂ |
| 6 | cyclohexyl | HN-CH₂CH=CH₂ |

TABLE 15

Pyrimidinediones

| Cpd No. | R¹ | R² | R³ |
|---|---|---|---|
| 1 | Hexyl | phenyl | acetylphenyl |
| 2 | Hexyl | phenyl | hexenyl |
| 3 | Hexyl | 4-chlorophenyl | acetylphenyl |
| 4 | Hexyl | 4-chlorophenyl | hexenyl |

TABLE 15-continued

Pyrimidinediones

[Structure diagram showing pyrimidinedione core with R¹, R², R³ substituents]

| Cpd No. | R¹ | R² | R³ |
|---|---|---|---|
| 5 | cyclohexyl | phenyl | phenacyl (C(O)-phenyl) |
| 6 | cyclohexyl | phenyl | hex-5-enyl |
| 7 | cyclohexyl | 4-chlorophenyl | phenacyl (C(O)-phenyl) |
| 8 | cyclohexyl | 4-chlorophenyl | hex-5-enyl |

TABLE 16

Tepoxalin Derivatives

[Structure diagram showing pyrazole with R¹, R², and CH₂CH₂C(O)N(OH)R³ side chain]

| Cpd No. | R¹ | R² | R³ |
|---|---|---|---|
| 1 | phenyl | 4-methoxyphenyl | benzyl |
| 2 | phenyl | 4-methoxyphenyl | Methyl |
| 3 | phenyl | 4-methylphenyl | benzyl |
| 4 | phenyl | 4-methylphenyl | Methyl |
| 5 | 4-chlorophenyl | 4-methoxyphenyl | benzyl |
| 6 | 4-chlorophenyl | 4-methoxyphenyl | Methyl |
| 7 | 4-chlorophenyl | 4-methylphenyl | benzyl |
| 8 | 4-chlorophenyl | 4-methylphenyl | Methyl |

We claim:

1. An apparatus for multiple, simultaneous synthesis of compounds comprising:
   a plurality of reaction tubes, each reaction tube having an upper end and a lower end, said lower ends each having a filter device,
   a reservoir member having means for receiving the filter devices on the lower ends of said plurality of reaction tubes,
   a holder member removably located adjacent to the reservoir member having a plurality of apertures for supporting said plurality of reaction tubes,
   a manifold member having a central cavity for enclosing the upper ends of said plurality of reaction tubes, and
   means for equalizing pressure differentials within said apparatus, wherein said means for equalizing comprises at least one pressure equalization aperture located on at least one of said reaction tubes.

2. The apparatus as set forth in claim 1 wherein at least one pressure equalization aperture is located on each of said reaction tubes.

3. The apparatus as set forth in claim 2 wherein said apertures are located above the filter devices on said lower ends of said reaction tubes.

4. The apparatus as set forth in claim 1 wherein said aperture has a diameter from 100–2000 μm.

5. The apparatus as set forth in claim 1 further comprising
   first sealing means for providing a seal between said holder member and said reservoir member,
   second sealing means for providing a seal between said holder member and said manifold, and
   fastening means for fastening together said reservoir member, holder member and manifold.

6. The apparatus as set forth in claim 5 wherein fastening means comprises a first fastening mechanism for fastening together said reservoir member and said holder member, and a second fastening mechanism for fastening together said holder member and said manifold member.

7. An apparatus for multiple, simultaneous synthesis of compounds comprising:
   a plurality of reaction tubes, each reaction tube having an upper end and a lower end,
   a filter member positioned on said lower ends of each of said reaction tubes,
   a reservoir member, said reservoir member having a plurality of reaction wells, one of said reaction wells positioned to receive a filter member on the lower end of one of said reaction tubes,
   a holder member removably located adjacent to the reservoir member, said holder member having means for holding said plurality of reaction tubes therein,
   a manifold member removably positioned on said holder member, said manifold member enclosing said upper ends of said plurality of reaction tubes,
   first sealing means for sealing said holder member to said reservoir member,
   second sealing means for sealing said manifold to said holder member,
   fastening means for securing together said holder member, reservoir member and manifold member, and
   pressure equalizing means for equalizing pressure differentials within said apparatus, wherein said means for equalizing comprises at least one pressure equalization aperture located on at least one of said reaction tubes.

8. The apparatus as set forth in claim 7 wherein said pressure equalizing means comprises at least one aperture in each of said reaction tubes.

9. The apparatus as set forth in claim 8 wherein said apertures are positioned above said filter members.

10. An apparatus for multiple, simultaneous synthesis of compounds comprising:
    a plurality of reaction tubes, each reaction tube having an upper end and a lower end, said lower ends each having a filter device,
    a reservoir member having means for receiving the filter devices on the lower ends of said plurality of reaction tubes,
    a holder member removably located adjacent to the reservoir member having a plurality of apertures for supporting said plurality of reaction tubes,
    a manifold member having a central cavity for enclosing the upper ends of said plurality of reaction tubes, and
    means for equalizing pressure differentials within said apparatus, wherein said means for equalizing comprises at least one capillary tube located substantially adjacent to and substantially parallel to at least one of said reaction tubes, said capillary tube extending from said reservoir member, through said holder member and into said manifold member.

11. The apparatus as set forth in claim 10 further comprising:
    first sealing means for providing a seal between said holder member and said reservoir member,
    second sealing means for providing a seal between said holder member and said manifold, and
    fastening means for fastening together said reservoir member, holder member and manifold.

12. The apparatus as set forth in claim 10, wherein fastening means comprises a first fastening mechanism for fastening together said reservoir member and said holder member, and a second fastening mechanism for fastening together said holder member and said manifold member.

13. An apparatus for multiple, simultaneous synthesis of compounds comprising:
    a plurality of reaction tubes, each reaction tube having an upper end and a lower end, said lower ends each having a filter device,
    a reservoir member having reaction wells for receiving the filter devices on the lower ends of said plurality of reaction tubes,
    a holder member removably located adjacent to the reservoir member having a plurality of apertures for supporting said plurality of reaction tubes,
    a manifold member having a central cavity for enclosing the upper ends of said plurality of reaction tubes, and
    a means for equalizing pressure differentials separately and independently between each of said reaction tubes and each of said corresponding reaction wells.

14. The apparatus as set forth in claim 13, wherein said means for equalizing pressure differentials comprises at least one aperture in said reaction tubes adjacent said filter member.

15. The apparatus as set forth in claim 13, wherein said means for equalizing pressure differentials comprises a capillary tube positioned adjacent said reaction tubes.

16. The apparatus as set forth in claim 13, wherein said means for equalizing pressure differentials comprises a tubular jacket member positioned concentric with and outside of said reaction tubes.

* * * * *